(12) United States Patent
Morrison et al.

(10) Patent No.: US 10,093,745 B2
(45) Date of Patent: Oct. 9, 2018

(54) ANTI-CSPG4 FUSIONS WITH INTERFERON FOR THE TREATMENT OF MALIGNANCY

(71) Applicant: The Regents of the University of California, Oakland, CA (US)

(72) Inventors: Sherie L. Morrison, Los Angeles, CA (US); John M. Timmerman, Los Angeles, CA (US); Kham M. Trinh, Alhambra, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/893,912

(22) PCT Filed: May 29, 2014

(86) PCT No.: PCT/US2014/040036
§ 371 (c)(1),
(2) Date: Nov. 24, 2015

(87) PCT Pub. No.: WO2014/194100
PCT Pub. Date: Dec. 4, 2014

(65) Prior Publication Data
US 2016/0115242 A1 Apr. 28, 2016

Related U.S. Application Data

(60) Provisional application No. 61/828,590, filed on May 29, 2013.

(51) Int. Cl.
| | |
|---|---|
| *C07K 16/30* | (2006.01) |
| *C07K 14/56* | (2006.01) |
| *C07K 16/28* | (2006.01) |
| *A61K 45/06* | (2006.01) |
| *A61K 39/395* | (2006.01) |
| *C07K 14/565* | (2006.01) |
| *A61K 38/21* | (2006.01) |
| *A61N 5/10* | (2006.01) |
| *C07K 14/57* | (2006.01) |
| *A61K 39/00* | (2006.01) |

(52) U.S. Cl.
CPC .......... *C07K 16/30* (2013.01); *A61K 38/212* (2013.01); *A61K 38/215* (2013.01); *A61K 38/217* (2013.01); *A61K 39/39558* (2013.01); *A61K 45/06* (2013.01); *A61N 5/10* (2013.01); *C07K 14/56* (2013.01); *C07K 14/565* (2013.01); *C07K 14/57* (2013.01); *C07K 16/3053* (2013.01); *A61K 2039/505* (2013.01); *C07K 2317/565* (2013.01); *C07K 2317/622* (2013.01); *C07K 2317/73* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,696,237 A | 12/1997 | Fitzgerald et al. | |
| 5,824,782 A | 10/1998 | Hölzer et al. | |
| 5,980,895 A | 11/1999 | Pastan et al. | |
| 6,428,788 B1 | 8/2002 | Debinski et al. | |
| 6,800,735 B2 | 10/2004 | Whiny et al. | |
| 6,893,625 B1 | 5/2005 | Robinson et al. | |
| 7,005,498 B1 | 2/2006 | Steinaa et al. | |
| 7,151,164 B2 | 12/2006 | Hansen et al. | |
| 7,919,078 B2 | 4/2011 | Schreiber et al. | |
| 8,258,263 B2 | 9/2012 | Morrison et al. | |
| 8,563,692 B2 | 10/2013 | Morrison et al. | |
| 9,139,634 B2 | 9/2015 | Morrison et al. | |
| 9,534,033 B2 | 1/2017 | Morrison et al. | |
| 9,803,021 B2 | 10/2017 | Morrison | |
| 2002/0193569 A1 | 12/2002 | Hanna | |
| 2003/0219433 A1 | 11/2003 | Hansen et al. | |
| 2004/0005647 A1 | 1/2004 | Denardo et al. | |
| 2005/0008649 A1 | 1/2005 | Shin et al. | |
| 2005/0079154 A1 | 4/2005 | Yarkoni et al. | |
| 2005/0232931 A1 | 10/2005 | Ma et al. | |
| 2006/0228300 A1 | 10/2006 | Chang et al. | |
| 2006/0263368 A1 | 11/2006 | Rosenblum et al. | |
| 2006/0287509 A1 | 12/2006 | Marks et al. | |

(Continued)

FOREIGN PATENT DOCUMENTS

| | | |
|---|---|---|
| CN | 1751122 A | 3/2006 |
| JP | 11-505132 A | 5/1999 |

(Continued)

OTHER PUBLICATIONS

Mickle et al., MEd. Clin. N.America (2000), vol. 84, No. 3, p. 597-607.*
Wells., Biochemistry (1990), vol. 29, No. 37, p. 8509-8517.*
U.S. Office Action [Requirement for Restriction/Election] dated May 13, 2016 issued in U.S. Appl. No. 14/649,888.
U.S. Office Action dated Oct. 3, 2016 issued in U.S. Appl. No. 14/649,888.
U.S. Notice of Allowance dated Jun. 16, 2017 issued in U.S. Appl. No. 14/649,888.
U.S. Office Action [Requirement for Restriction/Election] dated Mar. 10, 2011 issued in U.S. Appl. No. 12/678,981.
U.S. Office Action dated Jul. 5, 2011 issued in U.S. Appl. No. 12/678,981.

(Continued)

*Primary Examiner* — Joanne Hama
*Assistant Examiner* — Jegatheesan Seharaseyon
(74) *Attorney, Agent, or Firm* — Tom Hunter; Weaver Austin Villeneuve & Sampson LLP

(57) ABSTRACT

In various embodiments chimeric moieties (constructs) are provided that show significant efficacy against cancers. In certain embodiments the constructs comprise a targeting moiety that specifically binds CSPG4 attached to an interferon or to a mutant interferon. In certain embodiments, the constructs comprise anti-CSPG4 antibody attached to an interferon alpha (IFN-α) or to a mutant interferon alpha or to an interferon beta (IFN-β) or to a mutant interferon beta, or to an interferon gamma (IFN-γ) or to a mutant interferon gamma.

11 Claims, 14 Drawing Sheets

Specification includes a Sequence Listing.

(56) References Cited

U.S. PATENT DOCUMENTS

| | | | |
|---|---|---|---|
| 2008/0166319 | A1 | 7/2008 | Schreiber et al. |
| 2010/0047164 | A1* | 2/2010 | Bigner ............... A61K 51/1027 424/1.49 |
| 2010/0172868 | A1 | 7/2010 | Morrison et al. |
| 2010/0297076 | A1 | 11/2010 | Morrison et al. |
| 2011/0104112 | A1 | 5/2011 | Morrison et al. |
| 2011/0123554 | A1 | 5/2011 | Osterroth et al. |
| 2011/0165122 | A1 | 7/2011 | Shahangian et al. |
| 2011/0171229 | A1 | 7/2011 | Ferrone et al. |
| 2012/0237442 | A1 | 9/2012 | Rossi et al. |
| 2012/0258073 | A1 | 10/2012 | Gerdes et al. |
| 2014/0079668 | A1 | 3/2014 | Morrison et al. |
| 2016/0115239 | A1 | 4/2016 | Morrison |
| 2017/0151342 | A1 | 6/2017 | Morrison et al. |

FOREIGN PATENT DOCUMENTS

| | | |
|---|---|---|
| JP | 11-513669 A | 11/1999 |
| JP | 2003-508023 A | 3/2003 |
| JP | 2003-535908 A | 12/2003 |
| JP | 2004-93527 A | 3/2004 |
| JP | 2004-528014 A | 9/2004 |
| JP | 2005-520853 A | 7/2005 |
| JP | 2006-500904 A | 1/2006 |
| JP | 2008-505174 A | 2/2008 |
| JP | 2009-511495 A | 3/2009 |
| JP | 5591701 B2 | 9/2014 |
| WO | WO 97/13529 A1 | 4/1997 |
| WO | WO 97/24137 | 7/1997 |
| WO | WO 01/03737 A1 | 1/2001 |
| WO | WO 01/097844 A1 | 12/2001 |
| WO | WO 02/46227 A2 | 6/2002 |
| WO | WO 03/068821 A2 | 8/2003 |
| WO | WO 2003/080106 A1 | 10/2003 |
| WO | WO 2004/074486 A2 | 9/2004 |
| WO | WO 2006/000448 A2 | 1/2006 |
| WO | WO 2006/010891 A2 | 2/2006 |
| WO | WO 2006/019447 A1 | 2/2006 |
| WO | WO 2006/127757 A2 | 11/2006 |
| WO | WO 2007/027106 A1 | 3/2007 |
| WO | WO 2007/044616 A2 | 4/2007 |
| WO | WO 2009/039409 A1 | 3/2009 |
| WO | WO 2009/134870 A1 | 11/2009 |
| WO | WO 2012/075324 A1 | 6/2012 |
| WO | WO 2013/050725 A1 | 4/2013 |
| WO | WO 2014/089354 A1 | 6/2014 |
| WO | WO 2014/194100 A1 | 12/2014 |

OTHER PUBLICATIONS

U.S. Office Action dated Jun. 14, 2012 issued in U.S. Appl. No. 12/678,981.
U.S. Final Office Action dated Mar. 26, 2013 issued in U.S. Appl. No. 12/678,981.
U.S. Office Action dated Jun. 17, 2014 issued in U.S. Appl. No. 12/678,981.
US Ex Parte Quayle Action dated Mar. 3, 2015 issued in U.S. Appl. No. 12/678,981.
U.S. Notice of Allowance dated May 14, 2015 issued in U.S. Appl. No. 12/678,981.
U.S. Office Action dated Feb. 1, 2011 issued in U.S. Appl. No. 12/650,329.
U.S. Office Action dated Aug. 8, 2011 issued in U.S. Appl. No. 12/650,329.
U.S. Final Office Action dated Apr. 30, 2012 issued in U.S. Appl. No. 12/650,329.
U.S. Notice of Allowance dated Jun. 18, 2012 issued in U.S. Appl. No. 12/650,329.
U.S. Office Action dated Jul. 6, 2012 issued in U.S. Appl. No. 12/985,122.
U.S. Final Office Action dated Apr. 2, 2013 issued in U.S. Appl. No. 12/985,122.
U.S. Notice of Allowance dated Aug. 9, 2013 issued in U.S. Appl. No. 12/985,122.
U.S. Office Action dated Mar. 19, 2015 issued in U.S. Appl. No. 14/015,838.
U.S. Final Office Action dated Dec. 18, 2015 issued in U.S. Appl. No. 14/015,838.
U.S. Notice of Allowance dated Aug. 24, 2016 issued in U.S. Appl. No. 14/015,838.
PCT International Search Report and Written Opinion dated Mar. 18, 2014 issued in PCT/US2013/073410.
PCT International Preliminary Report on Patentability and Written Opinion dated Jun. 18, 2015 issued in PCT/US2013/073410.
PCT International Search Report and Written Opinion dated Jan. 12, 2009 issued in PCT/US08/77074 (WO2009/039409).
PCT International Preliminary Report on Patentability dated Mar. 24, 2010 issued in PCT/US08/77074 (WO2009/039409).
PCT International Search Report and Written Opinion dated Oct. 1, 2014 issued in PCT/US2014/040036.
PCT International Report on Patentability and Written Opinion dated Dec. 10, 2015 issued in PCT/US2014/040036.
Australian Office Action dated Feb. 26, 2013 issued in 2008302111.
Canadian Examiner's Report dated Feb. 4, 2015 issued in 2,699,944.
Canadian Examiner's Report dated Mar. 10, 2016 issued in 2,699,944.
Canadian Examiner's Report dated Nov. 22, 2016 issued in 2,699,944.
Chinese First Office Action dated May 2, 2012 issued in CN200880117225.8.
Chinese Second Office Action dated Feb. 4, 2013 issued in CN200880117225.8.
Chinese Third Office Action dated Jul. 15, 2013 issued in CN200880117225.8.
Chinese Final Rejection dated Jan. 6, 2014 issued in CN200880117225.8.
Chinese First Office Action dated Jul. 17, 2015 issued in CN201410160383.9.
Chinese Second Office Action dated Jun. 6, 2016 issued in CN201410160383.9.
Chinese Third Office Action dated Feb. 16, 2017 issued in CN201410160383.9.
European Extended Search Report dated Apr. 26, 2012 issued in EP08831632.8.
European Office Action dated Feb. 8, 2013 issued in EP08831632.8.
European Summons to attend Oral Proceedings dated Oct. 14, 2013 issued in EP08831632.8.
European Response [EP Summons to attend Oral Proceedings dated Oct. 14, 2013] dated Jan. 7, 2014 for EP08831632.8.
European Findings upon submission relating to Oral Proceedings dated Jan. 13, 2014 issued in EP08831632.8.
European Brief Communication [regarding the Oral Proceedings of Mar. 13, 2014] dated Jan. 16, 2014 issued in EP08831632.8.
European Written Submission [response to Communication of Jan. 16, 2014] dated Jan. 29, 2014 issued in EP08831632.8.
European Findings upon submission relating to Oral Proceedings dated Feb. 10, 2014 issued in EP08831632.8.
European Notification relating to Oral Proceedings dated Feb. 13, 2014 issued in EP08831632.8.
European Communication regarding Intention to Grant dated Mar. 4, 2014 issued in EP08831632.8.
European Communication regarding Intention to Grant dated Oct. 2, 2014 issued in EP08831632.8.
European Communication regarding Decision to Grant dated Jan. 15, 2015 issued in EP08831632.8.
European Extended Search Report dated Feb. 26, 2015 issued in EP 14 180 412.0.
European Office Action dated Dec. 11, 2015 issued in EP 14 180 412.0.
European Reply to Communication from Examining Division dated Mar. 29, 2016 for EP 14 180 412.0.
European Intention to Grant dated Jun. 24, 2016 issued in EP 14 180 412.0.
European Decision to Grant dated Nov. 10, 2016 issued in EP 14 180 412.0.
European Extended Search Report dated Feb. 24, 2017 issued in EP 16 19 5608.1.

(56) References Cited

OTHER PUBLICATIONS

Israeli Office Action dated Apr. 5, 2012 issued in IL-204644.
Israeli Office Action dated Apr. 17, 2013 issued in IL-204644.
Israeli Office Action dated Apr. 19, 2015 issued in IL-233305.
Israeli Office Action dated Nov. 24, 2016 issued in IL-233305.
Indian Office Action dated Dec. 30, 2016 issued in IN-1404/KOLNP/2010.
Japanese Office Action dated Jan. 29, 2013 issued in JP 2010-526011.
Japanese Final Office Action dated Mar. 10, 2014 issued in JP 2010-526011.
Japanese First Office Action dated Jul. 6, 2015 issued in JP 2014-154820.
Japanese Second Office Action dated Jul. 4, 2016 issued in JP 2014-154820.
Japanese Notice of Allowance [No Translation] dated Jan. 4, 2017 issued in JP 2014-154820.
Korean Office Action dated Mar. 27, 2015 issued in KR 2010-7008737.
Korean Final Rejection dated Feb. 25, 2016 issued in KR 2010-7008737.
Korean Office Action dated Jun. 21, 2016 issued in KR 2016-7014105.
Mexican Office Action [No translation] dated May 7, 2013 issued in MX/a/2010/003099.
Mexican Office Action [No translation] dated Feb. 12, 2014 issued in MX/a/2010/003099.
Mexican Office Action [brief description in English] dated Apr. 25, 2016 issued in MX/a/2014/010567.
Mexican Second Office Action [No translation] dated Nov. 10, 2016 issued in MX/a/2014/010567.
NCBI, GenBank accession No. CAP17327.1, "interferon gamma [*Homo sapiens*]", (Oct. 15, 2008), 2pp.
Alfthan et al. (1995) "Properties of a single-chain antibody containing different linker peptides," *Protein Engineering* 8(7):725-731.
Arai et al. (Aug. 2001) "Design of the linkers which effectively separate domains of a bifunctional fusion protein," *Protein Engineering*, 14(8):529-532.
Bai et al. (Sep. 2006) "Improving the oral efficacy of recombinant granulocyte colony stimulating factor and transferrin fusion protein by spacer optimization," *Pharmaceutical Research*, 23(9):2116-2121.
Berger et al. (2002) "Licensure of Gemtuzumab Ozogamicin for the Treatment of Selected Patients 60 Years of Age or Older with Acute Myeloid Leukemia in First Relapse," *Invest. New Drugs*, 20(4):395-406.
Bird et al. (1988) "Single-Chain Antigen-Binding Proteins," *Science*, 242:423-426.
Bosly et al. (2004) "Role of anti-CD20 monoclonal antibody in association with immunomodulatory agents," *Pathologic Biologie* 52:39-42 [English Abstract Only].
Cheng et al. (2008) "Antibody-fused interferons as an effective approach to enhance target specificity and antiviral efficacy of type I interferons," *Cell Research* 18:1230-1232.
Curtis et al. (1991) "Enhanced hematopoietic activity of a human granulocyte/macrophage colony-stimulating factor-interleukin 3 fusion protein," *Proc. Natl. Acad. Sci. USA*, 88:5809-5813.
Dela Cruz et al. (2004) "Antibody-cytokine fusion proteins: innovative weapons in the war against cancer," *Clin Exp Med*, 4:57-64.
Ebbinghaus et al. (2004) "An Antibody-Interferon Gamma Fusion Protein for Cancer Therapy," *A dissertation submitted to the Swiss Federal Institute of Technology Zurich for the degree of Doctor of Natural Sciences* pp. 1-137.
Ebbinghaus et al. (2005) "Engineered vascular-targeting antibody-interferon-γ fusion protein for cancer therapy," *Int. J Cancer*, 116(2):304-313.
Field-Smith et al. (2006) "Bortezomib (Velcade™) in the treatment of multiple myeloma," *Therapeutics and Clinical Risk Management*, 2(3):271-279.

Flannery et al. (1984) "Immunomodulation: NK cells activated by interferon-conjugated monoclonal antibody against human osteosarcoma," *Eur J Cancer Clin Oncol.*, 20(6):791-798.
Frey et al. (2011) "Antibody-Based Targeting of Tumor Vasculature and Stroma," *The Tumor Microenvironment 4* Part VI Chapter 22:419-450.
Frey et al. (2011) "Antibody-based targeting of interferon-alpha to the tumor neovasculature: a critical evaluation," *Integr. Biol.*, 3:468-478.
Goldstein et al. (1988) "The role of interferon in cancer therapy: A current perspective," *CA Cancer J. Clin.*, 38(5):258-277.
Helguera et al. (2006) "Cytokines fused to antibodies and their combinations as therapeutic agents against different peritoneal HER2/neu expressing tumors," *Molecular Cancer Therapeutics, American Association of Cancer Research*, 5(4): 1029-1040.
Heuser et al. (2003) "ANTI-CD30-IL-12 Antibody-Cytokine Fusion Protein That Induces IFN-Γ Secretion of T Cells and NK Cell-Mediated Lysis of Hodgkin's Lymphoma-Derived Tumor Cells," *Int. J. Cancer*, 106:545-552.
Huang et al. (2006) "Fusion of anti-HER2/ neu with inflammatory cytokines IFN-alpha and TNF-alpha results in molecules that elicit an anti-tumor response or potentiate wound healing," *Dissertation*, pp. 1-120 XP009158273.
Huang et al. (2007) "Targeting IFN-α to B cell lymphoma by a tumor-specific antibody elicits potent antitumor activities," *Journal of Immunology*, 179(10):6881-6888.
Huston et al. (1988) "Protein engineering of antibody binding sites: Recovery of specific activity in an anti-digoxin single-chain Fv analogue produced in *Escherichia coli*," *Proc. Natl. Acad. Sci.*, 85:5879-5883.
Jain et al. (2007) "Engineering antibodies for clinical applications," *Trends in Biotechnology*, 25(7):307-316.
Kaspar et al. (2007) "The Antibody-Mediated Targeted Delivery of Interleukin-15 and GM-CSF to the Tumor Neovasculature Inhibits Tumor Growth and Metastasis," *Cancer Res*, 67(10):4940-4948.
Klimka et al. (2003) "Construction of proteolysis resistant human interleukin-2 by fusion to its protective single chain antibody," *Cytokine*, 22:134-141.
McCarron et al. (2005) "Antibody Conjugates and Therapeutic Strategies," *Molecular Interventions*, 5(6):368-380.
Marshall et al. (2001) "Engineering and Characterization of a Novel Fusion Protein Incorporating B7.2 and an Anti-ErbB-2 Single-Chain Antibody Fragment for the Activation of Jurkat T Cells," *J. Immunotherapy*, 24(1):27-36.
Mickle, John E.; Ph.D. et al. (2000) "Genotype-Phenotype Relationships in Cystic Fibrosis," *Med. Clin. N. America*, 84(3):597-607.
Mizokami et al. (2003) "Chimeric TNT-3 Antibody/Murine Interferon-γ Fusion Protein for the Immunotherapy of Solid Malignancies," *Hybridoma and Hybridomics*, 22(4): 197-207.
Ozzello et al. (1998) "Conjugation of interferon alpha to a humanized monoclonal antibody (HuBrE-3v1) enhances the selective localization and antitumor effects of interferon in breast cancer xenografts," *Breast Cancer Res Treat.*, 48(2):135-47.
Peng et al. (1999) "A Single-Chain IL-12 IgG3 Antibody Fusion Protein Retains Antibody Specificity and IL-12 Bioactivity and Demonstrates Antitumor Activity," *J. Immunol.*, 163:250-258.
Portlock et al. (2006) "Pegylated interferon plus rituximab in advanced stage, indolent lymphoma: is there CD20 antigen upregulation?" *Leukemia & Lymphoma*, 47(7): 1260-1264.
Rossi et al. (2009) "CD20-targeted tetrameric interferon-, a novel and potent immunocytokine for the therapy of B-cell lymphomas," *Blood*, 114:3864-3871.
Rossi et al. (2010) "A Bispecific Antibody-IFNα2b Immunocytokine Targeting CD20 and HLA-DR is Highly Toxic to Human Lymphoma and Multiple Myeloma Cells," *Cancer Res.*, 70:7600-7609.
Scharma et al. (2006) "Antibody targeted drugs as cancer therapeutics," *Nature Reviews Drug Discovery*, 5:147-159.
Seyfried et al. (2008) "Up-regulation of NG2 proteoglycan and interferon induced transmembrane proteins 1 and 3 in mouse astrocytoma: A membrane proteomics approach," *Cancer Letters*, 263(2):243-252.

(56) References Cited

OTHER PUBLICATIONS

Song et al. (2007) "Construction of Expression Vector of Anti-HBsAg dsFv and Alpha-IFN Fusion Gene," *Chinese Journal of Public Health*, 23(9):1096-1099 [English Abstract].
Takaoka et al. (Jul. 31, 2003) "Integration of interferon-α/β signalling to p53 responses in tumour suppression and antiviral defence," *Nature*, 424(6948):516-523.
von Gabain, A., et al. (1990) "Three human interferon-α2 subvariants disclose structural and functional differences," *Eur. J Biochem.*, 190:257-261.
Wei et al. (1998) "Clone and expression of a fusion protein consisting of anti-HBsAg Fab fragment and interferon-α in *E.coli*," *Chinese Journal of Hepatology*, 6(4):229-231 [Abstract Only].
Wells, J.A., (Sep. 18, 1990) "Additivity of Mutational Effects in Proteins," *Biochemistry*, 29(37):8509-8517.
Xuan et al. (2010) "Targeted delivery of interferon-alpha via fusion to anti-CD20 results in potent antitumor activity against B-cell lymphoma," *Blood*, 115(14):2864-2871.
Yoo et al. (Dec. 11, 2012) Anti-CD138-IFNα Fusion Proteins are Effective in Treating Multiple Myeloma, In: *54th American Society of Hematology Annual Meeting and Exposition*, Atlanta, GA, Abstract No. 939, 1 page.
Zaidi et al. (2011) "The two faces of interferon-gamma in cancer," *Clin. Cancer Res.*, 17(19):1-7.
Zheng et al. (1998) "The Construction and Expression of a Fusion Protein Consisting of anti-HBsAg Antibody Fragment Fab and interferon—αA in *E.coli*," *Chinese Journal of Hepatology*, 6(4):229-231 [English Abstract Only].
U.S. Office Action dated Oct. 2, 2017 issued in U.S. Appl. No. 15/359,456.
European Office Action dated Nov. 29, 2017 issued in EP 16 19 5608.1.
Indian Office Action (Hearing Notice) dated Nov. 29, 2017 issued in IN-1404/KOLNP/2010.
Japanese First Office Action dated Jul. 31, 2017 issued in JP 2016-215048.
Ozzello et al.(1993) "The use of natural interferon alpha conjugated to a monoclonal antibody anti mammary epithelial mucin (Mc5) for the treatment of human breast cancer xenografts," *Breast Cancer Res Treat.*, 25(3):265-276.
Pallela et al. (2000) "Interferon-α-2b immunoconjugate for improving immunoscintigraphy and immunotherapy," *The Journal of Nuclear Medicine*, 41(6): 1108-1113.
Thakur et al. (1997) "Improved antibody targeting with interferon-α-2b conjugate," *Journal of Immunotherapy*, 20(3): 194-201.
Theofilopoulos et al. (2014) "Type I interferons (alpha/beta) in immunity and autoimmunity." *Annual Reviews of Immunology*, 23: 307-336.

* cited by examiner

```
                                            <---------------------------------------- FR1 - IMGT
                              1           5              10              15
                              Q  V  K  L  Q  Q  S  G  G        G  L  V  Q  P
MAA_Vh                        caa gtc aaa ctg cag cag agc ggt gga ... ggc ctg gtg cag cct
                                 E        E  E
AJ972404 Musmus IGHV6-6*02 F  g-- --g --g --t g-- g-- tct --a ---  ... --- t-- --- --a ---
                              -------------------------------------> -----------------------
                                            20             25              30
                              G  G  S  M  K  L  S  C  V  V  S  G  F  T  F
MAA_Vh                        ggt ggc agc atg aag ctg agc tgc gtc gtg agc ggc ttc acc ttc
AJ972404 Musmus IGHV6-6*02 F  --a --a tc- --- --a --c tc- --t t-- -cc tct --a --- --t ---
                              _ CDR1 - IMGT _____              <---------------------------
                                           35              40              45
                                                 S  N  Y  W  M  N  W  V  R  Q  S
MAA_Vh                        ... ... ... ... agc aac tac tgg atg aac tgg gtc cgg cag agc
AJ972404 Musmus IGHV6-6*02 F  ... ... ... ... --t --- --- --- --- --- --- --- --c --- tct
                              FR2 - IMGT --------------------->           _____ CDR2
                                           50              55              60
                              P  E  K  G  L  E  W  I  A  E  I  R  L  K  S
MAA_Vh                        ccc gag aag ggc ctg gaa tgg atc gcc gag atc cgg ctg aaa agc
                                                          V        A
AJ972404 Musmus IGHV6-6*02 F  --a --- --- --g --t --g --- g-t --t --a --t a-a t-- --- tct
                              _ IMGT _____             <-----------------------------------
                                           65              70              75
                              N  N  F  G  R  Y  Y  A  E  S  V  K     G  R
MAA_Vh                        aac aac ttc ggc cgg tac tac gcc gag agc gtg aag ... ggc cgg
                                        Y  A  T  H
AJ972404 Musmus IGHV6-6*02 F  --t --t -at -ca aca c-t --t --g --- tct --- --a ... --g a--
                              ------------------------------- FR3 - IMGT ----------------
                                           80              85              90
                              F  T  I  S  R  D  D  S  K  S  S  A  Y  L  Q
MAA_Vh                        ttc acc atc agc cgg gac gac agc aag agc agc gcc tac ctg cag
AJ972404 Musmus IGHV6-6*02 F  --- --- --- tca a-a --t --t tc- --a --t t-- --- --- --- --a
                              ---------------------------------------------------------->
                                           95              100             104
                              M  I  N  L  R  A  E  D  T  G  I  Y  Y  C  T
MAA_Vh                        atg atc aac ctg cgg gcc gag gac acc ggc atc tac tac tgc acc
                                     N
AJ972404 Musmus IGHV6-6*02 F  --- -a- --- t-a a-a --t --a --- --t --- --t --t --- --t ---
                              _____ CDR3 - IMGT _____
                              S  Y  G  N  Y  V  G  H  Y  F  D  H  W  G  Q
MAA_Vh                        agc tac ggc aac tac gtg ggc cac tac ttc gac cac tgg ggc cag
                              R
AJ972404 Musmus IGHV6-6*02 F  --g MAA_Vh                        G  T  T  V  T  V  S  S
                              ggc acc acc gtg act gtc agc agc g
```

*Fig. 1A*

```
                              <---------------------------- FR1 - IMGT
                              1         5              10             15
                              D   I   E   L   T   Q   S   P   K   F   M   S   T   S   V
MAA_Vk                        gac atc gag ctg acc cag agc ccc aag ttc atg agc acc agc gtg
Y15976 Musmus IGKV6-15*01 F   --- --t -t- a-- --- --- tct -aa --a --- --- tc- --a tca --a
                              ------------------------------------------------------->
                                              20                  25                  30
                              C   D   R   V   S   V   T   C   K   A   S   Q   N   V
MAA_Vk                        ggc gac aga gtg tcc gtg acc tgc aag gcc agc cag aac gtg ...
Y15976 Musmus IGKV6-15*01 F   --a --- --g --c ag- --c --- --- --- --- --t --- --t --- ...
                              _ CDR1 - IMGT _____ <------------------------
                                                  35                  40                  45
                                                  D   T   N   V   A   W   Y   Q   Q   K
MAA_Vk                        ... ... ... ... ... gac acc aac gtg gcc tgg tat cag cag aag
                                                              G
Y15976 Musmus IGKV6-15*01 F   ... ... ... ... ... --gt --t --a --- --- --- --a --- --a
                              FR2 - IMGT -------------------->  _____ CDR2
                                          50                  55                  60
                              P   G   Q   S   P   E   P   L   L   F   S   A
MAA_Vk                        ccc ggc cag agc cct gag cct ctg ctg ttc agc gcc ... ... ...
                                                          K       A       I   Y
Y15976 Musmus IGKV6-15*01 F   --a --g --a tct --- a-a g-a --- a-t -a- tcg --a ... ... ...
                              - IMGT _____ <-----------------------
                                          65                  70                  75
                                          S   Y   R   Y   T   G   V   P   D   R
MAA_Vk                        ... ... ... ... agc tac aga tac acc ggc gtg ccc ... gac aga
                                                              S
Y15976 Musmus IGKV6-15*01 F   ... ... ... ... tc- --- c-g --- -gt --a --c --t ... --t c-c
                              ---------------------------- FR3 - IMGT ----------------
                                          80                  85                  90
                              F   T   G   S   G       S   G   T   D   F   T   L   T
MAA_Vk                        ttc aca ggc agc ggc ... ... tcc ggc acc gac ttc acc ctg acc
Y15976 Musmus IGKV6-15*01 F   --- --- --- --t --a ... ... --t --q --a --t --- --t --c
                              ------------------------------------------------------->
                                          95                  100                 104
                              I   S   N   V   Q   S   E   D   L   A   E   Y   F   C   Q
MAA_Vk                        atc agc aac gtg cag agc gag gac ctg gcc gag tac ttc tgc cag
Y15976 Musmus IGKV6-15*01 F   --- --- --t --- --- tct --a --- t-- --a --- --t --- --t ---
                              _____ CDR3 - IMGT _____
                              Q   Y   N   S   Y   P   L   T   F   G   G   G   T   K   L
MAA_Vk                        cag tac aac agc tac ccc ctg acc ttc ggc gga ggc acc aag ctg
Y15976 Musmus IGKV6-15*01 F   --a --t --- --- --t --t --
                              E   I   K
MAA_Vk                        gaa atc aag c
Y15976 Musmus IGKV6-15*01 F
```

*Fig. 1B*

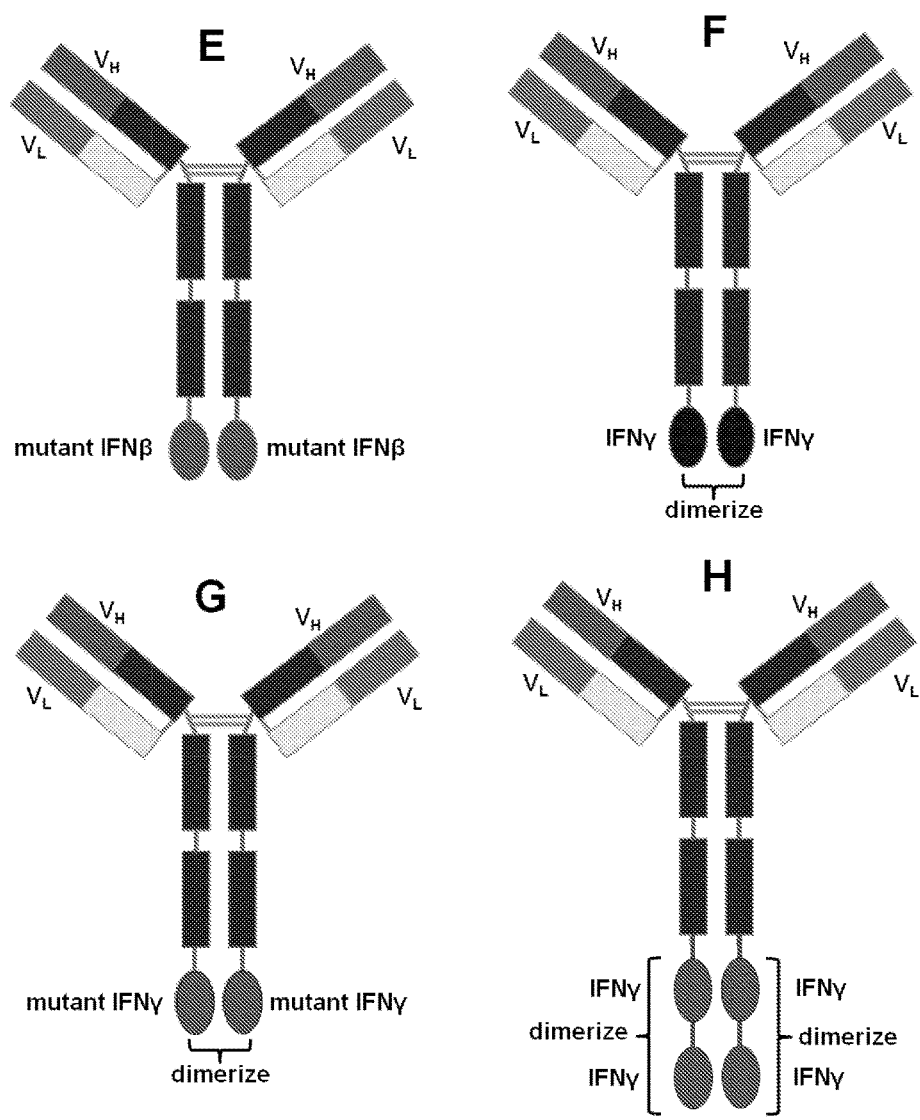
Fig. 2, cont'd.

ANTI-CSPG4 FUSIONS WITH INTERFERON FOR THE TREATMENT OF MALIGNANCY

CROSS-REFERENCE TO RELATED APPLICATIONS

This application is a U.S. 371 National Phase of PCT/US2014/040036, filed on May 29, 2014, which claims benefit of and priority to U.S. Ser. No. 61/828,590, filed on May 29, 2013, all of which are incorporated herein by reference in their entirety for all purposes.

STATEMENT OF GOVERNMENTAL SUPPORT

[Not Applicable]

BACKGROUND

Malignant melanoma is an immunogenic, highly aggressive and often lethal form of skin cancer. It is the most common cancer in the 17-34 years age group but affects people of all ages, and therefore has a significant socioeconomic impact for patients and their families. Although diagnosed skin lesions can be initially excised by surgical intervention, skin and distal metastases unfortunately occur in 20% of patients originally treated with local disease. Patients with lymph node and other distal metastases have dismal prognosis, and this is partly due to lack of effective treatments for this cohort.

Melanoma has presented major challenges to numerous targeted therapy efforts and therefore effective treatments are urgently needed for patients with this disease. The recent approval of the monoclonal antibody ipilimumab (targeting the CTLA4 blockade to enhance T cell activation) for the treatment of melanoma lends merit to the notion that activating immune responses with antibodies may have therapeutic significance and has renewed interest in the field of antibody therapies for the treatment of challenging tumours such as melanoma.

Interferons have been contemplated for use in the treatment of cancer (Borden et al. (2005) *J. Interferon Cytokine Res.* 25: 511-527; Borden et al. (2007) *Nat. Rev. Drug Discov.* 6: 975-690). There are seven classes of type I IFNs with IFNα and IFNβ being the most abundant. Both IFNα and IFNβ bind to the same receptor composed of two transmembrane proteins, IFNAR 1 and 2, but IFNβ binds with much higher affinity than IFNα (Lamken et al. (2004) *J. Mol. Biol.* 341: 303-318). IFNs have been shown to have anti-proliferative activity as well as the ability to induce apoptosis in hematological malignancies and solid tumors in addition to their anti-viral activity (as reviewed in Borden et al. (2007) *Nat. Rev. Drug Discov.* 6: 975-690). However, the effectiveness of IFNα for cancer therapy is overshadowed by side effects when used at high doses (Weiss (1998) *Semin. Oncol.* 25: 9-13) and by a short half-life, e.g., of only 1 hour (Peleg-Shulman et al. (2004) *J. Med. Chem.* 47: 4897-4904). Strategies to increase the half-life have included the covalent linkage of polyethylene glycols (PEG) to IFNα (Talpaz et al. (2001) *Blood,* 98: 1708-1713), but such modifications have resulted in lower activity (Rosendahl et al. (2005) *Bioconjug. Chem.* 16: 200-207).

SUMMARY

In various embodiments this invention pertains to the discovery that attaching an interferon to a targeting moiety (e.g., a molecule that specifically and/or preferentially binds a marker on or associated with a cell) substantially improves the therapeutic efficacy of the interferon and appears to reduce systemic toxicity. Accordingly, in various embodiments, this invention provides constructs comprising an interferon attached to a targeting moiety and uses of such constructs to specifically and/or preferentially inhibit the growth or proliferation or even to kill certain target cells (e.g., cancer cells). In certain embodiments the constructs comprise a mutant interferon, e.g., a mutant IFNα with higher affinity for the IFNAR to enhance the potency of the construct.

Accordingly, in certain embodiments, a chimeric construct is provided where the construct comprises an interferon (e.g., interferon-alpha, interferon-beta, interferon-gamma, mutant interferon-α, mutant interferon-β, and the like) attached to a targeting moiety that binds to a tumor associated antigen, in particular CSPG4. The construct when contacted to a tumor cell results in the killing or inhibition of growth or proliferation of the tumor cell.

In various aspects, the invention(s) contemplated herein may include, but need not be limited to, any one or more of the following embodiments

Embodiment 1

A chimeric construct including an interferon attached to an antibody that binds chondroitin sulfate proteoglycan 4 (CSPG4).

Embodiment 2

The construct of embodiment 1, wherein said construct when contacted to a cell that expresses or overexpresses CSPG4 cell results in the killing or inhibition of growth or proliferation of said cell.

Embodiment 3

The construct of embodiment 2, wherein said cell that expresses or overexpresses CSPG4 is a cancer cell.

Embodiment 4

The construct of embodiment 2, wherein said cell that expresses or overexpresses CSPG4 is a cancer selected from the group consisting of tumors of neuroectodermal origin including melanoma and glioma, breast cancer including triple negative breast cancer, squamonous cell carcinoma of head and neck, myeloid leukemia, pancreatic carcinoma, chondrosarcoma, chordoma, mesothelioma, renal cell carcinoma, lung carcinoma, ovarian carcinoma and cancer stem cells representing various histologies.

Embodiment 5

The construct of embodiment 2, wherein said cell that expresses or overexpresses CSPG4 is a cancer stem cell.

Embodiment 6

The construct according to any one of embodiments 1-5, wherein said interferon is a type I interferon.

Embodiment 7

The construct of embodiment 6, wherein said interferon is an interferon-alpha (IFNα).

Embodiment 8

The construct of embodiment 6, wherein said interferon is an IFN-α2.

Embodiment 9

The construct of embodiment 6, wherein said interferon is an IFN-α10.

Embodiment 10

The construct of embodiment 6, wherein said interferon is an IFN-α14.

Embodiment 11

The construct of embodiment 6, wherein said interferon is an interferon-beta (IFNβ).

Embodiment 12

The construct according to any one of embodiments 1-5, wherein said interferon is a type II interferon (IFNγ).

Embodiment 13

The construct of embodiment 12, wherein said interferon gamma is a full-length interferon gamma.

Embodiment 14

The construct of embodiment 12, wherein said interferon gamma is a truncated interferon gamma.

Embodiment 15

The construct of embodiment 12, wherein said interferon gamma is an interferon gamma having 1-15 amino acids truncated from the carboxyl terminus and/or 1-3 amino acids truncated from the amino terminus.

Embodiment 16

The construct of embodiment 12, wherein said interferon gamma is a truncated interferon gamma where the amino acid sequence of said truncated interferon gamma consists of the sequence DPYVKEAE NLKKYFNAGH SDVADNGTLF LGILKNWKEE SDRKIMQSQI VSFY-FKLFKN FKDDQSIQKS VETIKEDMNV KFFNSNK-KKR DDFEKLTNYS VTDLNVQRKA IHELIQVMAE LSPAAKTGKR KRSQM (SEQ ID NO:29).

Embodiment 17

The construct according to any one of embodiments 1-16, wherein said interferon is a human interferon.

Embodiment 18

The construct according to any one of embodiments 1-16, wherein said interferon is a non-human interferon.

Embodiment 19

The construct of embodiment 18, wherein said interferon is a murine interferon.

Embodiment 20

The construct according to any one of embodiments 1-5, wherein said interferon is a mutant interferon gamma.

Embodiment 21

The construct according to any one of embodiments 1-5, wherein said interferon is a mutant type I interferon.

Embodiment 22

The construct of embodiment 21, wherein said interferon is a mutant interferon-alpha.

Embodiment 23

The construct of embodiment 21, wherein said interferon is a mutant interferon-alpha having lower activity than native interferon alpha.

Embodiment 24

The construct of embodiment 21, wherein said interferon is a mutant interferon-alpha having higher activity than native interferon alpha.

Embodiment 25

The construct of embodiment 21, wherein said interferon is a mutant human interferonα-2 having mutations at one or more sites selected from the group consisting of His57, Glu58, and Gln61.

Embodiment 26

The construct of embodiment 25, wherein said interferon is an interferonα-2 having a mutation at His57.

Embodiment 27

The construct of embodiment 26, wherein said mutation at His57 is a mutation to an amino acid selected from the group consisting of A, Y, and M.

Embodiment 28

The construct according to any one of embodiments 25-27, wherein said interferon is an interferon α-2 having a mutation at Glu58.

Embodiment 29

The construct of embodiment 28, wherein said mutation at Glu58 is a mutation to an amino acid selected from the group consisting of A, N, D, and L.

Embodiment 30

The construct according to any one of embodiments 25-29, wherein said interferon is an interferonα-2 having a mutation at Gln61.

Embodiment 31

The construct of embodiment 30, wherein said mutation at Gln61 is a mutation to an amino acid selected from the group consisting of A, S, and D.

Embodiment 32

The construct of embodiment 25, wherein said interferon includes the mutations H57Y, E58N, and Q61S.

Embodiment 33

The construct of embodiment 25, wherein said interferon includes the mutations H57M, E58L, and Q61D.

Embodiment 34

The construct of embodiment 25, wherein said interferon includes the mutations H57Y, E58L, and Q61D.

Embodiment 35

The construct of embodiment 25, wherein said interferon includes the mutations H57Y, E58A, and Q61S.

Embodiment 36

The construct of embodiment 25, wherein said interferon includes the mutations H57A, E58A, and Q61A.

Embodiment 37

The construct according to any one of embodiments 1-36, wherein said antibody binds to a CSPG4 at an epitope bound by one or more antibodies selected from the group consisting of 9.2.27, VF1-TP34, VF1-TP34, VF1-TP41.2, TP61.5, 149.53, 149.53, 225.28, 225.28s, 763.74, and scFv-FcC21.

Embodiment 38

The construct of embodiment 37, wherein said antibody includes at least 3 complementarity determining regions from the VH domain of an antibody selected from the group consisting of 9.2.27, VF1-TP34, VF1-TP34, VF1-TP41.2, TP61.5, 149.53, 149.53, 225.28, 225.28s, 763.74, and scFv-FcC21.

Embodiment 39

The construct of embodiment 37, wherein said antibody includes at least 3 complementarity determining regions from the VH domain of the 92.2.27 antibody.

Embodiment 40

The construct of embodiment 37, wherein said antibody includes at least 3 complementarity determining regions from the VH domain of the 225.28 antibody.

Embodiment 41

The construct of embodiment 37, wherein said antibody includes at least 3 complementarity determining regions from the VH domain of the scFv-FcC21 antibody.

Embodiment 42

The construct of embodiment 37, wherein said antibody includes at least 3 complementarity determining regions from the VH domain of the VF1-TP34 antibody.

Embodiment 43

The construct of embodiment 37, wherein said antibody includes at least 3 complementarity determining regions from the VH domain of the VF1-TP34 antibody.

Embodiment 44

The construct of embodiment 37, wherein said antibody includes at least 3 complementarity determining regions from the VH domain of the VF1-TP41.2 antibody.

Embodiment 45

The construct of embodiment 37, wherein said antibody includes at least 3 complementarity determining regions from the VH domain of the TP61.5 antibody.

Embodiment 46

The construct of embodiment 37, wherein said antibody includes at least 3 complementarity determining regions from the VH domain of the 149.53 antibody.

Embodiment 47

The construct of embodiment 37, wherein said antibody includes at least 3 complementarity determining regions from the VH domain of the 149.53 antibody.

Embodiment 48

The construct of embodiment 37, wherein said antibody includes at least 3 complementarity determining regions from the VH domain of the 225.28s antibody.

Embodiment 49

The construct of embodiment 37, wherein said antibody includes at least 3 complementarity determining regions from the VH domain of the 763.74 antibody.

Embodiment 50

The construct according to any one of embodiments 37-49, wherein said antibody includes at least 3 complementarity determining regions from the VL domain of an antibody selected from the group consisting of VF1-TP34, VF1-TP34, VF1-TP41.2, TP61.5, 9.2.27, 149.53, 149.53, 225.28, 225.28s, 763.74, and scFv-FcC21.

Embodiment 51

The construct of embodiment 50, wherein said antibody includes at least 3 complementarity determining regions from the VL domain of the 92.2.27 antibody.

Embodiment 52

The construct of embodiment 50, wherein said antibody includes at least 3 complementarity determining regions from the VL domain of the 225.28 antibody.

Embodiment 53

The construct of embodiment 50, wherein said antibody includes at least 3 complementarity determining regions from the VL domain of the scFv-FcC21 antibody.

Embodiment 54

The construct of embodiment 50, wherein said antibody includes at least 3 complementarity determining regions from the VL domain of the VF1-TP34 antibody.

Embodiment 55

The construct of embodiment 50, wherein said antibody includes at least 3 complementarity determining regions from the VL domain of the VF1-TP34 antibody.

Embodiment 56

The construct of embodiment 50, wherein said antibody includes at least 3 complementarity determining regions from the VL domain of the VF1-TP41.2 antibody.

Embodiment 57

The construct of embodiment 50, wherein said antibody includes at least 3 complementarity determining regions from the VL domain of the TP61.5 antibody.

Embodiment 58

The construct of embodiment 50, wherein said antibody includes at least 3 complementarity determining regions from the VL domain of the 149.53 antibody.

Embodiment 59

The construct of embodiment 50, wherein said antibody includes at least 3 complementarity determining regions from the VL domain of the 149.53 antibody.

Embodiment 60

The construct of embodiment 50, wherein said antibody includes at least 3 complementarity determining regions from the VL domain of the 225.28s antibody.

Embodiment 61

The construct of embodiment 50, wherein said antibody includes at least 3 complementarity determining regions from the VL domain of the 763.74 antibody.

Embodiment 62

The construct of embodiment 37, wherein said antibody includes the VH and/or VL domain of an antibody selected from the group consisting of VF1-TP34, VF1-TP34, VF1-TP41.2, TP61.5, 9.2.27, 149.53, 149.53, 225.28, 225.28s, 763.74, and scFv-FcC21.

Embodiment 63

The construct of embodiment 62, wherein said antibody includes the VH and the VL domain of an antibody selected from the group consisting of VF1-TP34, VF1-TP34, VF1-TP41.2, TP61.5, 9.2.27, 149.53, 149.53, 225.28, 225.28s, 763.74, and scFv-FcC21.

Embodiment 64

The construct of embodiment 63, wherein said antibody includes the VH and the VL domain of the 92.2.27 antibody.

Embodiment 65

The construct of embodiment 63, wherein said antibody includes the VH and the VL domain of the 225.28 antibody.

Embodiment 66

The construct of embodiment 63, wherein said antibody includes the VH and the VL domain of the scFv-FcC21 antibody.

Embodiment 67

The construct of embodiment 63, wherein said antibody includes the VH and the VL domain of the VF1-TP34 antibody.

Embodiment 68

The construct of embodiment 63, wherein said antibody includes the VH and the VL domain of the VF1-TP34 antibody.

Embodiment 69

The construct of embodiment 63, wherein said antibody includes the VH and the VL domain of the VF1-TP41.2 antibody.

Embodiment 70

The construct of embodiment 63, wherein said antibody includes the VH and the VL domain of the TP61.5 antibody.

Embodiment 71

The construct of embodiment 63, wherein said antibody includes the VH and the VL domain of the 149.53 antibody.

Embodiment 72

The construct of embodiment 63, wherein said antibody includes the VH and the VL domain of the 149.53 antibody.

Embodiment 73

The construct of embodiment 63, wherein said antibody includes the VH and the VL domain of the 225.28s antibody.

Embodiment 74

The construct of embodiment 63, wherein said antibody includes the VH and the VL domain of the 763.74 antibody.

Embodiment 75

The construct of embodiment 37, wherein said antibody is the 9.2.27 antibody.

Embodiment 76

The construct of embodiment 37, wherein said antibody is the VF1-TP34 antibody.

Embodiment 77

The construct of embodiment 37, wherein said antibody is the VF1-TP41.2 antibody.

Embodiment 78

The construct of embodiment 37, wherein said antibody is the TP61.5 antibody.

Embodiment 79

The construct of embodiment 37, wherein said antibody is the 149.53 antibody.

Embodiment 80

The construct of embodiment 37, wherein said antibody is the 225.28 antibody.

Embodiment 81

The construct of embodiment 37, wherein said antibody is the 225.28s antibody.

Embodiment 82

The construct of embodiment 37, wherein said antibody is the 763.74 antibody.

Embodiment 83

The construct of embodiment 37, wherein said antibody is the scFv-FcC21 antibody.

Embodiment 84

The construct according to any one of embodiments 1-74, wherein said antibody is an antibody selected from the group consisting of a single chain Fv (scFv), a FAB, a (Fab')$_2$, an (scFv)$_2$, and a full immunoglobulin.

Embodiment 85

The construct of embodiment 84, wherein said antibody is an scFv.

Embodiment 86

The construct of embodiment 84, wherein said antibody is a full immunoglobulin.

Embodiment 87

The construct of embodiment 86, wherein said antibody is an IgE.

Embodiment 88

The construct of embodiment 86, wherein said antibody is an IgG.

Embodiment 89

The construct of embodiment 86, wherein said antibody is an IgA.

Embodiment 90

The construct of embodiment 86, wherein said antibody is an IgM.

Embodiment 91

The construct of embodiment 86, wherein said antibody is an IgD.

Embodiment 92

The construct according to any of embodiments 1-91, wherein said antibody is chemically coupled to said interferon.

Embodiment 93

The construct according to any of embodiments 1-91, wherein said antibody is directly joined to said interferon.

Embodiment 94

The construct according to any of embodiments 1-91, wherein said antibody is joined to said interferon with a peptide linker.

Embodiment 95

The construct of embodiment 94, wherein said peptide linker joins said interferon to the carboxyl terminus of the CH3 domain of said antibody.

Embodiment 96

The construct of embodiment 95, wherein said peptide linker joins the amino terminus of said interferon to the carboxyl terminus of the CH3 domain of said antibody.

Embodiment 97

The construct of embodiment 95, wherein said peptide linker joins the carboxyl terminus of said interferon to the carboxyl terminus of the CH3 domain of said antibody.

Embodiment 98

The construct according to any one of embodiments 94-97, wherein said peptide linker is proteolysis resistant.

Embodiment 99

The construct according to any one of embodiments 94-98, wherein said peptide linker is fewer than 15 amino acids in length.

Embodiment 100

The construct according to any one of embodiments 94-99, wherein said peptide linker is not (Gly$_4$Ser)$_3$.

Embodiment 101

The construct according to any one of embodiments 94-97, wherein the amino acid sequence of said peptide linker is selected from the group consisting of GGG, GGS, GGGGS (SEQ ID NO:31), SGGGS (SEQ ID NO:32), GGGGSGGGGS (SEQ ID NO:33), A EAAAK A (SEQ ID NO:34), A EAAAK EAAAK A (SEQ ID NO:35), A EAAAK EAAAK EAAAK A (SEQ ID NO:36), A EAAAK EAAAK EAAAK EAAAK A (SEQ ID NO:37), A EAAAK EAAAK EAAAK EAAAK EAAAK A (SEQ ID NO:38), AEAAAKEAAAKAG (SEQ ID NO:39), AEAAAKEAAAKAGS (SEQ ID NO:40), GGGGG (SEQ ID NO:41), GGAGG (SEQ ID NO:42), GGGGGGGG (SEQ ID NO:43), GAGAGAGAGA (SEQ ID NO:44), RPLSYR-PPFPFGFPSVRP (SEQ ID NO:45), YPRSIYIR-RRHPSPSLTT (SEQ ID NO:46), TPSHLSHILPSF-GLPTFN (SEQ ID NO:47), RPVSPFTFPRLSNSWLPA (SEQ ID NO:48), SPAAHFPRSIPRPGPIRT (SEQ ID NO:49), APGPSAPSHRSLPSRAFG (SEQ ID NO:50), PRNSIHFLHPLLVAPLGA (SEQ ID NO:51), MPSLSGV-LQVRYLSPPDL (SEQ ID NO:52), SPQYPSPLTLTLP-PHPSL (SEQ ID NO:53), NPSLNPPSYLHRAPSRIS (SEQ ID NO:54), LPWRTSLLPSLPLRRRP (SEQ ID NO:55), PPLFAKGPVGLLSRSFPP (SEQ ID NO:56), VPPAPVVS-LRSAHARPPY (SEQ ID NO:57), LRPTPPRVRSYTC-CPTP (SEQ ID NO:58), PNVAHVLPLL TVPWDNLR (SEQ ID NO:59), CNPLLPLCARSPAVRTFP (SEQ ID NO:60), LGTPTPTPTPTGEF (SEQ ID NO:61), EDF-TRGKL (SEQ ID NO:62), L EAAAR EAAAR EAAAR EAAAR (SEQ ID NO:63), L EAAAR EAAAR EAAAR (SEQ ID NO:64), L EAAAR EAAAR (SEQ ID NO:65), L EAAAR (SEQ ID NO:66), EAAAR EAAAR EAAAR EAAAR (SEQ ID NO:67), EAAAR EAAAR EAAAR (SEQ ID NO:68), EAAAR EAAAR (SEQ ID NO:69), EAAAR (SEQ ID NO:70), LTEEQQEGGG (SEQ ID NO:71), TEEQQEGGG (SEQ ID NO:72), LAKLKQKTE-QLQDRIAGGG (SEQ ID NO:73), LELKTPLGDT THTCPRCPEP KSCDTPPPCP RCPEPKSCDT PPPCPRC-PEP KSCDTPPPCP RCPGG (SEQ ID NO:74), and LEPKSSDKTHTSPPSPGG (SEQ ID NO:75).

Embodiment 102

The construct according to any one of embodiments 94-97, wherein the amino acid sequence of said peptide linker is selected from the group consisting of GGGGS, SGGGGS, AEAAAKEAAAKAG, and AEAAAKEAAAK-AGS.

Embodiment 103

The construct according to any one of embodiments 94-97, wherein the amino acid sequence of said peptide linker is SGGGGS.

Embodiment 104

The construct according to any one of embodiments 94-97, wherein the amino acid sequence of said peptide linker is LTEEQQEGGG (SEQ ID NO:69)

Embodiment 105

The construct according to any one of embodiments 94-97, wherein the amino acid sequence of said peptide linker is TEEQQEGGG (SEQ ID NO:70).

Embodiment 106

The construct according to any one of embodiments 94-97, wherein the amino acid sequence of said peptide linker is LAKLKQKTEQLQDRIAGGG (SEQ ID NO:71).

Embodiment 107

The construct according to any one of embodiments 94-97, wherein the amino acid sequence of said peptide linker is LELKTPLGDT THTCPRCPEP KSCDTPPPCP RCPEPKSCDT PPPCPRCPEP KSCDTPPPCP RCPGG (SEQ ID NO:72).

Embodiment 108

The construct according to any one of embodiments 94-97, wherein the amino acid sequence of said peptide linker is LEPKSSDKTHTSPPSPGG (SEQ ID NO:73).

Embodiment 109

The construct of embodiment 1, wherein said construct includes interferon alpha attached to the 92.2.27 monoclonal antibody by a linker where the amino acid sequence of said linker includes or consists of the sequence SGGGGS.

Embodiment 110

The construct of embodiment 109, wherein said interferon is attached to the end of CH3 by said linker.

Embodiment 111

The according to any one of embodiments 1-110, wherein said construct or a component thereof is a recombinantly expressed fusion protein.

Embodiment 112

A pharmaceutical formulation including a construct according to any of embodiments 1-111 in a pharmaceutically acceptable excipient.

Embodiment 113

The pharmaceutical formulation according to embodiment 112, wherein said formulation is a unit dosage formulation.

Embodiment 114

The pharmaceutical formulation according to embodiment 112, wherein said formulation is a formulated for parenteral administration.

Embodiment 115

The pharmaceutical formulation according to embodiment 112, wherein said formulation is a formulated for administration via a route selected from the group consisting of oral administration, intravenous administration, intramuscular administration, direct tumor administration, inhalation, rectal administration, vaginal administration, transdermal administration, and subcutaneous depot administration.

Embodiment 116

A method of inhibiting growth and/or proliferation of a cell that expresses or overexpresses CSPG4, said method including contacting said cell with a chimeric construct according to any of embodiments 1-111, or a formulation according to any one of embodiments 112-115 in an amount sufficient to inhibit growth or proliferation of said cell.

Embodiment 117

The method of embodiment 116, wherein said cell is a cancer cell.

Embodiment 118

The method of embodiment 117, wherein said cancer cell is a metastatic cell.

Embodiment 119

The method of embodiment 117, wherein said cancer cell is in a solid tumor.

Embodiment 120

The method of embodiment 117, wherein said cancer cell is cell produced by a cancer selected from the group consisting of tumors of neuroectodermal origin including melanoma and glioma, breast cancer including triple negative breast cancer, squamonous cell carcinoma of head and neck, myeloid leukemia, pancreatic carcinoma, chondrosarcoma, chordoma, mesothelioma, renal cell carcinoma, lung carcinoma, ovarian carcinoma and cancer stem cells representing various histologiesmelanoma, breast cancer, and glioma.

Embodiment 121

The method of embodiment 117, wherein said cancer cell is a metastatic cell.

Embodiment 122

The method of embodiment 117, wherein said cancer cell is a cell of a metastatic melanoma.

Embodiment 123

The method according to any one of embodiments 116-122, wherein said method includes inhibiting, delaying and/or preventing the growth of a tumor and/or spread of malignant tumor cells.

Embodiment 124

The method according to any one of embodiments 116-123, wherein said contacting includes systemically administering said construct or formulation to a mammal.

Embodiment 125

The method according to any one of embodiments 116-123, wherein said contacting includes administering said construct or formulation directly into a tumor site.

Embodiment 126

The method according to any one of embodiments 116-123, wherein said contacting includes administering said construct or formulation via a route selected from the group consisting of oral administration, intravenous administration, intramuscular administration, direct tumor administration, inhalation, rectal administration, vaginal administration, transdermal administration, and subcutaneous depot administration.

Embodiment 127

The method according to any one of embodiments 116-123, wherein said contacting includes administering said construct or formulation intravenously.

Embodiment 128

The method according to any one of embodiments 116-127, wherein said cell is a cell in a human.

Embodiment 129

The method according to any one of embodiments 116-127, wherein said cell is a cell in a non-human mammal.

Embodiment 130

The method of embodiment 116, wherein said contacting includes systemically administering said construct or formulation to a mammal.

Embodiment 131

The method of embodiment 116, wherein said contacting includes administering said construct or formulation directly into a tumor site.

Embodiment 132

The method of embodiment 116, wherein said contacting includes intravenous administration of said construct or formulation.

Embodiment 133

The method of embodiment 116, wherein said cancer cell is a cancer cell in a human.

Embodiment 134

The method of embodiment 116, wherein said cancer cell is a cancer cell in a non-human mammal.

Embodiment 135

The method according to any one of embodiments 117-134, wherein said method further includes administering to said subject one or more cytotoxic agents and/or radiation in an amount effective to reduce tumor load, wherein said construct or formulation inhibits, delays or prevents the growth and/or spread of tumor cells including CSPG4 expressing cells.

Embodiment 136

A method for inhibiting, delaying and/or preventing the growth of a tumor and/or spread of malignant tumor cells in a subject in need thereof, said method including: administering to said subject a chimeric construct according to any of embodiments 1-111, or a formulation according to any one of embodiments 112-115; and administering to said subject one or more cytotoxic agents and/or radiation in an amount effective to reduce tumor load, wherein said immunoconjugate inhibits, delays or prevents the growth and/or spread of tumor cells including CSPG4 expressing cells.

Embodiment 137

A nucleic acid that encodes a fusion protein, said fusion protein including an interferon attached to an anti-CSPG4 single-chain antibody or to a polypeptide including an anti-CSPG4 chain antibody.

Embodiment 138

The nucleic acid of embodiment 137, wherein said interferon is an interferon as found in a construct according to any of embodiments 1-111.

Embodiment 139

The nucleic acid according to any one of embodiments 137-138, wherein said antibody is an anti-CSPG4 antibody as found in a construct according to any of embodiments 1-111.

Embodiment 140

The nucleic acid according to any one of embodiments 137-139, wherein said nucleic acid encodes a construct or a component of a construct according to any of embodiments 1-111.

Embodiment 141

A cell including a nucleic acid that expresses a fusion protein, said cell including a nucleic acid according to any of embodiments 137-140.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

An "antibody", as used herein, refers to a protein consisting of one or more polypeptides substantially encoded by immunoglobulin genes or fragments of immunoglobulin genes. In certain embodiments, the immunoglobulin genes are human immunoglobulin genes. Recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

A typical (native) immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively. It is noted that immunoglobulins IgA and IgM contain multiple copies of the four chain structure.

Antibodies exist as intact immunoglobulins (also referred to as a "full antibody" or a "full-length antibody") or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, IgE, scFv, dAb, nanobodies, unibodies, and diabodies. In various embodiments preferred antibodies include, but are not limited to Fab'$_2$, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs described herein can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) Proc. Natl. Acad. Sci. USA, 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

The term "interferon" refers to a full-length interferon or to an interferon fragment (truncated interferon) or interferon mutant, that substantially retains the biological activity of the full length wild-type interferon (e.g., retains at least 50%, or preferably at least 60%, or preferably at least 70%, or preferably at least 80%, preferably at least 90%, more preferably at least 95%, 98%, or 99% of the full-length interferon in its free form (e.g., when not a component of a chimeric construct). Interferons include type I interferons (e.g., interferon-alpha and interferon-beta) as well as type II interferons (e.g., interferon-gamma). The interferon (e.g., IFN-α) can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the mutated interferon comprises one or more amino acid substitutions, insertions, and/or deletions.

A single chain Fv ("sFv" or "scFv") polypeptide is a covalently linked $V_H$:$V_L$ heterodimer which, in certain embodiments, may be expressed from a nucleic acid including $V_H$- and $V_L$-encoding sequences either joined directly or joined by a peptide-encoding linker. Huston et al. (1998) *Proc. Nat. Acad. Sci. USA*, 85: 5879-5883. A number of approaches for converting the naturally aggregated, but chemically separated light and heavy polypeptide chains from an antibody V region into an sFv molecule that will fold into a three dimensional structure substantially similar to the structure of an antigen-binding site are known (see, e.g., U.S. Pat. Nos. 5,091,513 and 5,132,405, and 4,956,778).

Chrondroitin sulfate proteoglycan 4 (CSPG4) consisting of a protein core and a chondroitin sulfate side chain is also known as high-molecular weight melanoma associated antigen (HMW-MAA) and melanoma chondroitin sulface proteoglycan (MCSP). It has been studied as a target for the treatment of melanoma. This tumor antigen is highly expressed on greater than 80% of human melanomas and has a restricted distribution in normal tissues. CSPG4 plays an important role in the biology of melanoma cells through its modulation of integrin function and enhanced growth factor receptor-regulated pathways including sustained activation of ERK 1,2. It is also expressed on cancer-initiating cells and a broad range of other tumors including breast cancer including triple negative breast cancer, glioma, squamous cell carcinoma of head and neck, myeloid leukemic cells, pancreatic carcinoma, chondrosarcoma, chordoma, mesothelioma, renal cell carcinoma, lung carcinoma, cancer stem cells, and ovarian carcinoma. Expression of CSPG4 is associated with the progression of many different cancers.

The phrase "inhibition of growth and/or proliferation" of a cancer cell refers to decrease in the growth rate and/or proliferation rate of a cancer cell. In certain embodiments this includes death of a cancer cell (e.g. via apoptosis). In certain embodiments this term also refers to inhibiting the growth and/or proliferation of a solid tumor and/or inducing tumor size reduction or elimination of the tumor.

The term "cancer marker" refers to biomolecules such as proteins, carbohydrates, glycoproteins, and the like that are exclusively or preferentially or differentially expressed on a cancer cell and/or are found in association with a cancer cell and thereby provide targets preferential or specific to the cancer. In various embodiments the preferential expression can be preferential expression as compared to any other cell in the organism, or preferential expression within a particular area of the organism (e.g. within a particular organ or tissue).

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or pre-scribing particular agent(s)/compounds for a subject. Such prescribing can include, for example, drafting a prescription form, annotating a medical record, and the like. Where administration is described herein, "causing to be administered" is also contemplated.

The term "exhibiting IFN gamma activity" is intended to indicate that the polypeptide has one or more of the functions of native IFNγ, in particular huIFNγ or rhuIFNγ. Such functions include, inter alia, the capability to bind to an IFNγ receptor and cause transduction of the signal transduced upon huIFNγ-binding of its receptor as determined in vitro or in vivo (i.e., in vitro or in vivo bioactivity). The IFNγ receptor has been described by Aguet et al. (1988) *Cell* 55: 273-280) and Calderon et al. (1988) *Proc. Natl. Acad. Sci. USA*, 85:4837-4841. The "IFNγ polypeptide" is a polypeptide exhibiting IFNγ activity, and is used herein about the polypeptide in monomer or dimeric form, as appropriate. For instance, when specific substitutions are indicated these are normally indicated relative to the IFNγ polypeptide monomer. When reference is made to the IFNγ as part of a conjugate this is normally in dimeric form (and thus, e.g., comprises two IFNγ polypeptide monomers modified as described). The dimeric form of the IFNγ polypeptides may be provided by the normal association of two monomers or be in the form of a single chain dimeric IFNγ polypeptide.

The IFNγ polypeptide described herein may have an in vivo or in vitro bioactivity of the same magnitude as huIFNγ or rhuIFNγ or lower or higher, e.g. an in vivo or in vitro bioactivity of >100% (e.g., 125% or greater, or 150% or greater, or 200% or greater, or 300% or greater, or 400% or greater, or 500% or greater, or 1000% (10-fold) or greater, and so forth), 1-100% of that of huIFNγ or rhuIFNγ, as measured under the same conditions, e.g. 1-25% or 1-50% or 25-100% or 50-100% of that of huIFNγ or rhuIFNγ.

BRIEF DESCRIPTION OF THE DRAWINGS

FIGS. 1A and 1B show the VH (FIG. 1A, amino acid sequence SEQ ID NO:92, DNA sequence SEQ ID NO:93) and VL (FIG. 1B, amino acid sequence SEQ ID NO:94, DNA sequence SEQ ID NO:95) domains of mAb 225.28s (see also, FIGS. 24 and 25 respectively of WO/2013/050725 A1).

DETAILED DESCRIPTION

Malignant melanoma is an immunogenic, highly aggressive and frequently lethal form of skin cancer. It is the most common cancer in the 17-34 years age group but affects people of all ages, and therefore has a significant socioeconomic impact for patients and their families. Although diagnosed skin lesions can be initially excised by surgical intervention, skin and distal metastases unfortunately occur in 20% of patients originally treated with local disease. Patients with lymph node and other distal metastases have dismal prognosis, and this is partly due to lack of effective treatments for this cohort.

Melanoma has presented major challenges to numerous targeted therapy efforts. While interferons have contemplated for use in the treatment of cancer, the effectiveness of interferons for cancer therapy has been overshadowed by side effects when used at high doses.

In various embodiments, interferons are provided attached to an antibody that binds to chrondroitin sulphate proteoglycan 4 (CSPG4, also known as high molecular weight melanoma associated antigen (HMW-MAA)). In certain embodiments, a type I interferon (e.g., human type I IFN), truncated type I interferon (e.g., truncated human type I IFN), and/or mutant type I interferon (e.g., human mutant type I IFN) fused to the C-terminus of an antibody that binds to CSPG4 is provided. In addition to using wild-type human IFN-alpha (alpha2 and natural higher affinity variants such as alpha 14), interferon beta (IFN-β) and interferon gamma (IFN-γ) as well as mutants and/or truncated forms are also contemplated for use in the anti-CSPG4-IFN constructs contemplated herein. In certain illustrative embodiments, the mutant IFN and alpha 14 are expected to have higher affinity than IFN alpha 2 for the interferon receptor and thus greater anti-tumor efficacy.

Figure 2:
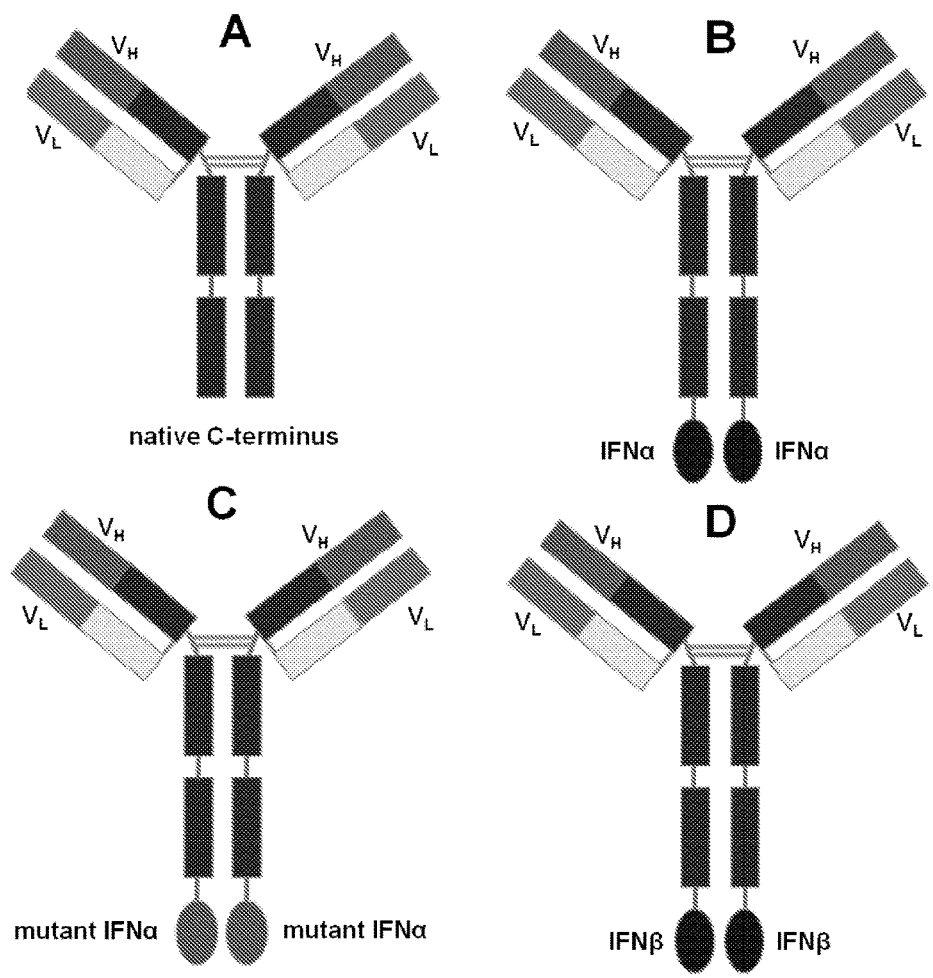
FIG. 2, panels A-H, show the structures of varopis recombinant anti-CSPG4 antibody and IFN fusion proteins. Antibody 9.7.27 $V_H$ and $V_L$ regions recognizing CSPG4 were engineered in recombinant form with human IgG1 constant regions (panel A), or fused at the C-terminus with native IFNα (panel B), or mutant IFNα that mimics the high receptor affinity and potency of IFNβ (panel C). Panel D illustrates an antibody-IFNβ construct while panel E illustrates an antibody-mutant IFNβ construct. Panels F and G illustrate antibody-IFNgamma and antibody-mutant IFNgamma constructs respectively. It is noted that unlike interferon alpha and interferon beta, IFNγ is typically active as a dimer. In the constructs illustrated in Panels F and G, the interferon attached to each of the heavy chains can dimerize with each other to provide activity. In another illustrative embodiments, shown in panel H, two interferon gammas joined by a linker can be attached to one or to each antibody heavy chain and these can dimerize with each other to provide activity.
Figure 3:
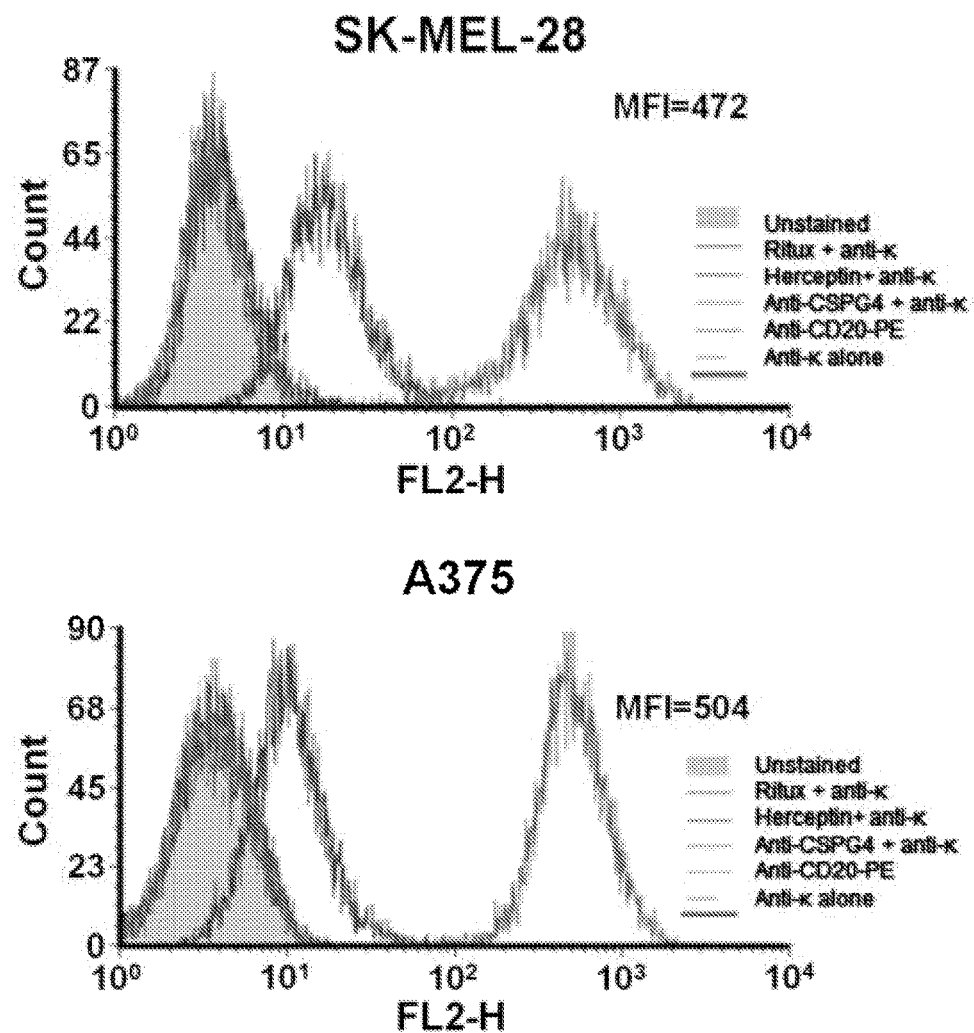
FIG. 3 shows expression of CSPG4 on SKMEL-28 and A375 human melanoma cell lines. Cultured cells were harvested by EDTA and stained with anti-CSPG4, rituximab anti-CD20 antibody (ritux), or trastuzumab anti-HER2 antibody (herceptin), followed by anti-kappa-PE staining, and flow cytometry. Controls include anti-kappa-PE or anti-CD20-PE alone.
Figure 4:
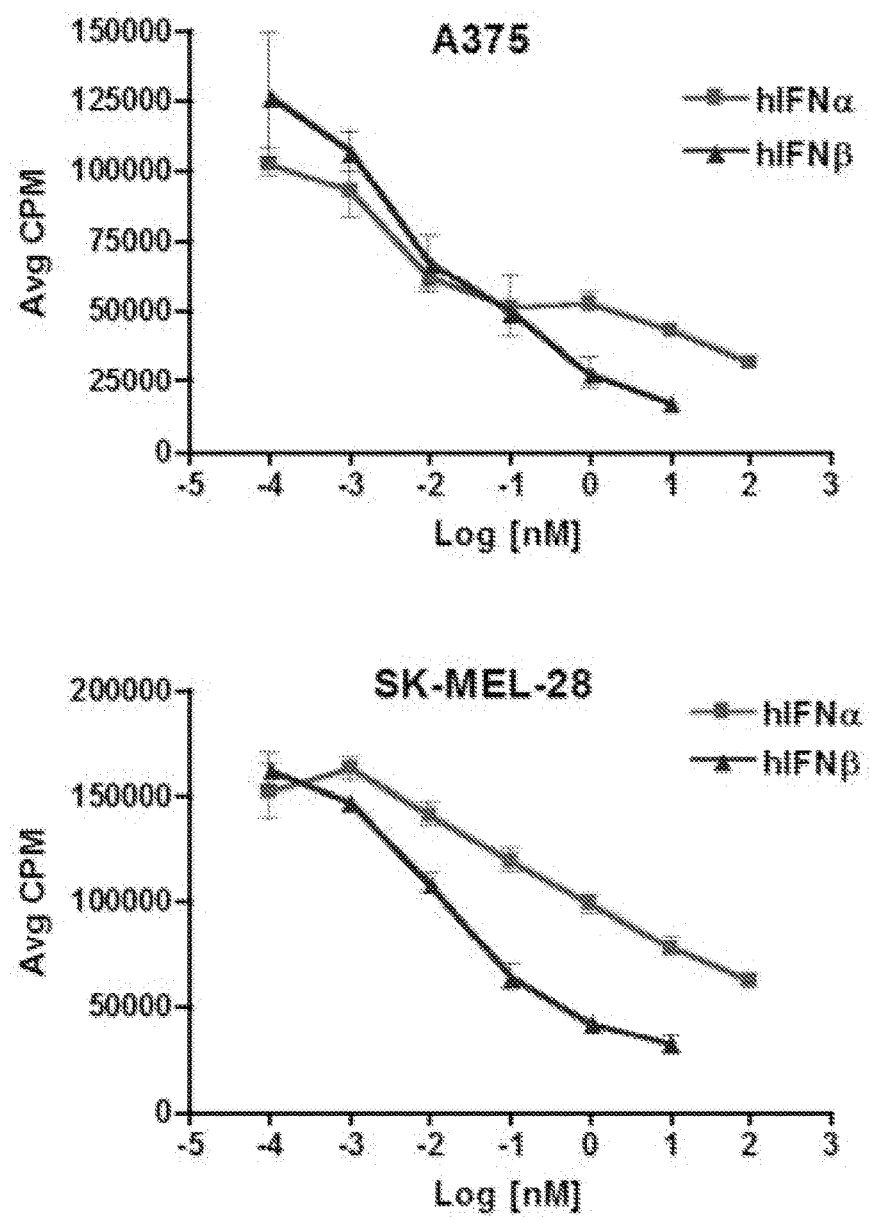
FIG. 4 shows the sensitivity of human melanoma cell lines to recombinant type 1 interferons (IFNα, IFNβ). Tumor cells were seeded in quadruplicate in a 96 well U-bottom plate at $5\times10^3$ cells/well in RPMI complete medium. Media or graded concentrations of hIFNα or hIFNβ starting at 100 nM or 10 nM respectively and serially diluted 10-fold were added at a final volume of 200 μl/well and incubated at 37° C. in a 5% $CO_2$ humidified incubator for 72 hours. Cells were pulsed with 1 μCi/well $^3$[H]-thymidine and harvested 8 hours later. Incorporated radioactivity (counts per minute) was measured using a β-liquid scintillation analyzer and results from 4 replicate cultures reported as arithmetic means±standard deviation.
Figure 6:
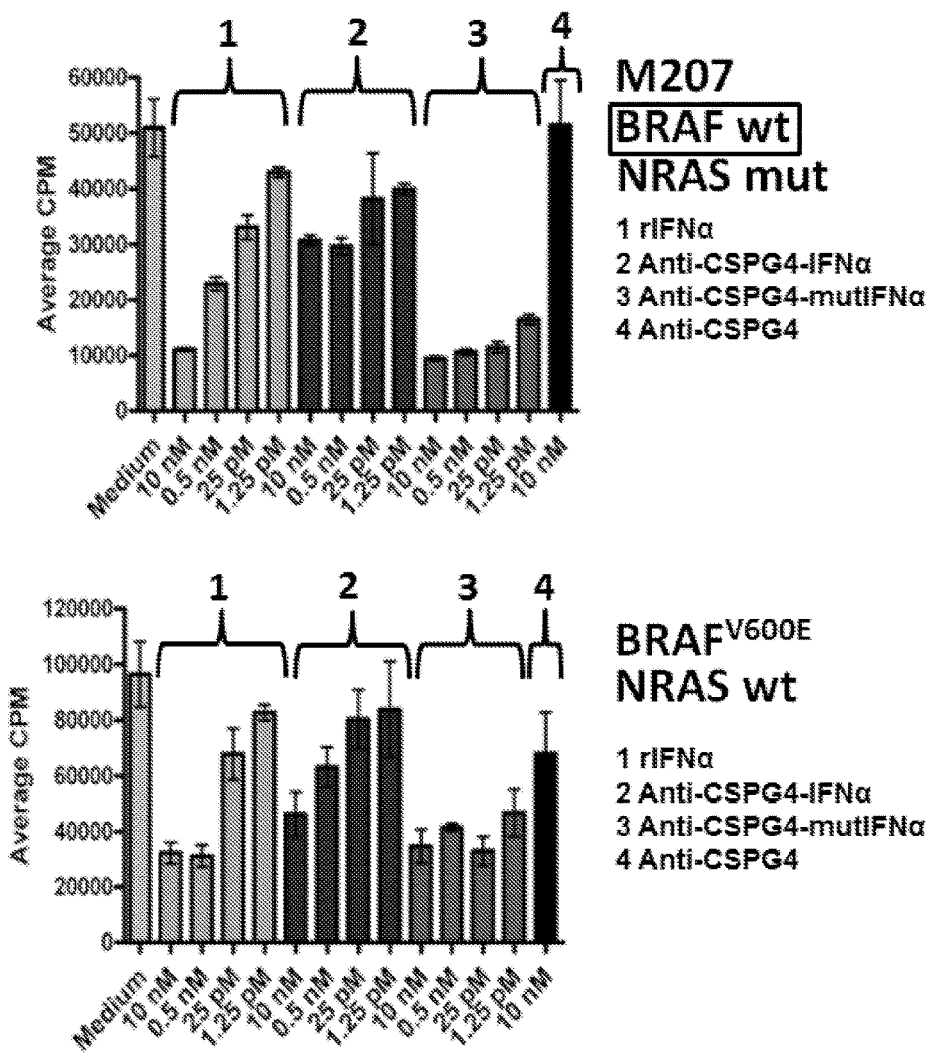
FIG. 6 illustrates inhibition of melanoma cell line proliferation following treatment with IFNα, anti-CSPG4, anti-CSPG4-IFNα or anti-CSPG4-mutIFNα. Quadruplicate samples of cells incubated with the indicated proteins for 48 hours were pulsed for 8 hours with $^3$[H]-thymidine and its incorporation determined.

As demonstrated in the Examples, recombinant forms of the murine monoclonal antibody 9.2.27 that recognizes CSPG4 (26) were engineered into the backbone of human IgG1 (FIG. 2) and expressed as a fusion protein with interferon. Various constructs included a native form of the antibody, a fusion containing human IFNα, and a fusion containing a mutant IFNα2 (mutIFNα (e.g., IFNα2$^{YNS}$)) that mimics IFNβ in terms of higher affinity binding to IFNAR1 (see, e.g., Eyal et al. (2007) *J. Biol. Chem.* 282(15): 11602-11611). The recombinant anti-CSPG4 antibody recognized 2 different human melanoma cell lines (SK-MEL-28 and A375) in a specific manner, showing high-level binding (FIG. 3). Both of these cell lines were sensitive to growth inhibition by free, recombinant human IFNα and IFNβ, with IFNβ being more effective, as expected (FIG. 4). The native IgG1 anti-CSPG4 antibody had no effect on the growth of either cell line. The anti-CSPG4-hIFNα fusion was effective at modestly inhibiting the growth of SK-MEL-28 cells, and inhibiting A375 proliferation by 50-60%. By contrast, the anti-CSPG4-mutIFNα fusion potently inhibited the growth of both cell lines, achieving approximately 70% inhibition of SK-MEL-28 and 80% inhibition of A375. Anti-CSPG4-IFNα and anti-CSPG4-mutIFNα also inhibited the proliferation of melanoma cells with different BRAF and NRAS mutations (FIG. 6) with anti-CSPG4-mutIFNα more effective than anti-CSPG4-IFNα.

Figure 7:
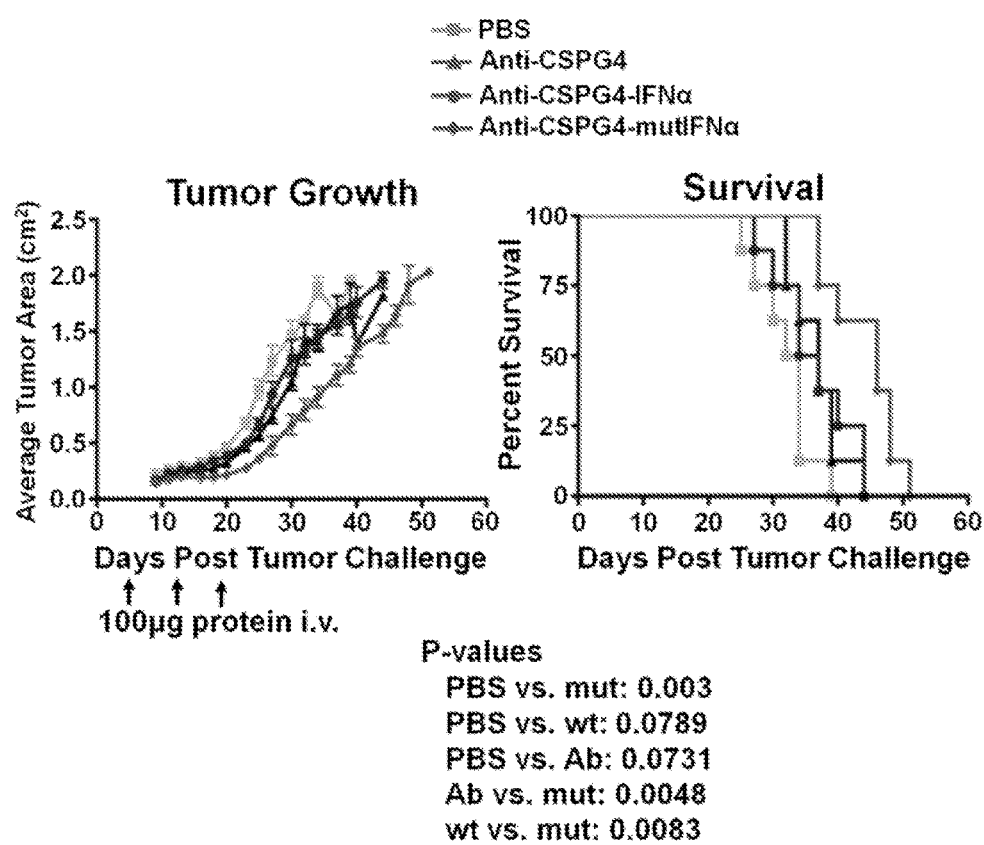
FIG. 7 shows the in vivo efficacy of anti-CSPG4, anti-CSPG4-IFNα and anti-CSPG4-mutIFNα against human melanoma xenografts. SCID mice were injected with $2\times10^6$ A375 cells s.c. on day 0. Groups of 8 mice were treated with 100 μg protein i.v. on days 5, 12, and 19 and followed for tumor growth and survival. Palpable tumors were bi-directionally measured three times per week using calipers. Animals were sacrificed when their tumors reached 1.4 cm in diameter, per institutional guidelines.

To test the ability of the fusion proteins to inhibit tumor growth in vivo, A375 cells were grown as subcutaneous xenografts in immunodeficient SCID mice (FIG. 7). After 5 days of tumor growth, mice were treated with a short course (days 5, 12, and 19) of intravenous phosphate buffered saline control, native anti-CSPG4 IgG1, anti-CSPG4-IFNα, or anti-CSPG4-mutIFNα. In mice treated with saline, tumors grew progressively, and all tumors had reached 1.4 cm in diameter before day 40. Treatment with native antibody or anti-CSPG4-IFN appeared to slightly delay tumor growth (all tumors reaching 1.4 cm in diameter by day 44) although these differences were not statistically significant compared to saline control (p=0.073 and p=0.079, respectively). However, treatment with anti-CSPG4mutIFNα significantly delayed the growth of tumors compared to saline control (p=0.003), native antibody (p=0.0048), and anti-CSPG4-IFNα (p=0.0048). Notably, tumors did not appear to progress in mice treated with anti-CSPG4-mutIFNα until after day 19, when therapy was stopped, suggesting ongoing suppression of tumor growth in vivo. Thus, even a brief course of low-dose anti-CSPG4-mutIFNα fusion protein therapy was able to significantly delay the growth a human melanoma in vivo.

Accordingly, it is believed that anti-CSPG4-Interferon constructs are highly potent agents for the inhibition of growth or proliferation of cells that express CSPG4, notably cancer cells that express CSPG4. Such cancers include, but are not limited to melanoma, triple negative breast cancer, and malignant gliomas.

Thus, in certain embodiments, the constructs (e.g., chimeric moieties) comprising an interferon (e.g., IFNα, IFNβ, IFNγ, mutant IFNα, mutant IFNβ, mutant IFNγ, truncated IFNα, truncated IFNβ, truncated IFNγ, etc.) attached to a targeting moiety (e.g., to an antibody that specifically binds CSPG4) are provided. In certain embodiments the constructs include chemical conjugates as well as fusion proteins. Also provided are nucleic acids encoding the fusion proteins (or components thereof) as well as cells transfected with the nucleic acids to express the fusion proteins. Also provided are methods of inhibiting growth and proliferation of cells that express or overexpress CSPG4 using the constructs described herein. In certain embodiments, the cells that express or over express CSPG4 are cancer cells (e.g., melanoma, triple negative breast cancer, malignant glioma, etc.). Accordingly in various embodiments, methods are provided for inhibiting, delaying and/or preventing the growth of a tumor and/or spread of malignant tumor cell using the constructs described herein. In addition, kits comprising the constructs are provided, e.g., for the treatment of various cancers.

I. Constructs Comprising a Targeting Moiety Attached to an Interferon.

It was a surprising discovery that constructs comprising a targeting moiety that binds (e.g., that preferentially or specifically binds) to CSPG4 attached to a native (wildtype) or modified IFN (e.g., mutant IFN-α) can be effectively used to inhibit the growth and/or proliferation of target cells (e.g., cancer cells) that express or overexpress CSPG4. In certain embodiments the CSPG4 targeting moieties are chemically conjugated to the interferon, while in other embodiments, the CSPG4 targeting moiety (or a component thereof) is expressed as a fusion protein with the interferon. When produced as a fusion protein the CSPG4 targeting moiety (e.g., antibody) (or a component thereof) can be directly fused to the interferon or attached by means of a peptide linker (e.g., a (Gly$_4$Ser)$_3$ (SEQ ID NO:1) linker, a Gly$_4$Ser (SEQ ID NO:2) linker, a SerGly$_4$Ser linker (SEQ ID NO:3), an AEAAAKEAAAKA (SEQ ID NO:4) linker, and the like.

Antibodies that bind to CSPG4

In various embodiments constructs are contemplated comprising an antibody or antibody fragment that binds specifically to CSPG4 attached to an interferon (e.g., full length interferon, biologically active interferon fragment, biologically active interferon mutant, etc.). Antibodies that specifically bind CSPG4 are known to those of skill in the art and a number of different monoclonal antibodies that specifically bind CSPG4 have been produced (see, e.g., PCT Publication WO/2010/033866, and the like).

In addition, anti-CSPG4 antibodies can be made using methods well known to those of skill in the art. For example, antibodies can be produced by immunizing an animal with CSPG4 or an immunogenic fragment thereof and raising the antibodies in that animal. Polyclonal antibodies can be recovered and used or converted to monoclonal antibodies according to methods well known to those of skill in the art.

CSPG4 is a well known and well characterized protein. In one embodiment, has an amino acid sequence set forth as:

```
                                                           (SEQ ID NO: 5)
         10         20         30         40         50         60
MQSGPRPPLP APGLALALTL TMLARLASAA SFFGENHLEV PVATALTDID LQLQFSTSQP 70         80         90        100        110        120
EALLLLAAGP ADHLLLQLYS GRLQVRLVLG QEELRLQTPA ETLLSDSIPH TVVLTVVEGW 130        140        150        160        170        180
ATLSVDGFLN ASSAVPGAPL EVPYGLFVGG TGTLGLPYLR GTSRPLRGCL HAATLNGRSL 190        200        210        220        230        240
LRPLTPDVHE GCAEEFSASD DVALGFSGPH SLAAFPAWGT QDEGTLEFTL TTQSRQAPLA 250        260        270        280        290        300
FQAGGRRGDF IYVDIFEGHL RAVVEKGQGT VLLHNSVPVA DGQPHEVSVH INAHRLEISV 310        320        330        340        350        360
DQYPTHTSNR GVLSYLEPRG SLLLGGLDAE ASRHLQEHRL GLTPEATNAS LLGCMEDLSV 370        380        390        400        410        420
NGQRRGLREA LLTRNMAAGC RLEEEEYEDD AYGHYEAFST LAPEAWPAME LPEPCVPEPG 430        440        450        460        470        480
LPPVFANFTQ LLTISPLVVA EGGTAWLEWR HVQPTLDLME AELRKSQVLF SVTRGARHGE 490        500        510        520        530        540
LELDIPGAQA RKMFTLLDVV NRKARFIHDG SEDTSDQLVL EVSVTARVPM PSCLRRGQTY 550        560        570        580        590        600
LLPIQVNPVN DPPHIIFPHG SLMVILEHTQ KPLGPEVFQA YDPDSACEGL TFQVLGTSSG 610        620        630        640        650        660
LPVERRDQPG EPATEFSCRE LEAGSLVYVH RGGPAQDLTF RVSDGLQASP PATLKVVAIR 670        680        690        700        710        720
PAIQIHRSTG LRLAQGSAMP ILPANLSVET NAVGQDVSVL FRVTGALQFG ELQKQGAGGV 730        740        750        760        770        780
EGAEWWATQA FHQRDVEQGR VRYLSTDPQH HAYDTVENLA LEVQVGQEIL SNLSFPVTIQ 790        800        810        820        830        840
RATVWMLRLE PLHTQNTQQE TLTTAHLEAT LEEAGPSPPT FHYEVVQAPR KGNLQLQGTR 850        860        870        880        890        900
LSDGQGFTQD DIQAGRVTYG ATARASEAVE DTFRFRVTAP PYFSPLYTFP IHIGGDPDAP 910        920        930        940        950        960
VLTNVLLVVP EGGEGVLSAD HLFVKSLNSA SYLYEVMERP RHGRLAWRGT QDKTTMVTSF 970        980        990       1000       1010       1020
TNEDLLRGRL VYQHDDSETT EDDIPFVATR QGESSGDMAW EEVRGVFRVA IQPVNDHAPV 1030       1040       1050       1060       1070       1080
QTISRIFHVA RGGRRLLTTD DVAFSDADSG FADAQLVLTR KDLLFGSIVA VDEPTRPIYR 1090       1100       1110       1120       1130       1140
FTQEDLRKRR VLFVHSGADR GWIQLQVSDG QHQATALLEV QASEPYLRVA NGSSLVVPQG 1150       1160       1170       1180       1190       1200
GQGTIDTAVL HLDTNLDIRS GDEVHYHVTA GPRWGQLVRA GQPATAFSQQ DLLDGAVLYS 1210       1220       1230       1240       1250       1260
HNGSLSPRDT MAFSVEAGPV HTDATLQVTI ALEGPLAPLK LVRHKKIYVF QGEAAEIRRD 1270       1280       1290       1300       1310       1320
QLEAAQEAVP PADIVFSVKS PPSAGYLVMV SRGALADEPP SLDPVQSFSQ EAVDTGRVLY 1330       1340       1350       1360       1370       1380
LHSRPEAWSD AFSLDVASGL GAPLEGVLVE LEVLPAAIPL EAQNFSVPEG GSLTLAPPLL 1390       1400       1410       1420       1430       1440
RVSGPYFPTL LGLSLQVLEP PQHGALQKED GPQARTLSAF SWRMVEEQLI RYVHDGSETL
```

```
     1450      1460       1470       1480       1490       1500
TDSFVLMANA SEMDRQSHPV AFTVTVLPVN DQPPILTTNT GLQMWEGATA PIPAEALRST 1510      1520       1530       1540       1550       1560
DGDSGSEDLV YTIEQPSNGR VVLRGAPGTE VRSFTQAQLD GGLVLFSHRG TLDGGFRFRL 1570      1580       1590       1600       1610       1620
SDGEHTSPGH FFRVTAQKQV LLSLKGSQTL TVCPGSVQPL SSQTLRASSS AGTDPQLLLY 1630      1640       1650       1660       1670       1680
RVVRGPQLGR LFHAQQDSTG EALVNFTQAE VYAGNILYEH EMPPEPFWEA HDTLELQLSS 1690      1700       1710       1720       1730       1740
PPARDVAATL AVAVSFEAAC PQRPSHLWKN KGLWVPEGQR ARITVAALDA SNLLASVPSP 1750      1760       1770       1780       1790       1800
QRSEHDVLFQ VTQFPSRGQL LVSEEPLHAG QPHFLQSQLA AGQLVYAHGG GGTQQDGFHF 1810      1820       1830       1840       1850       1860
RAHLQGPAGA SVAGPQTSEA FAITVRDVNE RPPQPQASVP LRLTRGSRAP ISRAQLSVVD 1870      1880       1890       1900       1910       1920
PDSAPGEIEY EVQRAPHNGF LSLVGGGLGP VTRFTQADVD SGRLAFVANG SSVAGIFQLS 1930      1940       1950       1960       1970       1980
MSDGASPPLP MSLAVDILPS AIEVQLRAPL EVPQALGRSS LSQQQLRVVS DREEPEAAYR 1990      2000       2010       2020       2030       2040
LIQGPQYGHL LVGGRPTSAF SQFQIDQGEV VFAFTNFSSS HDHFRVLALA RGVNASAVVN 2050      2060       2070       2080       2090       2100
VTVRALLHVW AGGPWPQGAT LRLDPTVLDA GELANRTGSV PRFRLLEGPR HGRVVRVPRA 2110      2120       2130       2140       2150       2160
RTEPGGSQLV EQFTQQDLED GRLGLEVGRP EGRAPGPAGD SLTLELWAQG VPPAVASLDF 2170      2180       2190       2200       2210       2220
ATEPYNAARP YSVALLSVPE AARTEAGKPE SSTPTGEPGP MASSPEPAVA KGGFLSFLEA 2230      2240       2250       2260       2270       2280
NMFSVIIPMC LVLLLLALIL PLLFYLRKRN KTGKHDVQVL TAKPRNGLAG DTETFRKVEP 2290      2300       2310       2320
GQAIPLTAVP GQGPPPGGQP DPELLQFCRT PNPALKNGQY WV
```

See, also, GENBANK Accession No. Q6UVK1 incorporated herein by reference (note leader is underlined in above sequence).

In certain embodiments the CSPG4 protein can be encoded by the nucleic acid sequence set forth as:

```
                                                        (SEQ ID NO: 6)
   1 gcgcccagga gcagagccgc gctcgctcca ctcagctccc agctcccagg actccgctgg 61 ctcctcgcaa gtcctgccgc ccagcccgcc gggatgcagt ccgggccgcg gcccccactt 121 ccagccccccg gcctggcctt ggctttgacc ctgactatgt tggccagact tgcatccgcg 181 gcttccttct tcggtgagaa ccacctggag gtgcctgtgg ccacggctct gaccgacata 241 gacctgcagc tgcagttctc cacgtcccag cccgaagccc tcttctcct ggcagcaggc 301 ccagctgacc acctcctgct gcagctctac tctggacgcc tgcaggtcag acttgttctg 361 ggccaggagg agctgaggct gcagactcca gcagagacgc tgctgagtga ctccatcccc 421 cacactgtgg tgctgactgt cgtagagggc tgggccacgt tgtcagtcga tgggtttctg 481 aacgcctcct cagcagtccc aggagccccc ctagaggtcc cctatgggct ctttgttggg 541 ggcactggga cccttggcct gcctacctg aggggaacca gccgacccct gaggggttgc 601 ctccatgcag ccaccctcaa tggccgcagc ctcctccggc ctctgacccc cgatgtgcat 661 gagggctgtg ctgaagagtt ttctgccagt gatgatgtgg ccctgggctt ctctgggccc 721 cactctctgg ctgccttccc tgcctggggc actcaggacg aaggaaccct agagtttaca
```

-continued

```
 781 ctcaccacac agagccggca ggcacccttg gccttccagg caggggggccg gcgtggggac 841 ttcatctatg tggacatatt tgagggccac ctgcgggccg tggtggagaa gggcagggt 901 accgtattgc tccacaacag tgtgcctgtg ccgatgggc agccccatga ggtcagtgtc 961 cacatcaatg ctcaccggct ggaaatctcc gtggaccagt accctacgca tacttcgaac 1021 cgaggagtcc tcagctacct ggagccacgg ggcagtctcc ttctcggggg gctggatgca 1081 gaggcctctc gtcacctcca ggaacaccgc ctgggcctga caccagaggc caccaatgcc 1141 tccctgctgg gctgcatgga agacctcagt gtcaatggcc agaggcgggg gctgcgggaa 1201 gctttgctga cgcgcaacat ggcagccggc tgcaggctgg aggaggagga gtatgaggac 1261 gatgcctatg acattatga agctttctcc accctggccc ctgaggcttg ccagccatg 1321 gagctgcctg agccatgcgt gcctgagcca gggctgcctc ctgtctttgc caatttcacc 1381 cagctgctga ctatcagccc actggtggtg gccgaggggg gcacagcctg gcttgagtgg 1441 aggcatgtgc agcccacgct ggacctgatg gaggctgagc tgcgcaaatc ccaggtgctg 1501 ttcagcgtga cccgaggggc acgccatggc gagctcgagc tggacatccc gggagcccag 1561 gcacgaaaaa tgttcaccct cctggacgtg gtgaaccgca aggcccgctt catccacgat 1621 ggctctgagg acacctccga ccagctggtg ctggaggtgt cggtgacggc tcgggtgccc 1681 atgccctcat gccttcggag gggccaaaca tacctcctgc ccatccaggt caaccctgtc 1741 aatgacccac cccacatcat cttcccacat ggcagcctca tggtgatcct ggaacacacg 1801 cagaagccgc tggggcctga ggttttccag gcctatgacc cggactctgc ctgtgagggc 1861 ctcaccttcc aggtccttgg cacctcctct ggcctcccg tggagcgccg agaccagcct 1921 ggggagccgg cgaccgagtt ctcctgccgg gagttggagg ccggcagcct agtctatgtc 1981 caccgcggtg gtcctgcaca ggacttgacg ttccgggtca gcgatggact gcaggccagc 2041 ccccggcca cgctgaaggt ggtggccatc cggccggcca tacagatcca ccgcagcaca 2101 gggttgcgac tggcccaagg ctctgccatg cccatcttgc ccgccaacct gtcggtggag 2161 accaatgccg tggggcagga tgtgagcgtg ctgttccgcg tcactggggc cctgcagttt 2221 ggggagctgc agaagcaggg ggcaggtggg gtggagggtg ctgagtggtg gccacacag 2281 gcgttccacc agcgggatgt ggagcagggc cgcgtgaggt acctgagcac tgacccacag 2341 caccacgctt acgacaccgt ggagaacctg gccctggagg tgcaggtggg ccaggagatc 2401 ctgagcaatc tgtccttccc agtgaccatc cagagagcca ctgtgtggat gctgcggctg 2461 gagccactgc acactcagaa cacccagcag gagaccctca ccacagccca cctggaggcc 2521 accctggagg aggcaggccc aagcccccca accttccatt atgaggtggt tcaggctccc 2581 aggaaaggca accttcaact acagggcaca aggctgtcag atggccaggg cttcacccag 2641 gatgacatac aggctggccg ggtgacctat ggggccacag cacgtgcctc agaggcagtc 2701 gaggacacct tccgtttccg tgtcacagct ccaccatatt tctcccccact ctataccttc 2761 cccatccaca ttggtggtga cccagatgcg cctgtcctca ccaatgtcct cctcgtggtg 2821 cctgagggtg gtgagggtgt cctctctgct gaccacctct tgtcaagag tctcaacagt 2881 gccagctacc tctatgaggt catggagcgg ccccgccatg ggaggttggc ttggcgtggg 2941 acacaggaca agaccactat ggtgacatcc ttcaccaatg aagacctgtt gcgtggccgg 3001 ctggtctacc agcatgatga ctccgagacc acagaagatg atatcccatt tgttgctacc 3061 cgccagggcg agagcagtgg tgacatggcc tgggaggagg tacgggtgt cttccgagtg 3121 gccatccagc ccgtgaatga ccacgcccct gtgcagacca tcagccggat cttccatgtg 3181 gcccgggggtg ggcggcggct gctgactaca gacgacgtgg ccttcagcga tgctgactcg
```

-continued

```
3241 ggctttgctg acgcccagct ggtgcttacc cgcaaggacc tcctctttgg cagtatcgtg
3301 gccgtagatg agcccacgcg gcccatctac cgcttcaccc aggaggacct caggaagagg
3361 cgagtactgt tcgtgcactc aggggctgac cgtggctgga tccagctgca ggtgtccgac
3421 gggcaacacc aggccactgc gctgctggag gtgcaggcct cggaacccta cctccgtgtg
3481 gccaacggct ccagccttgt ggtccctcaa ggaggccagg gcaccatcga cacggccgtg
3541 ctccacctgg acaccaacct cgacatccgc agtggggatg aggtccacta ccacgtcaca
3601 gctggccctc gctggggaca gctagtccgg gctggtcagc cagccacagc cttctcccag
3661 caggacctgc tggatggggc cgttctctat agccacaatg gcagcctcag cccccgcgac
3721 accatggcct tctccgtgga agcagggcca gtgcacacgg atgccaccct acaagtgacc
3781 attgccctag agggcccact ggccccactg aagctggtcc ggcacaagaa gatctacgtc
3841 ttccagggag aggcagctga gatcagaagg gaccagctgg aggcagccca ggaggcagtg
3901 ccacctgcag acatcgtatt ctcagtgaag agcccaccga gtgccggcta cctggtgatg
3961 gtgtcgcgtg gcgccttggc agatgagcca cccagcctgg accctgtgca gagcttctcc
4021 caggaggcag tggacacagg cagggtcctg tacctgcact cccgccctga ggcctggagc
4081 gatgccttct cgctggatgt ggcctcaggc ctgggtgctc ccctcgaggg cgtccttgtg
4141 gagctggagg tgctgccgc tgccatccca ctagaggcgc aaaacttcag cgtccctgag
4201 ggtggcagcc tcaccctggc ccctccactg ctccgtgtct ccgggcccta cttccccact
4261 ctcctgggcc tcagcctgca ggtgctggag ccaccccagc atggagccct gcagaaggag
4321 gacggacctc aagccaggac cctcagcgcc ttctcctgga gaatggtgga agagcagctg
4381 atccgctacg tgcatgacgg gagcgagaca ctgacagaca gttttgtcct gatggctaat
4441 gcctccgaga tggatcgcca gagccatcct gtggccttca ctgtcactgt cctgcctgtc
4501 aatgaccaac cccccatcct cactacaaac acaggcctgc agatgtggga gggggccact
4561 gcgcccatcc ctgcggaggc tctgaggagc acggacggcg actctgggtc tgaggatctg
4621 gtctacacca tcgagcagcc cagcaacggg cgggtagtgc tgcgggggc gccgggcact
4681 gaggtgcgca gcttcacgca ggcccagctg acggcgggc tcgtgctgtt ctcacacaga
4741 ggaaccctgg atggaggctt ccgcttccgc ctctctgacg gcgagcacac ttcccccgga
4801 cacttcttcc gagtgacggc ccagaagcaa gtgctcctct cgctgaaggg cagccagaca
4861 ctgactgtct gcccagggtc cgtccagcca ctcagcagtc agaccctcag ggccagctcc
4921 agcgcaggca ctgaccccca gctcctgctc taccgtgtgg tgcggggccc ccagctaggc
4981 cggctgttcc acgcccagca ggacagcaca ggggaggccc tggtgaactt cactcaggca
5041 gaggtctacg ctgggaatat tctgtatgag catgagatgc ccccgagcc cttttgggag
5101 gcccatgata ccctagagct ccagctgtcc tcgccgcctg cccgggacgt ggccgccacc
5161 cttgctgtgg ctgtgtcttt tgaggctgcc tgtcccagc gccccagcca cctctggaag
5221 aacaaaggtc tctgggtccc cgagggccag cgggccagga tcaccgtggc tgctctggat
5281 gcctccaatc tcttggccag cgttccatca ccccagcgct cagagcatga tgtgctcttc
5341 caggtcacac agttccccag ccggggccag ctgttggtgt ccgaggagcc cctccatgct
5401 gggcagcccc acttcctgca gtcccagctg gctgcagggc agctagtgta tgcccacggc
5461 ggtgggggca cccagcagga tggcttccac tttcgtgccc acctccaggg gccagcaggg
5521 gcctccgtgg ctggaccca aacctcagag gcctttgcca tcacggtgag ggatgtaaat
5581 gagcggcccc ctcagccaca ggcctctgtc ccactccggc tcacccgagg ctctcgtgcc
```

-continued

```
5641 cccatctccc gggcccagct gagtgtggtg gacccagact cagctcctgg ggagattgag 5701 tacgaggtcc agcgggcacc ccacaacggc ttcctcagcc tggtgggtgg tggcctgggg 5761 cccgtgaccc gcttcacgca agccgatgtg gattcagggc ggctggcctt cgtggccaac 5821 gggagcagcg tggcaggcat cttccagctg agcatgtctg atggggccag cccaccccctg 5881 cccatgtccc tggctgtgga catcctacca tccgccatcg aggtgcagct gcgggcaccc 5941 ctggaggtgc cccaagcttt ggggcgctcc tcactgagcc agcagcagct ccgggtggtt 6001 tcagatcggg aggagccaga ggcagcatac cgcctcatcc agggacccca gtatgggcat 6061 ctcctggtgg gcgggcggcc cacctcggcc ttcagccaat tccagataga ccagggcgag 6121 gtggtctttg ccttcaccaa cttctcctcc tctcatgacc acttcagagt cctggcactg 6181 gctaggggtg tcaatgcatc agccgtagtg aacgtcactg tgaggctct gctgcatgtg 6241 tgggcaggtg ggccatggcc ccagggtgcc accctgcgcc tggaccccac cgtcctagat 6301 gctggcgagc tggccaaccg cacaggcagt gtgccgcgct tccgcctcct ggagggaccc 6361 cggcatggcc gcgtggtccg cgtgccccga gccaggacgg agcccggggg cagccagctg 6421 gtggagcagt tcactcagca ggaccttgag gacgggaggc tggggctgga ggtgggcagg 6481 ccagagggga gggcccccgg ccccgcaggt gacagtctca ctctggagct gtgggcacag 6541 ggcgtcccgc tgctgtggc ctccctggac tttgccactg agccttacaa tgctgcccgg 6601 ccctacagcg tggccctgct cagtgtcccc gaggccgccc ggacggaagc agggaagcca 6661 gagagcagca cccccacagg cgagccaggc cccatggcat ccagccctga gcccgctgtg 6721 gccaagggag gcttcctgag cttccttgag gccaacatgt tcagcgtcat catccccatg 6781 tgcctggtac ttctgctcct ggcgctcatc ctgcccctgc tcttctacct ccgaaaacgc 6841 aacaagacgg gcaagcatga cgtccaggtc ctgactgcca agccccgcaa cggcctggct 6901 ggtgacaccg agacctttcg caaggtggag ccaggccagg ccatcccgct cacagctgtg 6961 cctggccagg ggcccctcc aggaggccag cctgacccag agctgctgca gttctgccgg 7021 acacccaacc ctgcccttaa gaatggccag tactgggtgt gaggcctggc ctgggcccag 7081 atgctgatcg ggccagggac aggcttgccc atgtcccggg ccccattgct tccatgcctg 7141 gtgctgtctg agtatcccca gagcaagaga gacctggaga caccaggggt ggagggtcct 7201 gggagatagt cccaggggtc cgggacagag tggagtcaag agctggaacc tcctcagct 7261 cactccgagc ctggagaact gcaggggcca aggtggaggc aggcttaagt tcagtcctcc 7321 tgccctggag ctggtttggg ctgtcaaaac cagggtaacc tcctacatgg gtcatgactc 7381 tgggtcctgg gtctgtgacc ttgggtaagt cgcgcctgac ccaggctgct aagagggcaa 7441 ggagaaggaa gtaccctggg gagggaaggg acagaggaag ctattcctgg cttttccact 7501 ccaacccagg ccacccttg tctctgcccc agagttgaga aaaaacttc ctcccctggt 7561 tttttaggga gatggtatcc cctggagtag agggcaagag gagagagcgc ctccagtcta 7621 gaaggcataa gccaatagga taatatattc agggtgcagg gtgggtaggt tgctctgggg 7681 atgggtttat ttaagggaga ttgcaaggaa gctatttaac atggtgctga gctagccagg 7741 actgatggag cccctggggg tgtgggatgg aggagggtct gcagccagtt cattcccagg 7801 gccccatctt gatgggccaa ggctaaaca tgcatgtgtc agtggctttg agcaggtta 7861 ggctggggct catcgagggt ctcaggccga ggccactgcg gtgccagtgc cccctgagg 7921 actagggcag gcagctgggg gcacttggtt ccatggagcc tggataaaca gtgctttgga 7981 ggctctggac agctgtgtgg tgtttgtgtc ttaactatgc actgggccct tgtctgcgtc 8041 ggcttgcata cagagggccc ctggggtcgg ccctccggcc tggcctcagc cagtgggatg
```

-continued

```
8101 gacagggcca ggcaggcctc tgaacttcca cctcctgggg cctcccagac ctcctgtgcc 8161 cccacctgtg tgggcaggtg ggccagtctt cgggtgatgg gaccaaaccc cttcagttca 8221 gtagagaaag gctaggtcct ctacaaagag ctgcaagaca aaaattaaaa taaatgctcc 8281 ccaccctaga aaaaaaaaaa aaaaa
```

See also Genebank ACCESSION No: NM_001897, which is incorporated herein by reference.

One of skill in the art can readily use this or other nucleic acid sequences encoding CSPG4 to produce a CSPG4 polypeptide (e.g., for use in raising antibodies) using standard methods in molecular biology (see, e.g., Sambrook et al. (1989) Molecular Cloning: A Laboratory Manual, 2nd ed., vol. 1-3, Cold Spring Harbor Laboratory Press, Cold Spring Harbor, N.Y.).

In certain embodiments, single chain anti-CSPG4 antibodies can be created using a phage display library. One such method is described by Fernandez et al. (2005) *J. Clin. Oncol., ASCO Annual Meeting Proceedings.* 23(16S), Part I of II (June 1 Supplement), 2005: 2550. The authors used combinatorial immunoglobulin (Ig) libraries with phage display to generate in vitro human Ig Fab fragments without the need to maintain on-going hybridoma culture. A library of $10^{10}$ clones from the cDNA of peripheral blood mononuclear cells of patients with adenocarcinoma was used to identify target-specific Ig. Generally following removal of non-specific Fabs by exposing the Ig library to the epithelial cell line HEK, target-specific antibodies were selected by exposing the Fab library to HEK transduced with the target protein. Six rounds of selection resulted in a panel of target specific phage. Similar methods can readily be used to produce anti-CSPG4 antibodies in addition to the antibodies described below.

In various embodiments, the anti-CSPG4 antibodies used in the constructs described herein specifically bind to CSPG4 to form an immune complex. Typically the antibody comprises an antigen-binding region (e.g. one or more variable regions, or one to 6 CDRs) derived from an antibody that is known to bind CSPG4, preferably human CSPG4.

In certain embodiments the antibody binds to CSPG4 with an affinity greater than ($K_D$ less than) about $1\times10^{-6}$ M, or a $K_D$ less than about $1\times10^{-7}$ M, or a $K_D$ less than about $1\times10^{-8}$ M or a $K_D$ less than about $1\times10^{-9}$ M, or a $K_D$ less than about $1\times10^{-10}$ M, or a $K_D$ less than about $1\times10^{-11}$ M, or a $K_D$ less than about $1\times10^{-12}$ M as measured using a BiaCore®.

Antibodies that bind to CSPG4 are disclosed, for example, in WO 1989/011296. Such antibodies include mouse monoclonal antibodies 225.28, 225.28s; 763.74; VF1-TP41.2; VT80.1 12; 653.25; 763.74; TP61.5, and T8-203 (see e.g., WO 1989/11296; Drake et al. (2009) *Cancer Immunol. Immunother.,* 58(3): 415-427; Goto et al. (2008) *Clin. Cancer Res.* 14: 3401-3407), 9.2.27 (see, e.g., Morgan et al. (1981) *Hybridoma,* 1: 27-36) single chain antibodies 149.53, 225.28, 763.74, TP61.5, VF1-TP34, and VF1-TP41.2 (see, e.g., Campoli et al. (2004) *Crit. Rev. Immunol.,* 24: 267-296 and Wang et al. (2011) *Cancer Res.,* 71(24): 7410-7422), MEL-14, MEL-5 (see, e.g., U.S. Patent Publication No: 2010/0047164), and the like.

In certain embodiments the antibodies used in the CSPG4-interferon constructs contemplated herein comprise at least one, or at least two, or three complementarity determining regions (CDRs) from the VH region of an antibody determined to specifically bind CSPG4 (e.g., an antibody shown in Table 1) and/or at least one, or at least two, or three complementarity determining regions (CDRs) from the VL region of an antibody determined to specifically bind CSPG4 (e.g., an antibody shown in Table 1). In certain embodiments the antibody comprises a variable region (e.g. a heavy chain variable domain (VH) and/or a light chain variable domain (VL)) region of an antibody determined to specifically bind CSPG4 (e.g., an antibody shown in Table 1).

The amino acid sequences of these antibodies are well known to those of skill in the art. For example, European Patent Publication No: EP 0411893 A2 gives the amino acid sequence of the 9.2.27 VL domain as:

```
                                            (SEQ ID NO: 7)
NIVLTQSPAS LAVSLGQRAT ISCRASESVD SYGNSFMHWY

QQKPGQPPKL LIYLASNLES GVPARFSGSG SRTDFTLTID

PVEADDAATY YCQQNNEDPL TFGSGTKLEI KR
``` and the 9.2.27 VH domain as:

```
                                            (SEQ ID NO: 8)
QVQLQQSGPE LVKPGASVKI SCKASGYAFS RSWMNWVKQR

PGQGLEWIGR IYPGDGDTNY NGKFKGKATL TADKSSSTAY

MQVSSLTSVD SAVYFCARGN TVVVPYTMDY WGQGTSVTVS S
```

Similarly, the amino acid sequences of the VH and VL domains of mAb 225.28s are shown in FIGS. 24 and 25 respectively of WO/2013/050725 A1, reproduced herein as FIGS. 1A and 1B, respectively.

In certain embodiments the antibody is a chimeric, humanized, or fully human antibody (or fragment thereof) that binds the epitope bound by any one or more of the antibodies shown in Table 1. In certain embodiments the antibody is a chimeric, humanized, or fully human antibody (or fragment thereof) derived from any one or more of the antibodies shown in Table 1 (e.g., derived from 9.2.27).

In certain embodiments the antibody comprises one or more human constant regions, e.g. one or more human heavy chain constant domains (e.g. E constant domains) and/or a human light chain (e.g. K or X) constant domain. In certain embodiments the antibody comprises one or more human framework regions within the VH and/or VL domains.

In certain embodiments the sequence of the humanized immunoglobulin heavy chain variable region framework and/or the humanized light chain variable region framework can be at least about 65%, or at least about 75%, or at least about 85% m or at least about 90%, or at least about 95%, or at least about 98%, or at least about 99% identical to the sequence of the donor immunoglobulin heavy chain and/or light chain variable region framework respectively. Human framework regions, and mutations that can be made in a humanized antibody framework regions, are known in the art (see, for example, U.S. Pat. No. 5,585,089).

In another embodiment, the antibody comprises one or more variable regions capable of binding specifically to CSPG4, and one or more constant regions. In certain embodiments the antibody is a chimeric antibody, a humanized antibody or a human antibody. In one embodiment, the antibody comprises one or more variable domains derived from an igE isotype. In certain embodiments the antibody comprises one or more variable domains derived from an immunoglobulin isotype other than IgE (e.g., IgA, IgD, IgG or IgM, for example IgG1), and one or more constant domains derived from an immunoglobulin of the isotype IgE or another isotype.

In certain embodiments the antibody comprises one or more complementarity-determining regions (CDRs) derived from an immunoglobulin isotype other than IgE (e.g., IgA, IgD, IgG or IgM, for example IgG1), and one or more framework regions and or constant domains derived from an immunoglobulin of the isotype IgE. For instance, in certain embodiments, the antibody may comprise one or more variable domains or complementarity-determining regions (CDRs) derived from an IgG, e.g. IgG1.

In certain embodiments the variable domains or CDRs are derived from a first mammalian species, and the framework regions and/or constant domains are derived from a second mammalian species different to the first mammalian species. In one embodiment, the variable regions or CDRs are derived from a non-human species, e.g. a mouse and the framework regions and/or constant domains are human.

TABLE 1

Illustrative combinations of antibodies and interferons for the anti-CSPG4-Interferon constructs described herein. It will be recognized that the antiboides can comprise full-length listed antibodies or CDRs derived from the VH and/or the VL domain of these antibodies. The interferons can comprise the native interferons, truncated interferons, mutant interferons, and the like. mutIFN indicates a mutant interferon, e.g., such as the mutant interferons described below.

| Antibody | | | Attached Interferon | | | |
|---|---|---|---|---|---|---|
| 9.2.27 | IFN-α | IFN-β | IFN-γ | mutIFN-α | mutIFN-β | mutIFN-γ |
| 225.28 | IFN-α | IFN-β | IFN-γ | mutIFN-α | mutIFN-β | mutIFN-γ |
| 225.28s | IFN-α | IFN-β | IFN-γ | mutIFN-α | mutIFN-β | mutIFN-γ |
| 763.74 | IFN-α | IFN-β | IFN-γ | mutIFN-α | mutIFN-β | mutIFN-γ |
| VF1-TP41.2 | IFN-α | IFN-β | IFN-γ | mutIFN-α | mutIFN-β | mutIFN-γ |
| VT80.1 | IFN-α | IFN-β | IFN-γ | mutIFN-α | mutIFN-β | mutIFN-γ |
| 653.25 | IFN-α | IFN-β | IFN-γ | mutIFN-α | mutIFN-β | mutIFN-γ |
| 763.74 | IFN-α | IFN-β | IFN-γ | mutIFN-α | mutIFN-β | mutIFN-γ |
| TP61.5 | IFN-α | IFN-β | IFN-γ | mutIFN-α | mutIFN-β | mutIFN-γ |
| T8-203 | IFN-α | IFN-β | IFN-γ | mutIFN-α | mutIFN-β | mutIFN-γ |
| 149.53 | IFN-α | IFN-β | IFN-γ | mutIFN-α | mutIFN-β | mutIFN-γ |
| 225.28 | IFN-α | IFN-β | IFN-γ | mutIFN-α | mutIFN-β | mutIFN-γ |
| 763.74 | IFN-α | IFN-β | IFN-γ | mutIFN-α | mutIFN-β | mutIFN-γ |
| TP61.5 | IFN-α | IFN-β | IFN-γ | mutIFN-α | mutIFN-β | mutIFN-γ |
| VF1-TP34 | IFN-α | IFN-β | IFN-γ | mutIFN-α | mutIFN-β | mutIFN-γ |
| VF1-TP41.2 | IFN-α | IFN-β | IFN-γ | mutIFN-α | mutIFN-β | mutIFN-γ |
| MEL-14 | IFN-α | IFN-β | IFN-γ | mutIFN-α | mutIFN-β | mutIFN-γ |
| MEL-5 | IFN-α | IFN-β | IFN-γ | mutIFN-α | mutIFN-β | mutIFN-γ |

Antibodies against CSPG4 sequences can be generated by well-established methods, and at least the variable regions or CDRs from such antibodies may be used in the constructs described herein. Thus, for example, the generated antibodies may be used to donate CDR or variable region sequences into IgE (or other isotype) acceptor sequences. Methods for synthesizing polypeptides and immunizing a host animal are well known in the art. Typically, the host animal (e.g. a mouse) is inoculated intraperitoneally with an amount of immunogen (e.g., CSPG4 or a polypeptide comprising an immunogenic fragment thereof), and (in the case of monoclonal antibody production) hybridomas prepared from its lymphocytes and immortalized myeloma cells using, for example, the general somatic cell hybridization technique of Kohler and Milstein (1975) *Nature,* 25(6):495-497.

Hybridomas that produce suitable antibodies can be grown in vitro or in vivo using known procedures. Monoclonal antibodies can be isolated from the culture media or body fluids, by conventional immunoglobulin purification procedures such as ammonium sulfate precipitation, gel electrophoresis, dialysis, chromatography, and ultrafiltration, if desired. Undesired activity if present can be removed, for example, by running the preparation over adsorbents made of the immunogen attached to a solid phase and eluting or releasing the desired antibodies off the immunogen. If desired, the antibody (monoclonal or polyclonal) of interest may be sequenced and the polynucleotide sequence may then be cloned into a vector for expression or propagation. The sequence encoding the antibody may be maintained in a vector in a host cell and the host cell can then be expanded and frozen for future use.

Phage display technology, for instance as described in U.S. Pat. No. 5,565,332 and other published documents, may be used to select and produce human antibodies and antibody fragments in vitro, from immunoglobulin variable (V) domain gene repertoires from unimmunized donors (e.g., from human subjects, including patients suffering from a relevant disorder). For example, existing antibody phage display libraries may be panned in parallel against a large collection of synthetic polypeptides. According to this technique, antibody V domain genes are cloned in-frame into either a major or minor coat protein gene of a filamentous bacteriophage, such as F1, M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus antibody sequences selected using phage display from human libraries may include human CDR or variable region sequences conferring specific binding to CSPG4, which may be used to provide fully human antibodies for use in constructs described herein.

Methods for deriving heavy and light chain sequences from human B cell and plasma cell clones are also well known in the art and typically performed using polymerase chain reaction (PGR) techniques, examples of the methods are described in: Kuppers (2004) *Meth. Mol. Biol.,* 271: 225-238; Yoshioka et al. (2011) *BMC Biotechnol.* 11: 75; Scheeren et al. (2011) *PLoS ONE,* 6(4): e17189. Wrammert et al. (2008) *Nature,* 453: 667-671; Kurosawa et al. (2011) *BMC Biotechnol.* 11: 39; Tiller et al. (2007) *J. Immunol. Meth.,* 329(1-2): 112-124. Thus, in various embodiments antibody sequences selected using B cell clones may include human CDR or variable region sequences conferring specific binding to CSPG4, which may be used to provide fully human antibodies for use in the present invention.

Using the known sequences for the various anti-CSPG4 antibodies (e.g., the antibodies listed in Table 1, such as 9.2.27), a variety of phage display (or yeast display) methods can be used to generate other antibodies that specifically bind CSPG4 with the same or even greater affinity.

Chain Shuffling Methods.

One approach to creating antibody variants has been to replace the original VH or VL gene with a repertoire of V-genes to create new partners (chain shuffling) (Clackson et al. (1991) *Nature.* 352: 624-628) in a phage display or yeast display library. Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of an anti-CSPG4 antibody (e.g., the 9.2.27 antibody), a mutant scFv gene repertoire can be created containing a $V_H$ gene of the prototypic 9.2.27 antibody and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133-4137) or other vectors, and after transformation a library of transformants is obtained.

Similarly, for heavy chain shuffling, a mutant scFv gene repertoire can be created containing a $V_L$ gene of the prototypic 9.2.27 antibody and a human $V_H$ gene repertoire (heavy chain shuffling). The scFv gene repertoire can be cloned into a phage display vector, e.g., pHEN-1 (Hoogenboom et al. (1991) *Nucleic Acids Res.*, 19: 4133-4137) or other vectors, and after transformation a library of transformants is obtained.

The resulting libraries can be screened against the relevant target (e.g., CSPG4) and/or for cross-reactivity with one or more of the antibodies shown in Table 1.

Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901-917; Chothia et al. (1986) *Science*, 233: 755-8; Nhan et al. (1991) *J. Mol. Biol.*, 217: 133-151). These residues contribute the majority of binding energetics responsible for antibody affinity for antigen. In other molecules, mutating amino acids that contact the target ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Site-directed mutagenesis of CDRs and screening against the target, in particular for binding at CSPG4, can produce antibodies having improved binding affinity.

CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., 9.2.27 or one or more of the other antibodies in Table 1) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.*, 234: 564-578).

$V_H$ CDR3 often occupies the center of the binding pocket, and thus mutations in this region are likely to result in an increase in affinity (Clackson et al. (1995) *Science*, 267: 383-386). In one embodiment, three $V_H$ CDR3 residues randomized as described, for example, by Schier et al. (1996) *Gene*, 169: 147-155; Schier and Marks (1996) *Human Antibodies and Hybridomas.* 7: 97-105; and Schier et al. (1996) *J. Mol. Biol.* 263: 551-567.

Other Antibody Modifications.

In one embodiment, partial antibody sequences derived from the anti-CSPG4 antibody (e.g., 9.2.27 or other antibodies in Table 1) may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332: 323-327; Jones et al., (1986) *Nature* 321: 522-525; and Queen et al. (1989) *Proc. Natl. Acad. Sci. USA,* 86: 10029-10033). Such framework sequences can be obtained from public DNA databases that include germline antibody gene sequences.

Thus, one or more structural features of an anti-CSPG4 antibody described herein (e.g., 9.2.27), such as the CDRs, can be used to create structurally related anti-CSPG4 antibodies that retain at least one functional property of, for example, the 9.2.27 antibody, e.g., binding of target cancer cells.

In a particular embodiment, one or more anti-CSPG4 (e.g., 9.2.27) CDR regions (e.g. VH CDR1, and/or CDR2, and/or CDR3, and/or VL CDR1, and/or CDR2, and/or CDR3) is combined recombinantly with known human framework regions and CDRs to create additional, recombinantly-engineered, anti-CSPG4 antibodies. The heavy and light chain variable framework regions can be derived from the same or different antibody sequences.

It is well known in the art that antibody heavy and light chain CDR3 domains play a particularly important role in the binding specificity/affinity of an antibody for an antigen (see, e.g., Hall et al. (1992) *J. Immunol.*, 149: 1605-1612; Polymenis et al. (1994) *J. Immunol.*, 152: 5318-5329; Jahn et al. (1995) *Immunobiol.*, 193:400-419; Klimka et al. (2000) *Brit. J. Cancer,* 83: 252-260; Beiboer et al. (2000) *J. Mol. Biol,* 296: 833-849; Rader et al. (1998) *Proc. Natl. Acad. Sci. USA,* 95: 8910-8915; Barbas et al. (1994) *J. Am. Chem. Soc.,* 116: 2161-2162; Ditzel et al. (1996) *J. Immunol.,* 157: 739-749). Accordingly, in certain embodiments, antibodies are generated that include the heavy and/or light chain CDR3s of the particular antibodies described herein (e.g., 9.2.27 or other antibodies in Table 1). In certain embodiments, antibodies are generated that include the heavy and/or light chain CDR1s of the particular antibodies described herein (e.g., 9.2.27). The antibodies can further include the other heavy and/or light chain CDRs of the antibodies of the present invention (e.g., 9.2.27 or other antibodies in Table 1).

In certain embodiments the CDR1, 2, and/or 3 regions of the engineered antibodies described above can comprise the exact amino acid sequence(s) as those disclosed herein (e.g., CDRs of 9.2.27 or other antibodies in Table 1). However, the ordinarily skilled artisan will appreciate that some deviation from the exact CDR sequences may be possible while still retaining the ability of the antibody to bind CSPG4 effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of the 9.2.27 or other antibodies in Table 1.

In another embodiment, one or more residues of a CDR may be altered to modify binding to achieve a more favored on-rate of binding. Using this strategy, an antibody having ultra high binding affinity of, for example, $10^{-10}$ M or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC) (see, e.g., Caron et al. (1992) *J. Exp Med.* 176: 1191-1195; Shopes (1992) *J. Immunol.* 148: 2918-2922). Homodimeric antibodies with enhanced anti-tumor activity may also be prepared using heterobifunctional cross-linkers (see, e.g., Wolff et al. (1993) *Cancer Res.* 53:2560-2565). Alternatively, an antibody can be engineered which has dual Fc regions and may thereby have enhanced complement lysis and ADCC capabilities (see, e.g., Stevenson et al. (1989) *Anti-Cancer Drug Design* 3: 219-230).

It is noted that in various embodiments, antibodies suitable for use in the antibody-IFN constructs described herein comprise an antibody selected from the group consisting of a full length immunoglobulin, an Fv, an Fab, a (Fab')$_2$, a (Fab')$_3$, an IgGΔCH2, and a minibody, a unibody, an affibody, and the like. In certain embodiments the antibody is a full length immunoglobulin (e.g., IgA, IgD, IgG or IgM).

Any of the antibodies described herein (e.g., the antibodies in Table 1 such as 9.2.27 and variants thereof, e.g., as described herein) can readily be engineered into any of these formats. In this regard, it is noted that fully human antibodies and fragments thereof that bind to CSPG4 are disclosed in WO 2010/045495 (e.g., an scFv fragment isolated from a semi-synthetic phage display scFv antibody library and designated C21) and similar methods can be used to generate and modify other anti-CSGP4 antibodies. EP 0411893 A2 describes methods and constructs for expressing the 9.2.27 antibody and variants thereof.

With respect to sequence identity described above, it is noted that similarity between amino acid or nucleotide sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of the amino acid or nucleotide sequence will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al, Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al, J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the anti-CSPG4 antibodies or a domain thereof (e.g., a VL, VH, CL or CH domain) typically have at least about 75%, for example at least about 80%, 90%, 95%, 96%, 97%, 98% or 99% sequence identity with the original sequence (e.g. a sequence defined above), for example counted over the full length alignment with the amino acid sequence of the antibody or domain thereof using the NCBI Blast 2.0, gapped blastp set to default parameters. For comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment can be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Typically variants may contain one or more conservative amino acid substitutions compared to the original amino acid or nucleic acid sequence. Conservative substitutions are those substitutions that do not substantially affect or decrease the affinity of an antibody to CSPG4. For example, a human antibody that specifically binds CSPG4 may include up to 1, up to 2, up to 5, up to 10, or up to 15 conservative substitutions compared to the original sequence (e.g. as defined above) and retain specific binding to the CSPG4 polypeptide. The term conservative variation also includes the use of a substituted amino acid in place of an unsubstituted parent amino acid, provided that antibody specifically binds CSPG4. Non-conservative substitutions are those that reduce an activity or binding to CSPG4.

Functionally similar amino acids that may be exchanged by way of conservative substitution are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

While the above discussion pertains primarily to antibodies, it will be recognized that affybodies and/or unibodies can be used instead of antibodies.

Unibodies.

UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule left only one area on the UniBody that can bind to a target. Methods of producing unibodies are described in detail in PCT Publication WO2007/059782, (see, also, Kolfschoten et al. (2007) Science 317: 1554-1557) and can be used to create unibodies based on any known anti-CSPG4 antibody.

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (see, e.g., Nord et al. (1997) Nat. Biotechnol. 15: 772-777; Ronmark et al. (2002) Eur. J. Biochem., 269: 2647-2655.). Details of Affibodies and methods of production are known to those of skill (see, e.g., U.S. Pat. No. 5,831,).

B) Interferons

In various embodiments chimeric moieties of this invention comprise an interferon (e.g., IFN-α, IFNβ, IFN-γ, etc.) joined to a targeting moiety (e.g., anti-CSPG4 antibody). In various embodiments the interferon can be a full length wild-type interferon (e.g. IFN-α, IFNβ, IFN-γ, etc.) an interferon fragment (e.g., an IFN-α fragment), and/or a mutated interferon. Typically the interferon fragment is one that possesses the endogenous binding affinity and/or activity of the native interferon, preferably at a level of at least 60%, or of at least 80%, more preferably at least 90% or 95%, most preferably at least 98%, 99%, 100%, or a level greater than the wild-type interferon (in its isolated form).

Interferons and interferon mutants are a well known and well characterized group of cytokines (see e.g., WO 2002/095067; WO 2002/079249; WO 2002/101048; WO 2002/095067; WO 2002/083733; WO 2002/086156; WO 2002/083733; WO 2003/000896; WO 2002/101048; WO 2002/079249; WO 2003/000896; WO 2004/022593; WO 2004/022747; WO 2003/023032; WO 2004/022593 and also in Kim et al. (2003) Cancer Lett. 189(2):183-188; Hussain et al. (2000) J. Interferon Cytokine Res. 20(9): 763-768; Hussain et al. (1998) J. Interferon Cytokine Res. 18(7): 469-477; Nyman et al. (1988) Biochem. J. 329 (Pt 2): 295-302; Golovleva et al. (1997) J. Interferon Cytokine Res. 17(10): 637-645; Hussain et al. (1997) J. Interferon Cytokine Res. 17(9): 559-566; Golovleva et al. (1997) Hum. Hered. 47(4): 185-188; Kita et al. (1997) J. Interferon Cytokine Res. 17(3): 135-140; Golovleva et al. (1996) Am. J. Hum. Genet. 59(3): 570-578; Hussain et al. (1996) J. Interferon Cytokine Res. 16(7): 523-529; Linge et al. (1995) Biochim Biophys Acta. 1264(3): 363-368; Gewert et al. (1995) J Interferon Cytokine Res. 15(5): 403-406; Lee et al. (1995) J. Interferon Cytokine Res. 15(4): 341-349; Kaluz et al. (1994) Acta Virol. 38(2): 101-104; Emanuel et al. (1993) J. Interferon Res. 13(3): 227-231; Kaluz et al. (1993) Acta Virol. 37(1): 97-100; Li et al. (1992) Sci. China B. 35(2): 200-206.

By way of illustration, alleles of the human interferon α family of genes/proteins are illustrated in Table 2.

TABLE 2

Common alleles of the human interferon α family of genes/proteins and was constructed based on Pestka (1983) Arch Biochem Biophys 221: 1-37; Diaz et al. (1994) Genomics 22: 540-52; and Pestka (1986) Meth. Enzymol., 119: 3-14; and reviewed in Krause et al. (2000) J. Biol. Chem. 275: 22995-3004.

| Gene | Interferon Proteins (allelic variant names) |
|---|---|
| IFNA1 | IFN-α1, IFN- αD |
| IFNA2 | IFN- α2, IFN α2b, IFN- αA, IFN-α2a, INF-α2c |
| IFNA4 | IFN-α4a, IFNα76, IFN-α4b, IFN-α74, IFN-αM |
| IFNA5 | IFN-α5, IFNαG, IFN-α61 |
| IFNA6 | IFN-α6, IFN-αK, IFN-α54 |
| IFNA7 | IFN-α7, IFN-αJ, IFN-αJ1 |
| IFNA8 | IFN-α8, IFN-αB2, IFN-αB |
| IFNA10 | IFN-αC, IFN-α61 |
| IFNA13 | IFN-α13 |
| IFNA14 | IFN-α14, IFN-αH, IFN-αH1 |
| IFNA16 | IFN-α16, IFN-αWA, IFN-αO |
| IFNA17 | IFN-α17,IFN-α1, IFN-α88 |
| IFNA21 | IFN-α21, IFN-αF |
| IFNA22 | IFN-α22, IFN-αGX-1 |

Any of these IFN-α are contemplated for use in the constructs described herein. Additionally IFN-β, IFN-γ, biologically active truncated interferons (truncated IFN-α, IFN-β, IFN-γ), and mutant interferons (e.g., mutant IFN-α, IFN-β, IFN-γ) are contemplated.

In certain embodiments the interferon is a full-length IFN-α, a full-length IFN-β, or a full length IFN-γ.

In certain embodiments the interferon is a biologically active truncated IFN-α, a biologically active truncated IFN-β, or a biologically active truncated IFN-γ.

Means of identifying such truncated or modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408).

The resulting library members can then be screened according to standard methods know to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

In various embodiments use of a mutated interferon alpha 2 (IFNα2) is contemplated. Certain mutants include a mutation of the His at position 5, and/or the E at position 5, and/or the Q at position 6. In certain embodiments the mutants include the mutation H57Y, and/or E58N, and/or Q61S. In certain embodiments the mutants include a mutated IFNα2 having the mutations H57Y, E58N, and Q61S (YNS) (see, e.g., Kalie et al. (2007) J. Biol. Chem., 282: 11602-11611).

In other embodiments mutants include a mutation of the His at position 5, and/or the E at position 5, and/or the Q at position 6 to A (alanine). In certain embodiments the mutants include a mutated IFNα2 having the mutations H57A, E58A, and Q61A (HEQ) (see, e.g., Jaitin et al. (2006)

*Mol. Cellular Biol.*, 26(5): 1888-1897). In certain embodiments the mutant interferon comprises a mutation of His at position 5 to A, Y, or M, and/or a mutation of E at position 5 to A, or N, or D, or L, and/or a mutation of Q at position 6 to A, or S, or L, or D.

In certain embodiments mutant include mutants of interferon alpha 8 (IFN-α8). Three mutant IFN-α8 molecules were identified (R145V, A146N, M149Y), (R145I, A146S, M149Y), and (R145L, A146S, M149Y)] that displayed improved anti-proliferative activity against a wide range of different cell lines (see, e.g., Yamamoto et. al. (2009) *J. Interferon & cytokine Res*, 29:161-170. Accordingly, in certain embodiments IFN-α8 mutants are contemplated that have R145 to V, I, or L, and/or A146 to N, or S, and/or M149 to Y are contemplated.

A mutated IFNβ comprising a serine substituted for the naturally occurring cysteine at amino acid 17 has also been demonstrated to show efficacy (see, e.g., Hawkins et al. (1985) *Cancer Res.*, 45, 5914-5920.

In various embodiments use of truncated interferons is also contemplated. Human INFα, for example, with deletions of the first 15 amino-terminal amino acid residues and/or the last 10-13 carboxyl-terminal amino acid residues, have been shown to exhibit virtually the same activity as the parent molecules (see, e.g., Ackerman (1984) *Proc. Natl. Acad. Sci., USA*, 81: 1045-1047). Accordingly the use of IFN-αs having 1, 2, 3, up to 13 carboxyl terminal amino acid residues deleted and/or 1, 2, 3, up to 15 amino terminal amino acid residues deleted are contemplated.

It has also been demonstrated that activity resides in huIFN-α fragment HuIFN-α (1-110) (Id.). Accordingly carboxyl truncated IFNs with truncations after residue 110 and/or with 1, 2, 3, up to 15 amino terminal amino acid residues deleted are contemplated.

Certain C-terminally truncated interferon betas (IFNβ) have been shown to have increased activity (see, e.g., U.S. Patent Publication 2009/0025106 A1). Accordingly, in certain embodiments the interferon used in the constructs described herein includes the C-terminally truncated IFNβ described as IFN-Δ1, IFN-Δ2, IFN-Δ3, IFN-Δ4, IFN-Δ5, IFN-Δ6, IFN-Δ7, IFN-Δ8, IFN-Δ9, or IFN-Δ10 as described in U.S. Patent Publication NO: 2009/0025106 A1. In certain embodiments the interferon is IFN-Δ7, IFN-Δ8, or IFN-Δ9 (SEQ ID NOs: 57, 59, and 61 in US 2009/0025106 A1 (see, Table 3).

TABLE 3

Truncated IFNβ showing enhanced activity
(see U.S. patent publication 2009/0025106 A1).

| Truncated IFN | Amino Acid Sequence | SEQ ID NO |
|---|---|---|
| IFN-Δ7 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu Gln | 9 |
| IFN-Δ8 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile the Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr the Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu | 10 |
| IFN-Δ9 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu the Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile the Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn | 11 |

In certain embodiments mutant interferons include, but are not limited to mutant interferons described in U.S. Pat. No. 7,998,469 which is incorporated herein by reference for the mutant interferons described therein. Illustrative and non limiting interferons include, for example, IFNα-2b proteins that have increased resistance proteolysis compared to the unmodified, typically wild-type, protein. The mutant IFNα-2b proteins include those selected from among proteins containing a single amino acid replacement, or a dual amino acid replacement, or a triple amino acid replacement, or 4 amino acid replacements, or 5 amino acid replacement in IFN-α2b:

```
                                              (SEQ ID NO: 12)
Cys Asp Leu Pro Gln Thr His Ser Leu Gly Ser Arg

Arg Thr Leu Met Leu Leu Ala Gln Met Arg Arg Ile

Ser Leu Phe Ser Cys Leu Lys Asp Arg His Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu
``` where the replacements are selected from the group consisting of: L by V at position 3; L by I at position 3; P by S at position 4; P by A at position 4; R by H at position 1; R by Q at position 1; R by H at position 1; R by Q at position 1; M by V at position 1; M by I at position 1; R by H at position 2; R by Q at position 2; R by H at position 2; R by Q at position 2; F by I at position 2; F by V at position 2; L by V at position 3; L by I at position 3; K by Q at position 3; K by T at position 3; R by H at position 3; R by Q at position 3; E by Q at position 4; E by H at position 4; K by Q at position 4; K by T at position 4; E by Q at position 5; E by H at position 5; K by Q at position 7; K by T at position 7; E by Q at position 7; E by H at position 7; K by Q at position 83; K by T at position 83; Y by H at position 8; Y by I at position 8; E by Q at position 9; E by H at position 9; E by Q at position 17; E by H at position 17; P by S at position 19; P by A at position 19; L by V at position 10; L by I at position 10; M by V at position 11; M by I at position 11; E by Q at position 13; E by H at position 13; L by V at position 17; L by I at position 17; R by H at position 10; R by Q at position 10; K by Q at position 11; K by T at position 11; R by H at position 15; R by Q at position 15; L by V at position 18; L by I at position 18; K by Q at position 11; K by T at position 11; E by Q at position 12; E by H at position 12; K by Q at position 13; K by T at position 13; K by Q at position 14; K by T at position 14; Y by H at position 15; Y by I at position 15; P by S at position 17; P by A at position 17; M by V at position 18; M by I at position 18; R by H at position 19; R by Q at position 19; E by Q at position 19; E by H at position 19; L by V at position 11; L by I at position 11; R by H at position 12; R by Q at position 12; K by Q at position 14; K by T at position 14; E by Q at position 15; and E by H at position 15.

In certain embodiments C-terminal deletions of interferon gamma (IFN-γ) are also contemplated (see, e.g., Lundell et al. (1991) *Protein Neg.*, 4(3): 335-341).

In certain embodiments, N-glycosylation sites can be added to increase resistance to proteolysis while maintaining or improving the requisite biological activity. Exemplary N-glycosylation mutants containing duo-amino acid replacements corresponding to the N-X-S or N-X-T consensus sequences are set forth in Example 3. Accordingly, provided herein are IFNα-2b and IFNα-2a mutant proteins having an increased resistance to proteolysis compared to unmodified IFNα-2b and IFNα-2a, selected from among proteins comprising one, or two, or three or four, or five, or more sets of duo-amino acid replacements in IFN-α2b (SEQ ID NO: 12), corresponding to:

D by N at position 2 and P by S at position 4;
D by N at position 2 and P by T at position 4;
L by N at position 3 and Q by S at position 5;
L by N at position 3 and Q by T at position 5;
P by N at position 4 and T by S at position 6;
P by N at position 4 and T by T at position 6;
Q by N at position 5 and H by S at position 7;
Q by N at position 5 and H by T at position 7;
T by N at position 6 and S by S at position 8;
T by N at position 6 and S by T at position 8;
H by N at position 7 and L by S at position 9;
H by N at position 7 and L by T at position 9;
S by N at position 8 and G by S at position 1;
S by N at position 8 and G by T at position 1;
L by N at position 9 and S by S at position 1;
L by N at position 9 and S by T at position 1;
M by N at position 2 and K by S at position 2;
M by N at position 2 and K by T at position 2;
R by N at position 2 and I by S at position 2;
R by N at position 2 and I by T at position 2;
K or R by N at position 2 and S by S at position 2;
K or R by N at position 2 and S by T at position 2;
I by N at position 2 and L by S at position 2;
I by N at position 2 and L by T at position 2;
S by N at position 2 and F by S at position 2;
S by N at position 2 and F by T at position 2;
L by N at position 2 and S by S at position 2;
L by N at position 2 and S by T at position 2;
S by N at position 2 and L by S at position 3;
S by N at position 2 and L by T at position 3;
L by N at position 3 and D by S at position 3;
L by N at position 3 and D by T at position 3;
K by N at position 3 and R by S at position 3;
K by N at position 3 and R by T at position 3;
D by N at position 3 and H by S at position 3;
D by N at position 3 and H by T at position 3;
R by N at position 3 and D by S at position 3;
R by N at position 3 and D by T at position 3;
H by N at position 3 and F by S at position 3;
H by N at position 3 and F by T at position 3;
D by N at position 3 and G by S at position 3;
D by N at position 3 and G by T at position 3;
F by N at position 3 and F by S at position 3;
F by N at position 3 and F by T at position 3;
G by N at position 3 and P by S at position 3;
G by N at position 3 and P by T at position 3;
F by N at position 3 and Q by S at position 4;
F by N at position 3 and Q by T at position 4;
P by N at position 3 and E by S at position 4;
P by N at position 3 and E by T at position 4;
Q by N at position 4 and E by S at position 4;
Q by N at position 4 and E by T at position 4;
E by N at position 4 and F by S at position 43;
E by N at position 4 and F by T at position 43;
E by N at position 4 and G by S at position 4;

E by N at position 4 and G by T at position 4;
F by N at position 43 and N by S at position 4;
F by N at position 43 and N by T at position 4;
G by N at position 4 and Q by S at position 4;
G by N at position 4 and Q by T at position 4;
N by N at position 4 and F by S at position 4;
N by N at position 4 and F by T at position 4;
Q by N at position 4 and Q by S at position 4;
Q by N at position 4 and Q by T at position 4;
F by N at position 4 and K by S at position 4;
F by N at position 4 and K by T at position 4;
Q by N at position 4 and A by S at position 5;
Q by N at position 4 and A by T at position 5;
K by N at position 4 and E by S at position 5;
K by N at position 4 and E by T at position 5;
A by N at position 5 and T by S at position 5;
A by N at position 5 and T by T at position 5;
S by N at position 6 and K by S at position 7;
S by N at position 6 and K by T at position 7;
K by N at position 7 and S by S at position 7;
K by N at position 7 and S by T at position 7;
A by N at position 7 and D by S at position 7;
A by N at position 7 and D by T at position 7;
D by N at position 7 and T by S at position 7;
D by N at position 7 and T by T at position 7;
I by N at position 10 and G by S at position 12;
I by N at position 10 and G by T at position 12;
Q by N at position 11 and V by S at position 13;
Q by N at position 11 and V by T at position 13;
G by N at position 12 and G by S at position 14;
G by N at position 12 and G by T at position 14;
V by N at position 13 and V by S at position 15;
V by N at position 13 and V by T at position 15;
G by N at position 14 and T by S at position 16;
G by N at position 14 and T by T at position 16;
V by N at position 15 and E by S at position 17;
V by N at position 15 and E by T at position 17;
T by N at position 16 and T by S at position 18;
T by N at position 16 and T by T at position 18;
E by N at position 17 and P by S at position 19;
E by N at position 17 and P by T at position 19;
T by N at position 18 and I by S at position 10;
T by N at position 18 and I by T at position 10;
K by N at position 14 and S by S at position 16;
K by N at position 14 and S by T at position 16;
S by N at position 14 and N by S at position 16;
S by N at position 14 and N by T at position 16;
T by N at position 15 and L by S at position 17;
T by N at position 15 and L by T at position 17;
N by N at position 16 and Q by S at position 18;
N by N at position 16 and Q by T at position 18;
L by N at position 17 and E by S at position 19;
L by N at position 17 and E by T at position 19;
Q by N at position 18 and S by S at position 10;
Q by N at position 18 and S by T at position 10;
E by N at position 19 and L by S at position 11;
E by N at position 19 and L by T at position 11;
S by N at position 10 and R by S at position 12;
S by N at position 10 and R by T at position 12;
L by N at position 11 and S by S at position 13;
L by N at position 11 and S by T at position 13;
R by N at position 12 and K by S at position 14;
R by N at position 12 and K by T at position 14;
S by N at position 13 and E by S at position 15; and/or
S by N at position 13 and E by T at position 15, where residue 1 corresponds to residue 1 of the mature IFNα-2b or IFNα-2a protein set forth in SEQ ID NO:12 or IFN-α2a (CAA23805):

(SEQ ID NO: 13)
Cys Asp Leu Pro Gln Thr His Ser Leu Gly Ser Arg

Arg Thr Leu Met Leu Leu Ala Gln Met Arg Lys Ile

Ser Leu Phe Ser Cys Leu Lys Asp Arg His Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu, respectively. In particular embodiments, the IFNα-2b or IFNα-2a mutant protein has increased resistance to proteolysis compared to unmodified IFNα-2b or IFNα-2a, and is selected from among proteins comprising one, or two, or three, or four, or five or more sets of duo-amino acid replacements in SEQ ID NO:12 corresponding to:
Q by N at position 5 and H by S at position 7;
P by N at position 3 and E by S at position 4;
P by N at position 3 and E by T at position 4;
Q by N at position 4 and E by S at position 4;
Q by N at position 4 and E by T at position 4;
E by N at position 4 and F by S at position 43;
E by N at position 4 and F by T at position 43;
F by N at position 43 and N by S at position 4;
G by N at position 4 and Q by T at position 4;
N by N at position 4 and F by S at position 4;
N by N at position 4 and F by T at position 4;
Q by N at position 4 and Q by S at position 4;
F by N at position 4 and K by S at position 4;
F by N at position 4 and K by T at position 4;
I by N at position 10 and G by S at position 12;
I by N at position 10 and G by T at position 12;
V by N at position 15 and E by S at position 17;
V by N at position 15 and E by T at position 17;
T by N at position 16 and T by S at position 18;
T by N at position 16 and T by T at position 18;
E by N at position 17 and P by S at position 19;
E by N at position 17 and P by T at position 19;
L by N at position 17 and E by S at position 19;
L by N at position 17 and E by T at position 19;
E by N at position 19 and L by S at position 11; and
E by N at position 19 and L by T at position 11.

In certain provided herein are IFNα-2b and IFNα-2a mutant proteins comprising one or more pseudo-wild type mutations at amino acid positions of IFNα-2b or IFNα-2a corresponding to SEQ ID NO:12 or SEQ ID NO: 13. Such pseudo-wild type mutations include 1, or 2, or 3, or 4, or 5, or more mutations at amino acid residues selected from the group consisting of 9, 10, 17, 20, 24, 25, 35, 37, 41, 52, 54, 56, 57, 58, 60, 63, 64, 65, 76, 89, and 90. The mutations can be either one or more of insertions, deletions and/or replacements of the native amino acid residue(s). In one embodiment, the pseudo-wild type replacements are mutations with alanine at each position. In another embodiment, the pseudo-wild type replacements are one or more mutations in SEQ ID NO: 12 corresponding to:

L by A at position 9, L by A at position 1;

Q by A at position 2, I by A at position 2;

S by A at position 2, D by A at position 3;

G by A at position 3, E by A at position 4;

T by A at position 5, P by A at position 5;

L by A at position 5, H by A at position 5;

E by A at position 5, I by A at position 6;

I by A at position 63, F by A at position 6;

N by A at position 6, W by A at position 7, and/or

Y by A at position 8, and Q by A at position 9.

In certain embodiments, the constructs described herein utilize an interferon showing a reduced activity (e.g., a decreased antiviral activity). In certain embodiments such interferons can comprise mutations at amino acid positions of IFNα-2b corresponding, amino acid residues: 2, 7, 8, 11, 13, 15, 16, 23, 26, 28, 29, 30, 31, 32, 33, 53, 69, 91, 93, 98, and/or 101 or to SEQ ID NO:12. Accordingly, in particular embodiments where it is desired to decrease the anti-viral activity of IFNα-2b or IFNα-2a, either one, or two, or three, or 4, or 5 or more of insertions, deletions and/or replacements of the native amino acid residue(s) can be carried out at one or more of amino acid positions of IFNα-2b or IFNα-2a corresponding to SEQ ID NO: 12, amino acid residues: 2, 7, 8, 11, 13, 15, 16, 23, 26, 28, 29, 30, 31, 32, 33, 53, 69, 91, 93, 98, and/or 101.

In certain embodiments, the modified IFNα cytokines are selected from among:

(a) a modified IFNα-2a that is human and is selected from among proteins comprising one, two, three, four, or 5 or more single amino acid replacements in SEQ ID NO:13, corresponding to amino acid positions: 41, 58, 78, 107, 117, 125, 133, and/or 159;

(b) a modified IFNα-c that is human and is selected from among proteins comprising one, two, three, four, or five or more single amino acid replacements in Genbank P01566, sequence:

```
                                        (SEQ ID NO: 14)
Cys Asp Leu Pro Gln Thr His Ser Leu Gly Asn Arg

Arg Ala Leu Ile Leu Leu Gly Gln Met Gly Arg Ile

Ser Pro Phe Ser Cys Leu Lys Asp Arg His Asp Phe

Arg Ile Pro Gln Glu Glu Phe Asp Gly Asn Gln Phe

Gln Lys Ala Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Ser Ile Leu Ala Val
```

-continued
```
Arg Lys Tyr Phe Gln Arg Ile Thr Leu Tyr Leu Ile

Glu Arg Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp
``` corresponding to amino acid positions: 41, 59, 79, 108, 118, 126, 134, and/or 160;

(c) a modified IFNα-2c cytokine that is human and is selected from among cytokines comprising one, two, three, four, or five or more amino acid replacements in the sequence:

```
                                        (SEQ ID NO: 15)
Cys Asp Leu Pro Gln Thr His Ser Leu Gly Ser Arg

Arg Thr Leu Met Leu Leu Ala Gln Met Arg Arg Ile

Ser Leu Phe Ser Cys Leu Lys Asp Arg Arg Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu
``` corresponding to amino acid positions: 41, 58, 78, 107, 117, 125, 133, and/or 159;

(d) an IFNα-d modified protein that is human and is selected from among proteins comprising one, or two, or three, or four, or five or more single amino acid replacements in Genbank AAB59403 sequence:

```
                                        (SEQ ID NO: 16)
Cys Asp Leu Pro Glu Thr His Ser Leu Asp Asn Arg

Arg Thr Leu Met Leu Leu Ala Gln Met Ser Arg Ile

Ser Pro Ser Ser Cys Leu Met Asp Arg His Asp Phe

Gly Phe Pro Gln Glu Glu Phe Asp Gly Asn Gln Phe

Gln Lys Ala Pro Ala Ile Ser Val Leu His Glu Leu

Ile Gln Gln Ile Phe Asn Leu Phe Thr Thr Lys Asp

Ser Ser Ala Ala Trp Asp Glu Asp Leu Leu Asp Lys

Phe Cys Thr Glu Leu Tyr Gln Gln Leu Asn Asp Leu

Glu Ala Cys Val Met Gln Glu Glu Arg Val Gly Glu

Thr Pro Leu Met Asn Ala Asp Ser Ile Leu Ala Val

Lys Lys Tyr Phe Arg Arg Ile Thr Leu Tyr Leu Thr

Glu Lys Lys Tyr Ser Pro Cys Ala Trp Glu Val Val
```

-continued

Arg Ala Glu Ile Met Arg Ser Leu Ser Leu Ser Thr

Asn Leu Gln Glu Arg Leu Arg Arg Lys Glu corresponding to amino acid positions: 41, 59, 79, 108, 118, 126, 134, and/or 160;

(e) an IFNα-5 modified protein that is human and is selected from among proteins comprising one, or two, or three, or four, or five or more single amino acid replacements in Genbank CAA26702 sequence:

(SEQ ID NO: 17)
Cys Asp Leu Pro Gln Thr His Ser Leu Ser Asn Arg

Arg Thr Leu Met Ile Met Ala Gln Met Gly Arg Ile

Ser Pro Phe Ser Cys Leu Lys Asp Arg His Asp Phe

Gly Phe Pro Gln Glu Glu Phe Asp Gly Asn Gln Phe

Gln Lys Ala Gln Ala Ile Ser Val Leu His Glu Met

Ile Gln Gln Thr Phe Asn Leu Phe Ser Thr Lys Asp

Ser Ser Ala Thr Trp Asp Glu Thr Leu Leu Asp Lys

Phe Tyr Thr Glu Leu Tyr Gln Gln Leu Asn Asp Leu

Glu Ala Cys Met Met Gln Glu Val Gly Val Glu Asp

Thr Pro Leu Met Asn Val Asp Ser Ile Leu Thr Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Phe Ser Leu Ser Ala

Asn Leu Gln Glu Arg Leu Arg Arg Lys Glu corresponding to amino acid positions: 41, 59, 79, 108, 118, 126, 134, and/or 160;

(f) an IFNα-6 modified protein that is human and is selected from among proteins comprising one, or two, or three, or four, or five or more single amino acid replacements in Genbank CAA26704 sequence:

(SEQ ID NO: 18)

Cys Asp Leu Pro Gln Thr His Ser Leu Gly His Arg

Arg Thr Met Met Leu Leu Ala Gln Met Arg Arg Ile

Ser Leu Phe Ser Cys Leu Lys Asp Arg His Asp Phe

Arg Phe Pro Gln Glu Glu Phe Asp Gly Asn Gln Phe

Gln Lys Ala Glu Ala Ile Ser Val Leu His Glu Val

Ile Gln Gln Thr Phe Asn Leu Phe Ser Thr Lys Asp

Ser Ser Val Ala Trp Asp Glu Arg Leu Leu Asp Lys

Leu Tyr Thr Glu Leu Tyr Gln Gln Leu Asn Asp Leu

Glu Ala Cys Val Met Gln Glu Val Trp Val Gly Gly

Thr Pro Leu Met Asn Glu Asp Ser Ile Leu Ala Val

Arg Lys Tyr Phe Gln Arg Ile Thr Leu Tyr Leu Thr

-continued

Glu Lys Lys Tyr Ser Pro Cys Ala Trp Glu Val Val

Arg Ala Glu Ile Met Arg Ser Phe Ser Ser Ser Arg

Asn Leu Gln Glu Arg Leu Arg Arg Lys Glu corresponding to amino acid positions: 41, 59, 79, 108, 118, 126, 134, and/or 160;

(g) an IFNα-4 modified protein that is human and is selected from among proteins comprising one, or two, or three, or four, or five or more single amino acid replacements in Genbank NP_066546 sequence:

(SEQ ID NO: 19)

Cys Asp Leu Pro Gln Thr His Ser Leu Gly Asn Arg

Arg Ala Leu Ile Leu Leu Ala Gln Met Gly Arg Ile

Ser His Phe Ser Cys Leu Lys Asp Arg His Asp Phe

Gly Phe Pro Glu Glu Glu Phe Asp Gly His Gln Phe

Gln Lys Ala Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(h) an IFNα-4b modified protein that is human and is selected from among proteins comprising one, or two, or three, or four, or five or more single amino acid replacements in Genbank CAA26701 sequence:

(SEQ ID NO: 20)

Cys Asp Leu Pro Gln Thr His Ser Leu Gly Asn Arg

Arg Ala Leu Ile Leu Leu Ala Gln Met Gly Arg Ile

Ser His Phe Ser Cys Leu Lys Asp Arg His Asp Phe

Gly Phe Pro Glu Glu Glu Phe Asp Gly His Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Val Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(i) the IFNα-I modified protein that is human and is selected from among proteins comprising one, or two, or three, or four, or five or more single amino acid replacements in Genbank AAA52725 sequence:

(SEQ ID NO: 21)
Cys Asp Leu Pro Gln Thr His Ser Leu Gly Asn Arg

Arg Ala Leu Ile Leu Leu Ala Gln Met Gly Arg Ile

Ser Pro Phe Ser Cys Leu Lys Asp Arg His Asp Phe

Gly Leu Pro Gln Glu Glu Phe Asp Gly Asn Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asn Leu

Glu Ala Cys Val Ile Gln Glu Val Gly Met Glu Glu

Thr Pro Leu Met Asn Glu Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Ile Leu Arg Arg Lys Asp corresponding to amino acid positions: 41, 59, 79, 108, 118, 126, 134, and/or 160;

(j) an IFNα-J modified protein that is human and is selected from among proteins comprising one, or two, or three, or four, or five or more single amino acid replacements in Genbank CAA23792 sequence:

(SEQ ID NO: 22)
Cys Asp Leu Pro Gln Thr His Ser Leu Arg Asn Arg

Arg Ala Leu Ile Leu Leu Ala Gln Met Gly Arg Ile

Ser Pro Phe Ser Cys Leu Lys Asp Arg His Glu Phe

Arg Phe Pro Glu Glu Glu Phe Asp Gly His Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Phe Ile Leu Ala Val

Arg Lys Tyr Phe Gln Arg Ile Thr Leu Tyr Leu Met

Glu Lys Lys Tyr Ser Pro Cys Ala Trp Glu Val Val

Arg Ala Glu Ile Met Arg Ser Phe Ser Phe Ser Thr

Asn Leu Lys Lys Gly Leu Arg Arg Lys Asp corresponding to amino acid positions: 41, 59, 79, 108, 118, 126, 134, and/or 160;

(k) an IFNα-H modified protein that is human and is selected from among proteins comprising one, or two, or three, or four, or five or more single amino acid replacements in Genbank CAA23794 sequence:

(SEQ ID NO: 23)
Cys Asn Leu Ser Gln Thr His Ser Leu Asn Asn Arg

Arg Thr Leu Met Leu Met Ala Gln Met Arg Arg Ile

Ser Pro Phe Ser Cys Leu Lys Asp Arg His Asp Phe

Glu Phe Pro Gln Glu Glu Phe Asp Gly Asn Gln Phe

Gln Lys Ala Gln Ala Ile Ser Val Leu His Glu Met

Met Gln Gln Thr Phe Asn Leu Phe Ser Thr Lys Asn

Ser Ser Ala Ala Trp Asp Glu Thr Leu Leu Glu Lys

Phe Tyr Ile Glu Leu Phe Gln Gln Met Asn Asp Leu

Glu Ala Cys Val Ile Gln Glu Val Gly Val Glu Glu

Thr Pro Leu Met Asn Glu Asp Ser Ile Leu Ala Val

Lys Lys Tyr Phe Gln Arg Ile Thr Leu Tyr Leu Met

Glu Lys Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(l) an IFNα-F modified protein that is human and is selected from among proteins comprising one, or two, or three, or four, or five or more single amino acid replacements in Genbank AAA52718 sequence:

(SEQ ID NO: 24)
Cys Asp Leu Pro Gln Thr His Ser Leu Gly Asn Arg

Arg Ala Leu Ile Leu Leu Ala Gln Met Gly Arg Ile

Ser Pro Phe Ser Cys Leu Lys Asp Arg His Asp Phe

Gly Phe Pro Gln Glu Glu Phe Asp Gly Asn Gln Phe

Gln Lys Ala Gln Ala Ile Ser Val Leu His Glu Met

Ile Gln Gln Thr Phe Asn Leu Phe Ser Thr Lys Asp

Ser Ser Ala Thr Trp Glu Gln Ser Leu Leu Glu Lys

Phe Ser Thr Glu Leu Asn Gln Gln Leu Asn Asp Leu

Glu Ala Cys Val Ile Gln Glu Val Gly Val Glu Glu

Thr Pro Leu Met Asn Val Asp Ser Ile Leu Ala Val

Lys Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Phe Ser Leu Ser Lys

Ile Phe Gln Glu Arg Leu Arg Arg Lys Glu corresponding to amino acid positions: 41, 59, 79, 108, 118, 126, 134, and/or 160;

(m) an IFNα-8 modified protein that is human and is selected from among proteins comprising one, or two, or three, or four, or five or more single amino acid replacements in Genbank CAA26903, sequence:

```
                                          (SEQ ID NO: 25)
Cys Asp Leu Pro Gln Thr His Ser Leu Gly Asn Arg

Arg Ala Leu Ile Leu Leu Ala Gln Met Arg Arg Ile

Ser Pro Phe Ser Cys Leu Lys Asp Arg His Asp Phe

Glu Phe Pro Gln Glu Glu Phe Asp Asp Lys Gln Phe

Gln Lys Ala Gln Ala Ile Ser Val Leu His Glu Met

Ile Gln Gln Thr Phe Asn Leu Phe Ser Thr Lys Asp

Ser Ser Ala Ala Leu Asp Glu Thr Leu Leu Asp Glu

Phe Tyr Ile Glu Leu Asp Gln Gln Leu Asn Asp Leu

Glu Ser Cys Val Met Gln Glu Val Gly Val Ile Glu

Ser Pro Leu Met Tyr Glu Asp Ser Ile Leu Ala Val

Arg Lys Tyr Phe Gln Arg Ile Thr Leu Tyr Leu Thr

Glu Lys Lys Tyr Ser Ser Cys Ala Trp Glu Val Val

Arg Ala Glu Ile Met Arg Ser Phe Ser Leu Ser Ile

Asn Leu Gln Lys Arg Leu Lys Ser Lys Glu
``` corresponding to amino acid positions: 41, 59, 79, 108, 118, 126, 134, and/or 160; and/or (n) an IFNα-consensus modified protein sequence that is human and is selected from among proteins that contain one, or two, or three, or four, or five or more single amino acid replacements in the consensus sequence:

```
                                          (SEQ ID NO: 26)
Cys Asp Leu Pro Gln Thr His Ser Leu Gly Asn Arg

Arg Ala Leu Ile Leu Leu Ala Gln Met Arg Arg Ile

Ser Pro Phe Ser Cys Leu Lys Asp Arg His Asp Phe

Gly Pro Gln Glu Glu Phe Asp Gly Asn Gln Phe Gln

Lys Ala Gln Ala Ile Ser Val Leu His Glu Met Ile

Gln Gln Thr Phe Asn Leu Phe Ser Thr Lys Asp Ser

Ser Ala Ala Trp Asp Glu Ser Leu Leu Glu Lys Phe

Tyr Thr Glu Leu Tyr Gln Gln Leu Asn Asp Leu Glu

Ala Cys Val Ile Gln Glu Val Gly Val Glu Glu Thr

Pro Leu Met Asn Val Asp Ser Ile Leu Ala Val Lys

Lys Tyr Phe Gln Arg Ile Thr Leu Tyr Leu Thr Glu

Lys Lys Tyr Ser Pro Cys Ala Trp Glu Val Val Arg

Ala Glu Ile Met Arg Ser Phe Ser Leu Ser Thr Asn

Leu Gln Glu Arg Leu Arg Arg Lys Glu
``` corresponding to amino acid positions: 41, 58, 78, 107, 117, 125, 133, and/or 159.

Also contemplated are modified IFNβ cytokines, comprising mutations at one, or two, or three, or four, or five or more amino acid residues of IFNβ (GENBANK AAC41702) sequence:

```
                                          (SEQ ID NO: 27)
Met Ser Tyr Asn Leu Leu Gly Phe Leu Gln Arg Ser

Ser Asn Phe Gln Cys Gln Lys Leu Leu Trp Gln Leu

Asn Gly Arg Leu Glu Tyr Cys Leu Lys Asp Arg Met

Asn Phe Asp Ile Pro Glu Glu Ile Lys Gln Leu Gln

Gln Phe Gln Lys Glu Asp Ala Ala Leu Thr Ile Tyr

Glu Met Leu Gln Asn Ile Phe Ala Ile Phe Arg Gln

Asp Ser Ser Ser Thr Gly Trp Asn Glu Thr Ile Val

Glu Asn Leu Leu Ala Asn Val Tyr His Gln Ile Asn

His Leu Lys Thr Val Leu Glu Glu Lys Leu Glu Lys

Glu Asp Phe Thr Arg Gly Lys Leu Met Ser Ser Leu

His Leu Lys Arg Tyr Tyr Gly Arg Ile Leu His Tyr

Leu Lys Ala Lys Glu Tyr Ser His Cys Ala Trp Thr

Ile Val Arg Val Glu Ile Leu Arg Asn Phe Tyr Phe

Ile Asn Arg Leu Thr Gly Tyr Leu Arg Asn
``` corresponding to one, two, three, four, or five or more positions selected from the group consisting of position 16: 39, 42, 45, 47, 52, 67, 71, 73, 81, 107, 108, 109, 110, 111, 113, 116, 120, 123, 124, 128, 130, 134, 136, 137, 163, and 165. The mutations include insertions, deletions and replacements of the native amino acid residue(s). In particular embodiments, the replacements are selected from among amino acid substitutions in SEQ ID NO:27 set forth in FIG. 12A of U.S. Pat. No. 7,998,469 B2, where the first amino acid indicated is substituted by the second at the position indicated for all of the substitutions set forth in FIG. 12A through 12T of U.S. Pat. No. 7,998,469 B2 which is incorporated herein by reference for the substitutions set for in FIGS. 12a through 12T therein.

In various embodiments proteinase resistant modified interferon-beta polypeptides as described in U.S. Pat. No. 8,052,964 B2 are also contemplated. Certain illustrative modified IFN-β molecules differ from an unmodified IFN beta by two amino acid substitutions where the unmodified IFN beta cytokine comprises the amino acid sequence of IFN-β (Genbank AAC41702, SEQ ID NO:27) and the two amino acid substitutions are selected from the group consisting of substitution of the 5th and 6th positions in SEQ ID NO:27, with aspartic acid and glutamine, respectively; or substitution of the 5th and 6th positions in SEQ ID NO:27, with glutamine; or substitution of the 5th and 6th positions in SEQ ID NO:27, with asparagine and glutamine, respectively; or substitution of the 6th and 36th positions in SEQ ID NO:27, with glutamine and isoleucine, respectively; or substitution of the 6th and 86th positions in SEQ ID NO:27, with glutamine where the two amino acid substitutions confer increased resistance to proteolysis over the unmodified IFN beta.

In certain embodiments the use of an interferon gamma (designated IFNγ or IFN-γ), a truncated IFN-γ, or a mutant IFN-γ is contemplated.

Interferon-gamma (IFNγ) is a cytokine produced by T-lymphocytes and natural killer cells and exists as a homodimer of two noncovalently bound polypeptide subunits. The mature form of each dimer comprises 143 amino acid residues (shown in SEQ ID NO:28):

```
                                      (SEQ ID NO: 28)
DPYVKEAENL KKYFNAGHSD VADNGTLFLG ILKNWKEESD

RKIMQSQIVS FYFKLFKNFK DDQSIQKSVE TIKEDMNVKF

FNSNKKKRDDF EKLTNYSVT DLNVQRKAIH ELIQVMAELS

PAAKTGKRKR SQMLFQGRRAS Q
```

Each subunit has two potential N-glycosylation sites (Aggarwal et al. (1992) *Human Cytokines*, Blackwell Scientific Publications) at positions 25 and 97. Depending on the degree of glycosylation the molecular weight of IFNG in dimer form is 34-50 kDa (Farrar et al. (1993) *Ann. Rev. Immunol*, 11: 571-611).

The primary sequence of wildtype human IFNG (huIFNγG) was reported by Gray et al. (1982) *Nature* 298: 859-863), Taya et al. (1982) *EMBO J.* 1: 953-958; Devos et al. (1982) *Nucleic Acids Res.* 10: 2487-2501; and Rinderknecht et al. (1984) *J. Biol. Chem.* 259: 6790-6797), and in EP 77670, EP 89676 and EP 110044. The 3D structure of huIFNG was reported by Ealick et al. (1991) *Science* 252: 698-702, 1991).

Various naturally-occurring or mutated forms of the IFNG subunit polypeptides have been reported, including one comprising a Cys-Tyr-Cys N-terminal amino acid sequence (positions (−3)-(−1) relative to SEQ ID NO:28), one comprising an N-terminal methionine (position −1 relative to SEQ ID NO:28), and various C-terminally truncated forms comprising 127-134 amino acid residues. It is known that 1-15 amino acid residues may be deleted from the C-terminus without abolishing IFNγ activity of the molecule. Furthermore, heterogeneity of the huIFNγ C-terminus was described by Pan et al. (1987) *Eur. J. Biochem.* 166: 145-149.

HuIFNγ muteins were reported by Slodowski et al. (1991) *Eur. J. Biochem.* 202:1133-1140, 1991, Luk et al. (1990) *J. Biol. Chem.* 265: 13314-13319, Seelig et al., (1988) *Biochemistry* 27: 1981-1987, Trousdale et al. (1985) *Invest. Ophthalmol. Vis. Sci.* 26: 1244-1251, and in EP 146354.

WO 1992/008737 discloses IFNγ variants comprising an added methionine in the N-terminal end of the full (residues 1-143) or partial (residues 1-132) amino acid sequence of wildtype human IFNG. EP 219 781 discloses partial huIFNγ sequences comprising amino 10 acid residues 3-124 (of SEQ ID NO:28)). U.S. Pat. No. 4,832,959 discloses partial huIFNG sequences comprising residues 1-127, 5-146 and 5-127 of an amino acid sequence that compared to SEQ ID NO 2 has three additional N-terminal amino acid residues (CYC). U.S. Pat. No. 5,004,689 discloses a DNA sequence encoding huIFNG without the 3 N-terminal amino acid residues CYC and its expression in *E. coli*. EP 446582 discloses *E. coli* produced rhuIFNG free of an 15 N-terminal methionine. U.S. Pat. No. 6,120,762 discloses a peptide fragment of huIFNγ comprising residues 95-134 thereof (relative to SEQ ID NO:28).

In various embodiments where interferon gamma is utilized in the constructs described herein the interferon gamma component(s) of the construct can be any polypeptide with IFNγ activity, and thus be derived from any origin, e.g. a non-human mammalian origin. However, in various embodiments, it is preferred that the parent polypeptide is huIFNγ, e.g., with the amino acid sequence shown in SEQ ID NO:28, or a variant or fragment thereof.

Examples of variants of hIFNγ that can be incorporated in the constructs contemplated herein described above, and include, but are not limited to, e.g. huIFNγ with the N-terminal addition CYC, the cysteine modified variants described in U.S. Pat. No. 6,046,034, and the like. Specific examples of fragments are those described above, and include, but are not limited to huIFNγ C-terminally truncated with 1-15 amino acid residues, e.g. with 1, 2, 3, 4, 5, 6, 7, 8, 9, 10, 11, 12, 13, 14, or 15 amino acid residues, and/or N-terminally truncated with 1-3 amino acid residues. In one illustrative, but non-limiting embodiment, the interferon comprises a truncated interferon consisting of the amino acid sequence:

```
                                      (SEQ ID NO: 29)
DPYVKEAENL KKYFNAGHSD VADNGTLFLG ILKNWKEESD

RKIMQSQIVS FYFKLFKNFK DDQSIQKSVE TIKEDMNVKF

FNSNKKKRDD FEKLTNYSVT DLNVQRKAIH ELIQVMAELS

PAAKTGKRKR SQM
```

In certain embodiments the use of chemically modified interferon is also contemplated. For example, in certain embodiments, the interferon is chemically modified to increase serum half-life. Thus, for example, (2-sulfo-9-fluorenylmethoxycarbonyl)$_7$-interferon-α2 undergoes time-dependent spontaneous hydrolysis, generating active interferon (see, e.g., Shechter et al. (2001) *Proc. Natl. Acad. Sci., USA*, 98(3): 1212-1217). Other modifications, include for example, N-terminal modifications in including, but not limited to the addition of PEG, protecting groups, and the like. U.S. Pat. No. 5,824,784, for example, described N-terminally chemically modified interferon.

TABLE 4

Illustrative, but non-limiting antibody-interferon combinations contemplated for use in the constructs described herein. Where the antibody is listed, the native antibody, chimeric antibodies, humanized antibodies, single chain antibodies are contemplated in addition to full-length immunoglobulins (e.g., IgE, IgG, IgM, IgA, etc.).

| Interferon | Attached Antibody | | | | | | | |
|---|---|---|---|---|---|---|---|---|
| IFN-α1 | 9.2.27 | 225.28 | 225.28s | 763.74 | VF1-TP41.2 | VT80.1 | 653.25 | 763.74 | TP61.5 |
| IFN-α1 | 9.2.27 | 225.28 | 225.28s | 763.74 | VF1-TP41.2 | VT80.1 | 653.25 | 763.74 | TP61.5 |
| IFN-α13 | 9.2.27 | 225.28 | 225.28s | 763.74 | VF1-TP41.2 | VT80.1 | 653.25 | 763.74 | TP61.5 |
| IFN-α14 | 9.2.27 | 225.28 | 225.28s | 763.74 | VF1-TP41.2 | VT80.1 | 653.25 | 763.74 | TP61.5 |
| IFN-α16 | 9.2.27 | 225.28 | 225.28s | 763.74 | VF1- | VT80.1 | 653.25 | 763.74 | TP61.5 |

TABLE 4-continued

Illustrative, but non-limiting antibody-interferon combinations contemplated for use in the constructs described herein. Where the antibody is listed, the native antibody, chimeric antibodies, humanized antibodies, single chain antibodies are contemplated in addition to full-length immunoglobulins (e.g., IgE, IgG, IgM, IgA, etc.).

| Interferon | Attached Antibody | | | | | | | | |
|---|---|---|---|---|---|---|---|---|---|
| IFN-α17 | 9.2.27 | 225.28 | 225.28s | 763.74 | VF1-TP41.2 TP41.2 | VT80.1 | 653.25 | 763.74 | TP61.5 |
| IFN-α2 | 9.2.27 | 225.28 | 225.28s | 763.74 | VF1-TP41.2 | VT80.1 | 653.25 | 763.74 | TP61.5 |
| IFN-α21 | 9.2.27 | 225.28 | 225.28s | 763.74 | VF1-TP41.2 | VT80.1 | 653.25 | 763.74 | TP61.5 |
| IFN-α22 | 9.2.27 | 225.28 | 225.28s | 763.74 | VF1-TP41.2 | VT80.1 | 653.25 | 763.74 | TP61.5 |
| IFN-α2a | 9.2.27 | 225.28 | 225.28s | 763.74 | VF1-TP41.2 | VT80.1 | 653.25 | 763.74 | TP61.5 |
| IFN-α2b | 9.2.27 | 225.28 | 225.28s | 763.74 | VF1-TP41.2 | VT80.1 | 653.25 | 763.74 | TP61.5 |
| IFN-α4a | 9.2.27 | 225.28 | 225.28s | 763.74 | VF1-TP41.2 | VT80.1 | 653.25 | 763.74 | TP61.5 |
| IFN-α4b | 9.2.27 | 225.28 | 225.28s | 763.74 | VF1-TP41.2 | VT80.1 | 653.25 | 763.74 | TP61.5 |
| IFN-α5 | 9.2.27 | 225.28 | 225.28s | 763.74 | VF1-TP41.2 | VT80.1 | 653.25 | 763.74 | TP61.5 |
| IFN-α54 | 9.2.27 | 225.28 | 225.28s | 763.74 | VF1-TP41.2 | VT80.1 | 653.25 | 763.74 | TP61.5 |
| IFN-α6 | 9.2.27 | 225.28 | 225.28s | 763.74 | VF1-TP41.2 | VT80.1 | 653.25 | 763.74 | TP61.5 |
| IFN-α61 | 9.2.27 | 225.28 | 225.28s | 763.74 | VF1-TP41.2 | VT80.1 | 653.25 | 763.74 | TP61.5 |
| IFN-α61 | 9.2.27 | 225.28 | 225.28s | 763.74 | VF1-TP41.2 | VT80.1 | 653.25 | 763.74 | TP61.5 |
| IFN-α7 | 9.2.27 | 225.28 | 225.28s | 763.74 | VF1-TP41.2 | VT80.1 | 653.25 | 763.74 | TP61.5 |
| IFN-α74 | 9.2.27 | 225.28 | 225.28s | 763.74 | VF1-TP41.2 | VT80.1 | 653.25 | 763.74 | TP61.5 |
| IFNα76 | 9.2.27 | 225.28 | 225.28s | 763.74 | VF1-TP41.2 | VT80.1 | 653.25 | 763.74 | TP61.5 |
| IFN-α8 | 9.2.27 | 225.28 | 225.28s | 763.74 | VF1-TP41.2 | VT80.1 | 653.25 | 763.74 | TP61.5 |
| IFN-α88 | 9.2.27 | 225.28 | 225.28s | 763.74 | VF1-TP41.2 | VT80.1 | 653.25 | 763.74 | TP61.5 |
| IFN-αA | 9.2.27 | 225.28 | 225.28s | 763.74 | VF1-TP41.2 | VT80.1 | 653.25 | 763.74 | TP61.5 |
| IFN-αB | 9.2.27 | 225.28 | 225.28s | 763.74 | VF1-TP41.2 | VT80.1 | 653.25 | 763.74 | TP61.5 |
| IFN-αB2 | 9.2.27 | 225.28 | 225.28s | 763.74 | VF1-TP41.2 | VT80.1 | 653.25 | 763.74 | TP61.5 |
| IFN-αC | 9.2.27 | 225.28 | 225.28s | 763.74 | VF1-TP41.2 | VT80.1 | 653.25 | 763.74 | TP61.5 |
| IFN-αD | 9.2.27 | 225.28 | 225.28s | 763.74 | VF1-TP41.2 | VT80.1 | 653.25 | 763.74 | TP61.5 |
| IFN-αF | 9.2.27 | 225.28 | 225.28s | 763.74 | VF1-TP41.2 | VT80.1 | 653.25 | 763.74 | TP61.5 |
| IFN-αG | 9.2.27 | 225.28 | 225.28s | 763.74 | VF1-TP41.2 | VT80.1 | 653.25 | 763.74 | TP61.5 |
| IFN-αGX-1 | 9.2.27 | 225.28 | 225.28s | 763.74 | VF1-TP41.2 | VT80.1 | 653.25 | 763.74 | TP61.5 |
| IFN-αH | 9.2.27 | 225.28 | 225.28s | 763.74 | VF1-TP41.2 | VT80.1 | 653.25 | 763.74 | TP61.5 |
| IFN-αH1 | 9.2.27 | 225.28 | 225.28s | 763.74 | VF1-TP41.2 | VT80.1 | 653.25 | 763.74 | TP61.5 |
| IFN-αJ | 9.2.27 | 225.28 | 225.28s | 763.74 | VF1-TP41.2 | VT80.1 | 653.25 | 763.74 | TP61.5 |
| IFN-αJ1 | 9.2.27 | 225.28 | 225.28s | 763.74 | VF1-TP41.2 | VT80.1 | 653.25 | 763.74 | TP61.5 |
| IFN-αK | 9.2.27 | 225.28 | 225.28s | 763.74 | VF1-TP41.2 | VT80.1 | 653.25 | 763.74 | TP61.5 |
| IFN-αM | 9.2.27 | 225.28 | 225.28s | 763.74 | VF1-TP41.2 | VT80.1 | 653.25 | 763.74 | TP61.5 |
| IFN-αO | 9.2.27 | 225.28 | 225.28s | 763.74 | VF1-TP41.2 | VT80.1 | 653.25 | 763.74 | TP61.5 |
| IFN-αWA | 9.2.27 | 225.28 | 225.28s | 763.74 | VF1-TP41.2 | VT80.1 | 653.25 | 763.74 | TP61.5 |
| INF-α2c | 9.2.27 | 225.28 | 225.28s | 763.74 | VF1-TP41.2 | VT80.1 | 653.25 | 763.74 | TP61.5 |
| IFN-β | 9.2.27 | 225.28 | 225.28s | 763.74 | VF1-TP41.2 | VT80.1 | 653.25 | 763.74 | TP61.5 |

TABLE 4-continued

Illustrative, but non-limiting antibody-interferon combinations contemplated for use in the constructs described herein. Where the antibody is listed, the native antibody, chimeric antibodies, humanized antibodies, single chain antibodies are contemplated in addition to full-length immunoglobulins (e.g., IgE, IgG, IgM, IgA, TABLE 4-continued Illustrative, but non-limiting antibody-interferon combinations contemplated for
use in the constructs described herein. Where the antibody is listed, the native antibody,
chimeric antibodies, humanized antibodies, single chain antibodies are contemplated in
addition to full-length immunoglobulins (e.g., IgE, IgG, IgM, IgA, etc.).

| Interferon | Attached Antibody | | | | | | | |
|---|---|---|---|---|---|---|---|---|
| IFN-α1 | T8-203 | 149.53 | 225.28 | 763.74 | TP61.5 | VF1-TP34 | VF1-TP41.2 | MEL-14 | MEL-5 |
| IFN-α13 | T8-203 | 149.53 | 225.28 | 763.74 | TP61.5 | VF1-TP34 | VF1-TP41.2 | MEL-14 | MEL-5 |
| IFN-α14 | T8-203 | 149.53 | 225.28 | 763.74 | TP61.5 | VF1-TP34 | VF1-TP41.2 | MEL-14 | MEL-5 |
| IFN-α16 | T8-203 | 149.53 | 225.28 | 763.74 | TP61.5 | VF1-TP34 | VF1-TP41.2 | MEL-14 | MEL-5 |
| IFN-α17 | T8-203 | 149.53 | 225.28 | 763.74 | TP61.5 | VF1-TP34 | VF1-TP41.2 | MEL-14 | MEL-5 |
| IFN-α2 | T8-203 | 149.53 | 225.28 | 763.74 | TP61.5 | VF1-TP34 | VF1-TP41.2 | MEL-14 | MEL-5 |
| IFN-α21 | T8-203 | 149.53 | 225.28 | 763.74 | TP61.5 | VF1-TP34 | VF1-TP41.2 | MEL-14 | MEL-5 |
| IFN-α22 | T8-203 | 149.53 | 225.28 | 763.74 | TP61.5 | VF1-TP34 | VF1-TP41.2 | MEL-14 | MEL-5 |
| IFN-α2a | T8-203 | 149.53 | 225.28 | 763.74 | TP61.5 | VF1-TP34 | VF1-TP41.2 | MEL-14 | MEL-5 |
| IFN-α2b | T8-203 | 149.53 | 225.28 | 763.74 | TP61.5 | VF1-TP34 | VF1-TP41.2 | MEL-14 | MEL-5 |
| IFN-α4a | T8-203 | 149.53 | 225.28 | 763.74 | TP61.5 | VF1-TP34 | VF1-TP41.2 | MEL-14 | MEL-5 |
| IFN-α4b | T8-203 | 149.53 | 225.28 | 763.74 | TP61.5 | VF1-TP34 | VF1-TP41.2 | MEL-14 | MEL-5 |
| IFN-α5 | T8-203 | 149.53 | 225.28 | 763.74 | TP61.5 | VF1-TP34 | VF1-TP41.2 | MEL-14 | MEL-5 |
| IFN-α54 | T8-203 | 149.53 | 225.28 | 763.74 | TP61.5 | VF1-TP34 | VF1-TP41.2 | MEL-14 | MEL-5 |
| IFN-α6 | T8-203 | 149.53 | 225.28 | 763.74 | TP61.5 | VF1-TP34 | VF1-TP41.2 | MEL-14 | MEL-5 |
| IFN-α61 | T8-203 | 149.53 | 225.28 | 763.74 | TP61.5 | VF1-TP34 | VF1-TP41.2 | MEL-14 | MEL-5 |
| IFN-α61 | T8-203 | 149.53 | 225.28 | 763.74 | TP61.5 | VF1-TP34 | VF1-TP41.2 | MEL-14 | MEL-5 |
| IFN-α7 | T8-203 | 149.53 | 225.28 | 763.74 | TP61.5 | VF1-TP34 | VF1-TP41.2 | MEL-14 | MEL-5 |
| IFN-α74 | T8-203 | 149.53 | 225.28 | 763.74 | TP61.5 | VF1-TP34 | VF1-TP41.2 | MEL-14 | MEL-5 |
| IFNα76 | T8-203 | 149.53 | 225.28 | 763.74 | TP61.5 | VF1-TP34 | VF1-TP41.2 | MEL-14 | MEL-5 |
| IFN-α8 | T8-203 | 149.53 | 225.28 | 763.74 | TP61.5 | VF1-TP34 | VF1-TP41.2 | MEL-14 | MEL-5 |
| IFN-α88 | T8-203 | 149.53 | 225.28 | 763.74 | TP61.5 | VF1-TP34 | VF1-TP41.2 | MEL-14 | MEL-5 |
| IFN-αA | T8-203 | 149.53 | 225.28 | 763.74 | TP61.5 | VF1-TP34 | VF1-TP41.2 | MEL-14 | MEL-5 |
| IFN-αB | T8-203 | 149.53 | 225.28 | 763.74 | TP61.5 | VF1-TP34 | VF1-TP41.2 | MEL-14 | MEL-5 |
| IFN-αB2 | T8-203 | 149.53 | 225.28 | 763.74 | TP61.5 | VF1-TP34 | VF1-TP41.2 | MEL-14 | MEL-5 |
| IFN-αC | T8-203 | 149.53 | 225.28 | 763.74 | TP61.5 | VF1-TP34 | VF1-TP41.2 | MEL-14 | MEL-5 |
| IFN-αD | T8-203 | 149.53 | 225.28 | 763.74 | TP61.5 | VF1-TP34 | VF1-TP41.2 | MEL-14 | MEL-5 |
| IFN-αF | T8-203 | 149.53 | 225.28 | 763.74 | TP61.5 | VF1-TP34 | VF1-TP41.2 | MEL-14 | MEL-5 |
| IFN-αG | T8-203 | 149.53 | 225.28 | 763.74 | TP61.5 | VF1-TP34 | VF1-TP41.2 | MEL-14 | MEL-5 |
| IFN-αGX-1 | T8-203 | 149.53 | 225.28 | 763.74 | TP61.5 | VF1-TP34 | VF1-TP41.2 | MEL-14 | MEL-5 |
| IFN-αH | T8-203 | 149.53 | 225.28 | 763.74 | TP61.5 | VF1-TP34 | VF1-TP41.2 | MEL-14 | MEL-5 |
| IFN-αH1 | T8-203 | 149.53 | 225.28 | 763.74 | TP61.5 | VF1-TP34 | VF1-TP41.2 | MEL-14 | MEL-5 |
| IFN-αJ | T8-203 | 149.53 | 225.28 | 763.74 | TP61.5 | VF1-TP34 | VF1-TP41.2 | MEL-14 | MEL-5 |
| IFN-αJ1 | T8-203 | 149.53 | 225.28 | 763.74 | TP61.5 | VF1-TP34 | VF1-TP41.2 | MEL-14 | MEL-5 |
| IFN-αK | T8-203 | 149.53 | 225.28 | 763.74 | TP61.5 | VF1-TP34 | VF1-TP41.2 | MEL-14 | MEL-5 |

TABLE 4-continued

Illustrative, but non-limiting antibody-interferon combinations contemplated for use in the constructs described herein. Where the antibody is listed, the native antibody, chimeric antibodies, humanized antibodies, single chain antibodies are contemplated in addition to full-length immunoglobulins (e.g., IgE, IgG, IgM, IgA, etc.).

| Interferon | Attached Antibody | | | | | | | | |
|---|---|---|---|---|---|---|

TABLE 4-continued

Illustrative, but non-limiting antibody-interferon combinations contemplated for use in the constructs described herein. Where the antibody is listed, the native antibody, chimeric antibodies, humanized antibodies, single chain antibodies are contemplated in addition to full-length immunoglobulins (e.g., IgE, IgG, IgM, IgA, etc.).

| Interferon | Attached Antibody |
|---|---|
| replaced with other amino acid residue (s) while retaining an antiviral and/or cell-proliferation inhibitory activity. | |

The foregoing interferons and interferon/Ab constructs are intended to be illustrative and not limiting. Using the teaching provided herein, other suitable modified interferons (e.g., modified IFN-α, IFNβ, IFN-γ, etc.) and constructs can readily be identified and produced.

C. Attachment of the Targeting Moiety (e.g., Anti-CSPG4 Antibody) to the Interferon.

In various embodiments, the targeting moiety (e.g., an anti-CSPG4 antibody) and the interferon can be joined together in any order. Thus, for example, the antibody can be joined to either the amino or carboxy terminal of the interferon. The antibody can also be joined to an internal region of the interferon, or conversely, the interferon can be joined to an internal location or to any terminus of the antibody, as long as the attachment does not interfere with binding of the antibody to that target marker (e.g., CSPG4).

The antibody and the interferon (e.g., IFN-α, IFNβ, etc.) can be attached by any of a number of means well known to those of skill in the art. In certain embodiments, the interferon is conjugated, either directly or through a linker (spacer), to the antibody. In certain embodiments, however, it is preferable to recombinantly express the construct as a fusion protein (e.g., with a single chain antibody, or with one chain of a multi-chain antibody).

i) Chemical Conjugation of the Targeting Moiety to the Interferon.

In certain embodiments, the targeting moiety (e.g., an anti-CSPG4 antibody) is chemically conjugated to the interferon (e.g., IFN-α, IFNβ, mutIFNα, etc.) molecule. Means of chemically conjugating molecules are well known to those of skill.

The procedure for conjugating two molecules varies according to the chemical structure of the agent. Polypeptides typically contain variety of functional groups; e.g., carboxylic acid (COOH) or free amine (—NH$_2$) groups that are available for reaction with a suitable functional group on the other peptide, or on a linker to join the molecules thereto.

Alternatively, the antibody and/or the IFN-α can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the antibody to the interferon. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon.

A bifunctional linker having one functional group reactive with a group on the antibody and another group reactive on the interferon, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) Cancer Res. 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982); Waldmann (1991) Science, 252: 1657; U.S. Pat. Nos. 4,545,985 and 4,894,443, and the like.

ii) Production of Fusion Proteins.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins or encoding one chain of the antibody attached to an interferon can be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; the solid support method of U.S. Pat. No. 4,458,066, and the like.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 300 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins can be cloned using DNA amplification methods such as polymerase chain reaction (PCR). Thus, for example, the gene for IFN-α is PCR amplified, using a sense primer containing the restriction site for, e.g., NdeI and an antisense primer containing the restriction site for HindIII. This can produce a nucleic acid encoding the mature IFN-α sequence and having terminal restriction sites. An antibody having "complementary" restriction sites can similarly be cloned and then ligated to the IFN-α and/or to a linker attached to the IFN-α. Ligation of the nucleic acid sequences and insertion into a vector produces a vector encoding IFN-α joined to the anti-CSPG4 antibody.

While the two molecules can be directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

It was a surprising discovery, however, that certain linkers are unsuitable or less preferred for preparation of fusion proteins described herein. Thus, for example, the (Gly$_4$Ser)$_3$ (SEQ ID NO: 1) linker was not well suited for the production of certain antibody IFN-α constructs. Without being bound to a particular theory, it is believed the interferon was being removed from the fusion protein by proteolysis. Western blot analysis using anti-Fc and anti-interferon, confirmed that both of the upper bands were heavy chains, but only the largest contained interferon.

Accordingly, in certain preferred embodiments, it is desirable to use a linker that is resistant to proteolysis. Certain preferred linkers are linkers that are not or that do not comprise the (Gly$_4$Ser)$_3$ (SEQ ID NO:30) linker. Certain preferred linkers are linkers shorter than 15 amino acids, or linkers shorter than 14, 13, 12, 11, 10, 9, 8, 7, 6, 5, 4, 3, or 2 amino acids in length. In certain embodiments the linker is an alpha helical linker ranging in length up to about 12 or 13 or 14 amino acids in length.

Certain illustrative proteolysis-resistant linkers well suited for use in the constructs of this invention are shown in Table 5.

TABLE 5

Illustrative proteolysis-resistant linkers.

| Linker Seq | SEQ ID NO |
|---|---|
| GGG | |
| GGS | |
| GGGGS | 31 |
| SGGGGS | 32 |
| GGGGSGGGGS | 33 |

TABLE 5 -continued

Illustrative proteolysis-resistant linkers.

| Linker Seq | SEQ ID NO |
|---|---|
| A EAAAK A | 34 |
| A EAAAK EAAAK A | 35 |
| A EAAAK EAAAK EAAAK A | 36 |
| A EAAAK EAAAK EAAAK EAAAK A | 37 |
| A EAAAK EAAAK EAAAK EAAAK EAAAK A | 38 |
| AEAAAKEAAAKAG | 39 |
| AEAAAKEAAAKAGS | 40 |
| GGGGG | 41 |
| GGAGG | 42 |
| GGGGGGGG | 43 |
| GAGAGAGAGA | 44 |
| RPLSYRPPFPFGFPSVRP | 45 |
| YPRSIYIRRRHPSPSLTT | 46 |
| TPSHLSHILPSFGLPTFN | 47 |
| RPVSPFTFPRLSNSWLPA | 48 |
| SPAAHFPRSIPRPGPIRT | 49 |
| APGPSAPSHRSLPSRAFG | 50 |
| PRNSIHFLHPLLVAPLGA | 51 |
| MPSLSGVLQVRYLSPPDL | 52 |
| SPQYPSPLTLTLPPHPSL | 53 |
| NPSLNPPSYLHRAPSRIS | 54 |
| LPWRTSLLPSLPLRRRP | 55 |
| PPLFAKGPVGLLSRSFPP | 56 |
| VPPAPVVSLRSAHARPPY | 57 |
| LRPTPPRVRSYTCCPTP | 58 |
| PNVAHVLPLLTVPWDNLR | 59 |
| CNPLLPLCARSPAVRTFP | 60 |
| LGTPTPTPTPTGEF | 61 |
| EDFTRGKL | 62 |
| L EAAAR EAAAR EAAAR EAAAR | 63 |
| L EAAAR EAAAR EAAAR | 64 |
| L EAAAR EAAAR | 65 |
| L EAAAR | 66 |
| EAAAR EAAAR EAAAR EAAAR | 67 |
| EAAAR EAAAR EAAAR | 68 |
| EAAAR EAAAR | 69 |
| EAAAR | 70 |
| LTEEQQEGGG | 71 |

TABLE 5 -continued

Illustrative proteolysis-resistant linkers.

| Linker Seq | SEQ ID NO |
|---|---|
| TEEQQEGGG | 72 |
| LAKLKQKTEQLQDRIAGGG | 73 |
| LELKTPLGDTTHTCPRCPEPKSCDTPPPCPRCP EPKSCDTPPPCPRCPEPKSCDTPPPCPRCPGG | 74 |
| LEPKSSDKTHTSPPSPGG | 75 |

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.: Deutscher (1990) *Methods in Enzymology Vol. 182: Guide to Protein Purification*, Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein (e.g., anti-CSPG4-IFN-α, anti-CSPG4-mutIFN-α, etc.) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

In certain embodiments a transient expression system can be used to express the chimeric constructs described herein. Although many cell lines potentially can be used, one cell line that works well for transient expression is 293T. For transient expression of 293T on Day 0, 9 million cells in 25 ml are seeded for each 150 mm tissue culture plate. A 1 mg/ml of PEI (Polyethylenimine) is made using sterile water. For the expression of a complete antibody or antibody fusion protein, 25 μg each of H and L (50 ug total) is used per plate. A volume of 5 ml is used for transfection of each 150 mm plate. The DNA is mixed with DMEM, the PEI is then added and the mixture is incubated at room temperature for 10 mins. 1.75 μg PEI is used for each ug of DNA. For transfection, the old medium is removed, discarded and replaced with 20 ml of fresh medium (Iscoves+5% calf serum). The transfection mix is added and the plate is swirled. On Day 2, the medium is replaced with 30 ml of Iscoves medium containing 1% FBS (fetal bovine serum) to minimize the amount of bovine Ig present. Supernatants are collected from the cells on Days 4, 6 and 13 by removing the medium and replacing it with 30 ml of fresh Iscover containing 1% FBS.

One of skill would recognize these expression methods are illustrative and not limiting. Modifications can be made to the fusion proteins described herein without diminishing their activity/efficacy. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Other modifications can be made to increase serum half-life and/or bioavailability. Such modifications include, but are not limited to the incorporation of D amino acids (especially in the linker), the use of non-naturally occurring amino acids, pegylation of the fusion protein, and the like.

D. Other Multi-Valent Targeting Moieties.

In certain embodiments this invention contemplates the use of multivalent, preferably trivalent, quadravalent, pentavalent or greater targeting moieties to target the interferon to a target cell.

For example, multivalent anti-CSPG4 moieties can be produced by any of a number of methods. For example, linkers having three, four, or more reactive sites can be reacted with anti-CSPG4 antibodies to form a trimer or greater conjugate.

In certain embodiments, phage display, yeast display, bacterial display, or other display systems can be used to express and display multiple copies (e.g., at least 3, at least 4, at least 5, at least 6 copies, etc.) of a targeting antibody (e.g., anti-CSPG4 such as B-B4) and thereby effectively provide a multivalent targeting moiety.

In certain embodiments the use of diabodies and triabodies (e.g., comprising two domains that bind CSPG4 or one domain that binds CSPG4 and another domain that binds, for example, a member of the EGFR receptor family (e.g., EGFR, HER3, etc.). Typically, diabodies comprise a heavy (VH) chain variable domain connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites (see, e.g., Holliger et al. (1993) *Proc. Natl. Acad. Sci.*, 90: 6444-6448). In certain embodiments to construct bispecific diabodies the V-domains of antibody A and antibody B are fused to create the two chains VHA-VLB, VHB-VLA. Each chain is inactive in binding to antigen, but recreates the functional antigen binding sites of antibodies A and B on pairing with the other chain.

II. Combined Uses.

The constructs described herein are useful for inhibiting the growth and/or proliferation of target cells (e.g., cancer cells). In various embodiments the constructs can be used to inhibit disease progression, to reduce the rate of secondary tumor formation, to shrink tumor size, and/or to stabilize regression/remission.

Particularly in the treatment of cancer, the constructs, formulations, and methods described herein may also include additional therapeutic and/or pharmacologically acceptable agents. For instance, the constructs, formulations, or methods may involve other agents for the treatment of cancer. Such agents include, but are not limited to alkylating agents (e.g., mechlorethamine (MUSTARGEN®), cyclophosphamide (CYTOXAN®, NEOSAR®)), ifosfamide (IFEX®), phenylalanine mustard; melphalen (ALKERAN®), chlorambucol (LEUKERAN®), uracil mustard, estramustine (EMCYT®), thiotepa (THIOPLEX®), busulfan (MYERLAN®), lomustine (CEENU®), carmustine (BICNU®, BCNU®), streptozocin (ZANOSAR®), dacarbazine (DTIC-Dome), cis-platinum, cisplatin (PLATINOL®, PLATINOL AQ®), carboplatin (PARAPLATIN®), altretamine (HEXALEN®, etc.), antimetabolites (e.g. methotrexate (AMETHOPTERIN®, FOLEX®, MEXATE®, RHEUMATREX®), 5-fluoruracil (ADRUCIL®, EFUDEX®, FLUOROPLEX®), floxuridine, 5-fluorodeoxyuridine (FUDR), capecitabine (XELODA®), fludarabine: (FLUDARA®), cytosine arabinoside (CYTARIBINE®, CYTOSAR®, ARA-C®), 6-mercaptopurine (PURINETHOL®), 6-thioguanine (Thioguanine), gemcitabine (GEMZAR®), cladribine (LEUSTATIN®), deoxycoformycin; pentostatin (NIPENT®), etc.), antibiotics (e.g. doxorubicin (ADRIAMYCIN®, RUBEX®, DOXIL®, DAUNOXOME® liposomal preparation), daunorubicin (DAUNOMYCIN®, CERUBIDINE®), idarubicin (IDAMYCIN®), valrubicin (VALSTAR®), mitoxantrone (NOVANTRONE®), dactinomycin (ACTINOMYCIN D®, COSMEGEN®), mithramycin, plicamycin (MITHRACIN®), mitomycin C (MUTAMYCIN®), bleomycin (BLENOXANE®), procarbazine (MATULANE®, etc.), mitotic inhibitors (e.g. paclitaxel (TAXOL®)), docetaxel (TAXOTERE®), vinblatine sulfate (VELBAN®, VELSAR®, VLB®), vincristine sulfate (ONCOVIN®, VINCASAR PFS®, VINCREX®), vinorelbine sulfate (NAVELBINE®, etc.), chromatin function inhibitors (e.g., topotecan (CAMPTOSAR®), irinotecan (HYCAMTIN®), etoposide (VP-16®, VEPESID®, TOPOSAR®), teniposide (VM-26®, VUMON®, etc.), hormones and hormone inhibitors (e.g. diethylstilbesterol (STILBESTEROL®, STILPHOSTROL®), estradiol, estrogen, esterified estrogens (ESTRATAB®, MENEST®), estramustine (EMCYT®), tamoxifen (NOVALDEX®)), toremifene (FARESTON®) anastrozole (ARIMIDEX®), letrozole (FEMARA®), 17-OH-progesterone, medroxyprogesterone, megestrol acetate (MEGACE®), goserelin (ZOLADEX®), leuprolide (LEUPRON®), testosteraone, methyltestosterone, fluoxmesterone (ANDROID-F®, HALOTESTIN®), flutamide (EULEXIN®), bicalutamide (CASODEX®), nilutamide (NILANDRON®, etc.), inhibitors of synthesis (e.g., aminoglutethimide (CYTADREN®), ketoconazole (NIZORAL®, etc.)), immunomodulators (e.g., RITUXIMAB® (Rituxan), trastuzumab (HERCEPTIN®), denileukin diftitox (ONTAK®), levamisole (ERGAMISOL®), *bacillus* Calmette-Guerin, BCG (THERACYS®, TICE BCG), interferon alpha-2a, alpha 2b (ROFERON-A®, INTRON A®), interleukin-2, aldesleukin (PROLEUKIN®), etc.) and other agents such as 1-aspariginase (ELSPAR®, KIDROLASE®), pegaspasgase (ONCASPAR®), hydroxyurea (HYDREA®, DOXIA®), leucovorin (WELLCOVORIN®), mitotane (LYSODREN®), porfimer (PHOTOFRIN®), tretinoin (VEASNOID®), and the like.

III. Pharmaceutical Compositions.

In certain embodiments, in order to carry out the methods described herein, one or more active agents (e.g. interferon/antibody constructs described herein) are administered, e.g. to an individual diagnosed as having (or at risk for) a cancer. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents (e.g., constructs) described herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

In various embodiments the active agents (e.g., constructs) described herein are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the constructs described herein or formulations comprising such constructs are administered to a subject, e.g., to patient suffering e.g. from a cancer, or at risk of cancer (e.g. after surgical removal of a primary tumor) in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain embodiments, the active agents (e.g., constructs described herein) are administered orally (e.g. via a tablet) or as an injectable in accordance with standard methods well known to those of skill in the art. In other preferred embodiments, the constructs may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments elevated serum half-life can be maintained by the use of sustained-release protein "packaging" systems. Such sustained release systems are well known to those of skill in the art. In one preferred embodiment, the PROLEASE® biodegradable microsphere delivery system for proteins and peptides (see, e.g., Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the active agent in a polymer matrix that can be compounded as a dry formulation with or without other agents.

The PROLEASE® microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

IV. Kits.

In certain embodiments, kits for the treatment of a primary cancer and/or in an adjunct therapy are provided. In various embodiments the kits typically comprise a container containing a construct described herein (e.g., anti-CSPG4-IFNα, anti-CSPG4-mutIFNα, anti-CSPG4-IFN, etc.). In various embodiments the construct can be present in a pharmacologically acceptable excipient.

In addition the kits can optionally include instructional materials disclosing means of use of the chimeric moiety (e.g. to treat a cancer and/or as an adjunct therapeutic). The instructional materials may also, optionally, teach preferred dosages, counter-indications, and the like.

The kits can also include additional components to facilitate the particular application for which the kit is designed. Thus, for example, in certain embodiments, the kit can additionally contain one or more additional anti-cancer drugs (e.g., doxirubicin, vinblastine, etc.), and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Anti-CSPG4 Fusions with Type I Interferon for the Treatment of Malignancy

The type 1 interferons (IFNα and IFNβ) are potent regulators of cell growth, with inhibitory effects against many human cancers (Pestka et al. (2004) *Immunol. Rev.* 202: 8-32; Borden et al. (2005) *J. Interferon Cytokine Res.* 25: 511-527; Borden et al. (2007) *Nat. Rev. Drug Discov.* 6: 975-690; Brassard et al. (2002) *J. Leukoc. Biol.* 71: 565-581; Bekisz et al. (2010) *Pharmaceuticals* (Basel) 3: 994-1015). Until now however, the clinical use of these agents has been limited by the inability to achieve effective concentrations of IFN at sites of tumor without causing systemic toxicity. A goal of this study is to overcome this limitation by using the tumor-targeting ability of monoclonal antibodies to carry interferons (IFNs) directly to cancer sites to mediate not only tumor destruction but also possibly to recruit the immune system to recognize and destroy residual cancer cells. It was hypothesized that antibody-IFN fusion proteins could be highly effective cancer therapeutic agents, selectively localizing IFN to sites of tumor.

Type I Interferons as Anti-Cancer Agents

Type I interferons consist of seven classes with IFNα and IFNβ being the most abundant (Pestka et al. (2004) *Immunol. Rev.* 202: 8-32). Type I IFNs are pleiotropic cytokines with a broad spectrum of anti-cancer activities attractive for treating melanoma and other cancers (Borden et al. (2005) *J. Interferon Cytokine Res.* 25: 511-527; Borden et al. (2007) *Nat. Rev. Drug Discov.* 6: 975-690; Brassard et al. (2002) *J. Leukoc. Biol.* 71: 565-581; Bekisz et al. (2010) *Pharmaceuticals* (Basel) 3: 994-1015). Beneficial properties of IFNα/β against cancers include, but are not limited to, direct anti-proliferative and pro-apoptotic effects (Grimley et al. (1998) *Blood*, 91: 3017-3027; Yanase et al. (2000) *J. Interferon Cytokine Res.* 20: 1121-1129; Chawla-Sarkar et al. (2003) *Apoptosis* 8: 237-249), blockade of autocrine growth factor loops (Heslop et al. (1990) *J. Exp. Med.* 172: 1729-1734), repression of c-myc oncogene expression (Einat et al. (1985) *Nature*, 313: 597-600), down-regulation of telomerase activity (Xu et al. (2000) *Blood*, 96: 4313-4318), and inhibition of angiogenesis (Borden et al. (2005) *J. Interferon Cytokine Res.* 25: 511-527). Favorable immunologic effects of IFNα/β for cancer treatment include activation of T cell, NK cell, and dendritic cell functions, as well as upregulation of class I MHC molecules on the tumor cell surface (Sikora et al. (2009) *J. Immunol.* 182(12): 7398-7407; Paquette et al. (1998) *J. Leukoc. Biol.* 64: 358-367; Papewalis et al. (2008) *J. Immunol.*, 180: 1462-1470). All type I IFNs are recognized by a single shared receptor composed of two transmembrane proteins, IFNAR1 and IFNAR2. Features of IFNβ compared to IFNα include stronger receptor binding (Lamken et al. (2004) *J. Mol. Biol.* 341: 303-318) and more potent anti-proliferative activities (Jaitin et al. (2006) *Mol. Cell Biol.* 26: 1888-1897).

Recombinant IFNα (rIFNα) has clinical activity against follicular non-Hodgkin lymphoma, melanoma, multiple myeloma, chronic lymphocytic leukemia, hairy cell leukemia, chronic myelogenous leukemia, AIDS-related Kaposi sarcoma, and renal cell carcinoma (Borden et al. (2007) *Nat. Rev. Drug Discov.* 6: 975-690; Bekisz et al. (2010) *Pharmaceuticals* (Basel) 3: 994-1015; Jonasch and Haluska (2001) *Oncologist* 6: 34-55). However, in most of these cases the clinical effects are modest since systemic administration is dose-limited by side effects including flu-like symptoms, fatigue, nausea/anorexia, neutropenia, neuropsychiatric symptoms, and injection site reactions (Jonasch and Haluska (2001) *Oncologist* 6: 34-55). Also contributing to the limited clinical utility of IFNα is its short serum half-life (5 hours), and the lack of effective levels of the cytokine within tumor sites. Pharmacokinetic studies have indicated that only 0.01% of subcutaneously injected IFNα reaches the target tumor site (Suzuki et al. (2003) *Gene Ther*, 10: 765-773). Given these limitations, it has been difficult to achieve effective concentrations of IFNα at sites of malignant disease without causing systemic toxicity.

IFNα for Treatment of Malignant Melanoma

Recombinant interferon alpha (rIFNα) is an FDA-approved treatment for high-risk resected melanoma, a setting in which studies have shown improved survival, and is also used to treat metastatic disease (Garbe et al. (2011) *Oncologist,* 16(1): 5-24; Pasquali and Mocellin (2010) *Curr. Med. Chem.* 17(29): 3327-3336). However, while melanoma cells are very sensitive to growth inhibition to high concentrations of rIFNα in vitro (Bekisz et al. (2010) *Pharmaceuticals* (Basel) 3: 994-1015), these levels are not attainable by dosing with the free, soluble cytokine. Antibody-targeted delivery of IFNα/β to sites of melanoma was tested to determine if such an approach could be efficacious, and potentially associated with much less systemic toxicity.

Chondroitin Sulfate Proteoglycan 4 (CSPG4, Also Known as High Molecular Weight-Melanoma-Associated Antigen, HMW-MAA) as a Cell Surface Target on Malignant Melanoma Cells Because of its expression in over 80% of human melanomas and its restricted distribution in normal tissues, CSPG4 has been studied as a target for the immunotherapy of melanoma (Campoli et al. (2004) *Crit. Rev. Immunol.* 24(4): 267-296; Campoli et al. (2010) *Adv. Cancer Res.* 109: 73-121). While a monoclonal antibody targeting CSPG4 can slow the growth of human melanoma cells engrafted into immunodeficient mice (Hafner et al. (2005) *Int. J. Cancer,* 114: 4261-4432), such antibodies have not been found to be effective in vivo against melanoma in humans (Campoli et al. (2004) *Crit. Rev. Immunol.* 24(4): 267-296; Campoli et al. (2010) *Adv. Cancer Res.* 109: 73-121).

Results

Figure 5:
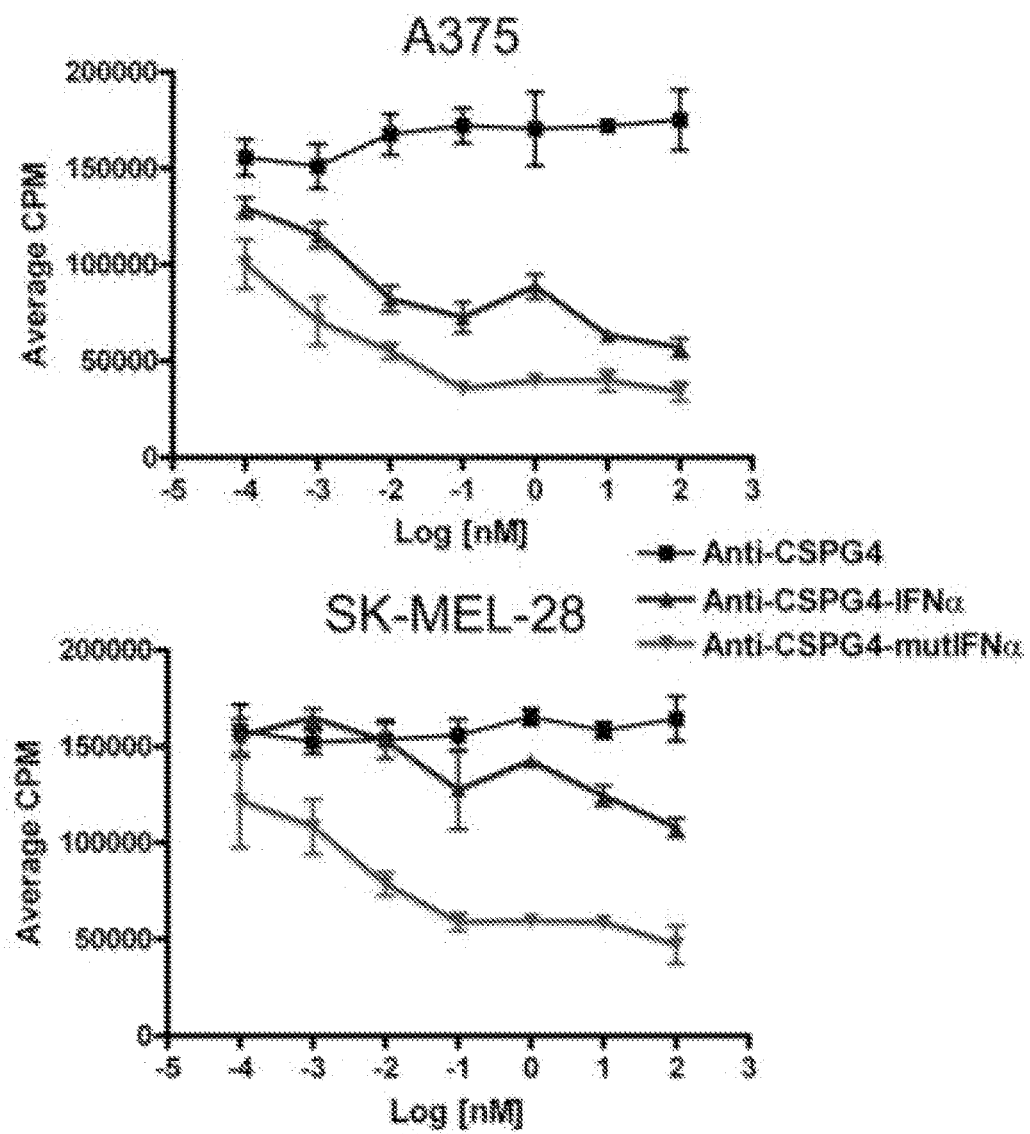
FIG. 5 shows the sensitivity of human melanoma cell lines to anti-CSPG4-IFNα fusion proteins. Tumor cells were seeded in quadruplicate at $5\times10^3$ cells/well in graded concentrations of unfused parent antibody or fusion protein (starting at 100 nM and serially diluted 10-fold), then incubated for 72 hours. Cells were pulsed with $^3$[H]-thymidine and harvested 8 hours later. Incorporated radioactivity (counts per minute) was measured and results reported as arithmetic means±SD.

Recombinant Antibody-IFNα Fusion Proteins Targeting the CSPG4 are Efficacious Against Human Melanoma Cells In Vitro and In Vivo Recombinant forms of the monoclonal antibody 9.2.27 that recognizes CSPG4 (Morgan et al. (1981) *Hybridoma,* 1(1): 27-36) were engineered into the backbone of human IgG1 (FIG. 2). These included a native form of the antibody, a fusion containing human IFNα, and a fusion containing a mutant IFNα2 (mutIFNα) that mimics IFNβ in terms of higher affinity binding to IFNAR1 (Eyal et al. (2007) *J. Biol. Chem.* 282(15): 11602-11611). The recombinant anti-CSPG4 antibody recognized 2 different human melanoma cell lines (SK-MEL-28 and A375) in a specific manner, showing high-level binding (FIG. 3). Both of these cell lines were sensitive to growth inhibition by free, recombinant human IFNα and IFNβ, with IFNβ being more effective, as expected (FIG. 4). The ability of the engineered IFNα fusion proteins to inhibit the in vitro growth of these cell lines was tested. As shown in FIG. 5, the native IgG1 anti-CSPG4 antibody had no effect on the growth of either cell line. The anti-CSPG4-hIFNα fusion was effective at modestly inhibiting the growth of SK-MEL-28 cells, and inhibiting A375 proliferation by 50-60%. By contrast, the anti-CSPG4-mutIFNα fusion potently inhibited the growth of both cell lines, achieving approximately 70% inhibition of SK-MEL-28 and 80% inhibition of A375. Anti-CSPG4-IFNα and anti-CSPG4-mutIFNα also inhibited the proliferation of melanoma cells with different BRAF and NRAS mutations (FIG. 6) with anti-CSPG4-mutIFNα more effective than anti-CSPG4-IFNα.

To test the ability of the fusion proteins to inhibit tumor growth in vivo, A375 cells were grown as subcutaneous xenografts in immunodeficient SCID mice (FIG. 7). After 5 days of tumor growth, mice were treated with a short course (days 5, 12, and 19) of intravenous phosphate buffered saline control, native anti-CSPG4 IgG1, anti-CSPG4-IFNα, or anti-CSPG4-mutIFNα. In mice treated with saline, tumors grew progressively, and all tumors had reached 1.4 cm in diameter before day 40. Treatment with native antibody or anti-CSPG4-IFNα appeared to slightly delay tumor growth (all tumors reaching 1.4 cm in diameter by day 44) although these differences were not statistically significant compared to saline control ($p=0.073$ and $p=0.079$, respectively). However, treatment with anti-CSPG4mutIFNα significantly delayed the growth of tumors compared to saline control ($p=0.003$), native antibody ($p=0.0048$), and anti-CSPG4-IFNα ($p=0.0048$). Notably, tumors did not appear to progress in mice treated with anti-CSPG4-mutIFNα until after day 19, when therapy was stopped, suggesting ongoing suppression of tumor growth in vivo. Thus, even a brief course of low-dose anti-CSPG4-mutIFNα fusion protein therapy was able to significantly delay the growth a human melanoma in vivo.

Example 2

Anti-CSPG4-Fusions with IFN Gamma (IFNγ)

A number of anti-CSPG4-Interferon gamma constructs comprising the 9.2.27 antibody were recombinantly expressed using different linkers (see Table 6). IFNγ functions as an anti-parallel dimer. Accordingly two different types of constructs were utilized. In one construct, each CH3 domain comprising the antibody had an IFNγ attached to the carboxyl terminus. In another embodiment, two interferons were attached to the CH3 domain of each antibody joined by a landar linker.

The fusion proteins with different linkers all used the anti-CSPG4 (9.2.27) described in Example 1. Their activity was analyzed against different cell lines as described below.

TABLE 6

Linkers utilized in anti-CSPG4-IFNγ constructs.

| Linker Name | Amino Acid Sequence | Nucleotide Sequence |
|---|---|---|
| Landar | LTEEQQEGGG (SEQ ID NO: 71) | CTTACCGAGGAGCAGCAGGAGGGC GGCGGC (SEQ ID NO: 76) |
| Double Landar* | LTEEQQEGGG- hIFNγ-TEEQQEGGG (SEQ ID NO: 77) | CTTACCGAGGAGCAGCAGGAGGGC GGCGGC-hIFNgamma nt sequence-ACCGAGGAGCAGCAG GAGGGCGGCGGC (SEQ ID NO: 78) |
| 1qo0E_1 | LAKLKQKTEQLQDRI AGGG (SEQ ID NO: 73) | CTTGCTAAATTAAAACAAAAACT GAACAATTACAAGATCGTATTGCT GGTGGCGGC (SEQ ID NO: 79) |

TABLE 6-continued

Linkers utilized in anti-CSPG4-IFNγ constructs.

| Linker Name | Amino Acid Sequence | Nucleotide Sequence |
|---|---|---|
| IgG3 hinge | LELKTPLGDTTHTCP RCPEPKSCDTPPPCPR CPEPKSCDTPPPCPRC PEPKSCDTPPPCPRCP (SEQ ID NO: 74) | CTTGAGCTCAAAACCCCACTTGGT GACACAACTCACACATGCCCACGG TGCCCAGAGCCCAAATCTTGTGAC CCTCCCCCGTGCCCAAGGTGC CCAGAGCCCAAATCTTGTGACACA CCTCCCCCGTGCCCAAGGTGCCA GAGCCCAAATCTTGTGACACACCT CCCCCGTGCCCAAGGTGCCCAGGC GGC (SEQ ID NO: 80) |
| IgG1 hinge cys | LEPKSSDKTHTSPPSP GG (SEQ ID NO: 75) | CTTGAGCCCAAATCTTCCGACAAA ACTCACACATCTCCACCGTCCCCA GGCGGC (SEQ ID NO: 81) |

*Double landar = landar linker joining INF to antibody and second landar joining second IFN to first IFN.
Leading "L" on linker is optional, can be introduced to permit construction of restriction site in nucleotide construct.

The amino acid sequence of components of these various constructs are shown in Table 7.

TABLE 7

Amino acid and nucleic acid sequences of linker-Interferon gamma components that are attached to the anti-CSPG4 antibody.

| | |
|---|---|
| Amino acid sequence of Landar hIFNγ: | LTEEQQEGGGQDPYVKEAENLKKYFNAGHSDVADNGTLFLGI LKNWKEESDRKIMQSQIVSFYFKLFKNFKDDQSIQKSVETIKE DMNVKFFNSNKKKRDDFEKLTNYSVTDLNVQRKAIHELIQV MAELSPAAKTGKRKRSQM (SEQ ID NO: 82) |
| Nucleotide sequence of Landar hIFNγ: | CTTACCGAGGAGCAGCAGGAGGGCGGCGGCCAGGATCCCT ACGTGAAGGAGGCCGAGAACCTGAAGAAGTACTTCAACGC CGGCCACTCCGACGTGGCCGACAACGGCACCCTGTTCCTGG GCATCCTGAAGAACTGGAAGGAGGAGTCCGACAGGAAGAT CATGCAGTCCCAGATCGTGTCCTTCTACTTCAAGCTGTTCA AGAACTTCAAGGACGACCAGTCCATCCAGAAGTCCGTGGA GACCATCAAGGAGGACATGAACGTGAAGTTCTTCAACTCC AACAAGAAGAAGAGGGACGACTTCGAGAAGCTGACCAACT ACTCCGTGACCGACCTGAACGTGCAGAGGAAGGCCATCCA CGAGCTGATCCAGGTGATGGCCGAGCTGTCCCCCGCCGCCA AGACCGGCAAGAGGAAGAGGTCCCAGATG (SEQ ID NO: 83) |
| Amino acid sequence of Double Landar hIFNγ: | LTEEQQEGGGQDPYVKEAENLKKYFNAGHSDVADNGTLFLGI LKNWKEESDRKIMQSQIVSFYFKLFKNFKDDQSIQKSVETIKE DMNVKFFNSNKKKRDDFEKLTNYSVTDLNVQRKAIHELIQV MAELSPAAKTGKRKRSQMTEEQQEGGGQDPYVKEAENLKKY FNAGHSDVADNGTLFLGILKNWKEESDRKIMQSQIVSFYFKLF KNFKDDQSIQKSVETIKEDMNVKFFNSNKKKRDDFEKLTNYS VTDLNVQRKAIHELIQVMAELSPAAKTGKRKRSQM (SEQ ID NO: 84) |
| Nucleotide sequence of Double Landar hIFNγ: | CTTACCGAGGAGCAGCAGGAGGGCGGCGGCCAGGACCCCT ACGTGAAGGAGGCCGAGAACCTGAAGAAGTACTTCAACGC CGGCCACTCCGACGTGGCCGACAACGGCACCCTGTTCCTGG GCATCCTGAAGAACTGGAAGGAGGAGTCCGACAGGAAGAT CATGCAGTCCCAGATCGTGTCCTTCTACTTCAAGCTGTTCA AGAACTTCAAGGACGACCAGTCCATCCAGAAGTCCGTGGA GACCATCAAGGAGGACATGAACGTGAAGTTCTTCAACTCC AACAAGAAGAAGAGGGACGACTTCGAGAAGCTGACCAACT ACTCCGTGACCGACCTGAACGTGCAGAGGAAGGCCATCCA CGAGCTGATCCAGGTGATGGCCGAGCTGTCCCCCGCCGCCA AGACCGGCAAGAGGAAGAGGTCCCAGATGACCGAGGAGC AGCAGGAGGGCGGCGGCCAGGATCCCTACGTGAAGGAGGC CGAGAACCTGAAGAAGTACTTCAACGCCGGCCACTCCGAC GTGGCCGACAACGGCACCCTGTTCCTGGGCATCCTGAAGA ACTGGAAGGAGGAGTCCGACAGGAAGATCATGCAGTCCCA GATCGTGTCCTTCTACTTCAAGCTGTTCAAGAACTTCAAGG ACGACCAGTCCATCCAGAAGTCCGTGGAGACCATCAAGGA GGACATGAACGTGAAGTTCTTCAACTCCAACAAGAAGAAG AGGGACGACTTCGAGAAGCTGACCAACTACTCCGTGACCG ACCTGAACGTGCAGAGGAAGGCCATCCACGAGCTGATCCA GGTGATGGCCGAGCTGTCCCCCGCCGCCAAGACCGGCAAG AGGAAGAGGTCCCAGATG (SEQ ID NO: 85) |
| Amino acid sequence of 1qo0E_1-hIFNγ: | LAKLKQKTEQLQDRIAGGGQDPYVKEAENLKKYFNAGHSDV ADNGTLFLGILKNWKEESDRKIMQSQIVSFYFKLFKNFKDDQS IQKSVETIKEDMNVKFFNSNKKKRDDFEKLTNYSVTDLNVQR KAIHELIQVMAELSPAAKTGKRKRSQM (SEQ ID NO: 86) |

TABLE 7 -continued

Amino acid and nucleic acid sequences of linker-Interferon gamma components that are attached to the anti-CSPG4 antibody.

| | |
|---|---|
| Nucleotide sequence of 1qo0E_1-hIFNγ: | CTTGCTAAATTAAAACAAAAAACTGAACAATTACAAGATC<br>GTATTGCTGGTGGCGGCCAGGATCCCTACGTGAAGGAGGC<br>CGAGAACCTGAAGAAGTACTTCAACGCCGGCCACTCCGAC<br>GTGGCCGACAACGGCACCCTGTTCCTGGGCATCCTGAAGA<br>ACTGGAAGGAGGAGTCCGACAGGAAGATCATGCAGTCCCA<br>GATCGTGTCCTTCTACTTCAAGCTGTTCAAGAACTTCAAGG<br>ACGACCAGTCCATCCAGAAGTCCGTGGAGACCATCAAGGA<br>GGACATGAACGTGAAGTTCTTCAACTCCAACAAGAAGAAG<br>AGGGACGACTTCGAGAAGCTGACCAACTACTCCGTGACCG<br>ACCTGAACGTGCAGAGGAAGGCCATCCACGAGCTGATCCA<br>GGTGATGGCCGAGCTGTCCCCCGCCGCCAAGACCGGCAAG<br>AGGAAGAGGTCCCAGATG (SEQ ID NO: 87) |
| Amino acid sequence of IgG3 hinge-hIFNγ: | LELKTPLGDTTHTCPRCPEPKSCDTPPPCPRCPEPKSCDTPPPCP<br>RCPEPKSCDTPPPCPRCPGGQDPYVKEAENLKKYFNAGHSDV<br>ADNGTLFLGILKNWKEESDRKIMQSQIVSFYFKLFKNFKDDQS<br>IQKSVETIKEDMNVKFFNSNKKKRDDFEKLTNYSVTDLNVQR<br>KAIHELIQVMAELSPAAKTGKRKRSQM (SEQ ID NO: 88) |
| Nucleotide sequence of IgG3 hinge-hIFNγ: | CTTGAGCTCAAAACCCCACTTGGTGACACAACTCACACATG<br>CCCACGGTGCCCAGAGCCCAAATCTTGTGACACACCTCCCC<br>CGTGCCCAAGGTGCCCAGAGCCCAAATCTTGTGACACACCT<br>CCCCCGTGCCCAAGGTGCCCAGAGCCCAAATCTTGTGACAC<br>ACCTCCCCCGTGCCCAAGGTGCCCAGGCGGCCAGGATCCCT<br>ACGTGAAGGAGGCCGAGAACCTGAAGAAGTACTTCAACGC<br>CGGCCACTCCGACGTGGCCGACAACGGCACCCTGTTCCTGG<br>GCATCCTGAAGAACTGGAAGGAGGAGTCCGACAGGAAGAT<br>CATGCAGTCCCAGATCGTGTCCTTCTACTTCAAGCTGTTCA<br>AGAACTTCAAGGACGACCAGTCCATCCAGAAGTCCGTGGA<br>GACCATCAAGGAGGACATGAACGTGAAGTTCTTCAACTCC<br>AACAAGAAGAAGAGGGACGACTTCGAGAAGCTGACCAACT<br>ACTCCGTGACCGACCTGAACGTGCAGAGGAAGGCCATCCA<br>CGAGCTGATCCAGGTGATGGCCGAGCTGTCCCCCGCCGCCA<br>AGACCGGCAAGAGGAAGAGGTCCCAGATG (SEQ ID NO: 89) |
| Amino acid sequence of IgG1 hinge δ cys-hIFNγ: | LEPKSSDKTHTSPPSPGGQDPYVKEAENLKKYFNAGHSDVAD<br>NGTLFLGILKNWKEESDRKIMQSQIVSFYFKLFKNFKDDQSIQ<br>KSVETIKEDMNVKFFNSNKKKRDDFEKLTNYSVTDLNVQRK<br>AIHELIQVMAELSPAAKTGKRKRSQM (SEQ ID NO: 90) |
| Nucleotide sequence of IgG1 hinge δ cys-hIFNγ: | CTTGAGCCCAAATCTTCCGACAAAACTCACACATCTCCACC<br>GTCCCCAGGCGGCCAGGATCCCTACGTGAAGGAGGCCGAG<br>AACCTGAAGAAGTACTTCAACGCCGGCCACTCCGACGTGG<br>CCGACAACGGCACCCTGTTCCTGGGCATCCTGAAGAACTGG<br>AAGGAGGAGTCCGACAGGAAGATCATGCAGTCCCAGATCG<br>TGTCCTTCTACTTCAAGCTGTTCAAGAACTTCAAGGACGAC<br>CAGTCCATCCAGAAGTCCGTGGAGACCATCAAGGAGGACA<br>TGAACGTGAAGTTCTTCAACTCCAACAAGAAGAAGAGGGA<br>CGACTTCGAGAAGCTGACCAACTACTCCGTGACCGACCTGA<br>ACGTGCAGAGGAAGGCCATCCACGAGCTGATCCAGGTGAT<br>GGCCGAGCTGTCCCCCGCCGCCAAGACCGGCAAGAGGAAG<br>AGGTCCCAGATG (SEQ ID NO: 91) |

Figure 8:
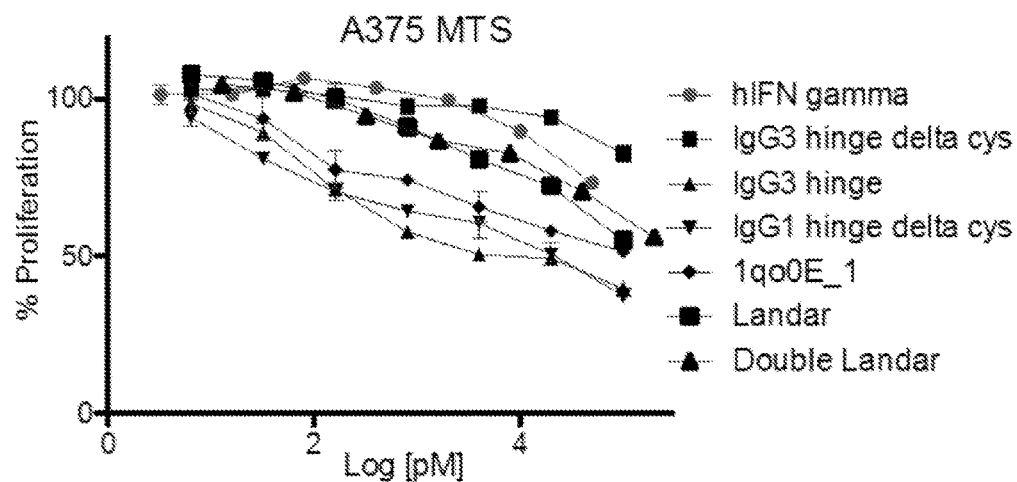
FIG. 8 shows that anti-CSPG4-fusions with IFNγ have differing activities in MTS assays depending on the linker used for the fusion protein on A375 myeloma cells in an MTS assay. Data are expressed as the percent metabolic activity in the treated cells compared with untreated cells. Data are shown as the mean of triplicate samples±SD.

A375 myeloma cells were incubated with differing concentrations of the indicated fusion protein or with recombinant IFNγ for 4 days. The metabolic activity of the remaining cells was then measured using the MTS assay. As illustrated in FIG. 8, anti-CSPG4-fusions with IFNγ show differing activities depending on the linker used for the fusion protein.

Figure 9:
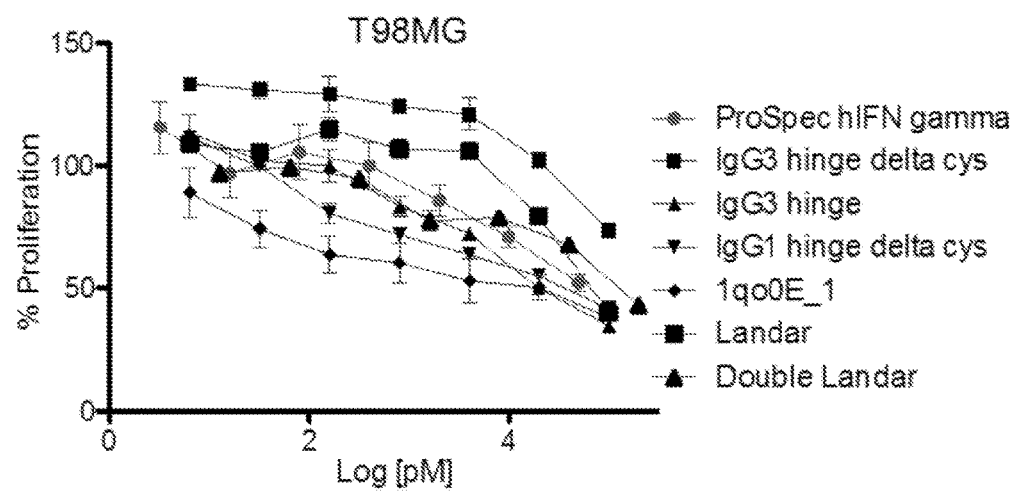
FIG. 9 shows that shows that anti-CSPG4-fusions with IFNγ show differing activities against the T98 glioblastoma in MTS assays depending on the linker used for the fusion protein. Data are expressed as the percent metabolic activity in the treated cells compared with untreated cells. Data are shown as the mean of triplicate samples±SD.

T98 cells were incubated with differing concentrations of the indicated fusion protein or with recombinant IFNγ for 72 hours. The metabolic activity of the remaining cells was then measured using the MTS assay. As illustrated in FIG. 9, anti-CSPG4-fusions with IFNγ show differing activities against the T98 glioblastoma depending on the linker used for the fusion protein.

Figure 10:
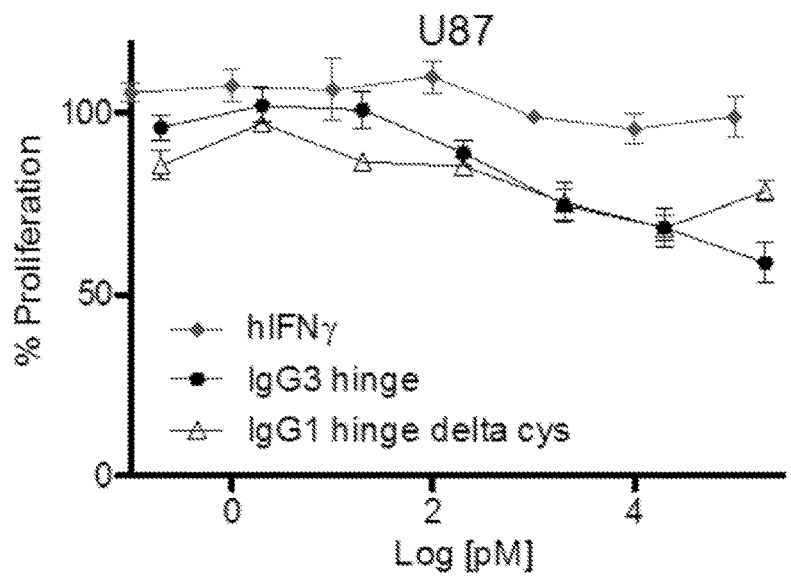
FIG. 10 shows that anti-CSPG4-fusions with IFNγ are more effective than IFNγ in inhibiting the growth the U87 glioblastoma. Data are expressed as the percent metabolic activity in the treated cells compared with untreated cells. Data are shown as the mean of triplicate samples±SD.

U87 cells were incubated with differing concentrations of the indicated fusion protein or with recombinant IFNγ for 6 days. The metabolic activity of the remaining cells was then measured using the MTS assay. As illustrated in FIG. 10, anti-CSPG4-fusions with IFNγ are more effective than IFNγ in inhibiting the growth of the U87 glioblastoma.

Figure 11:
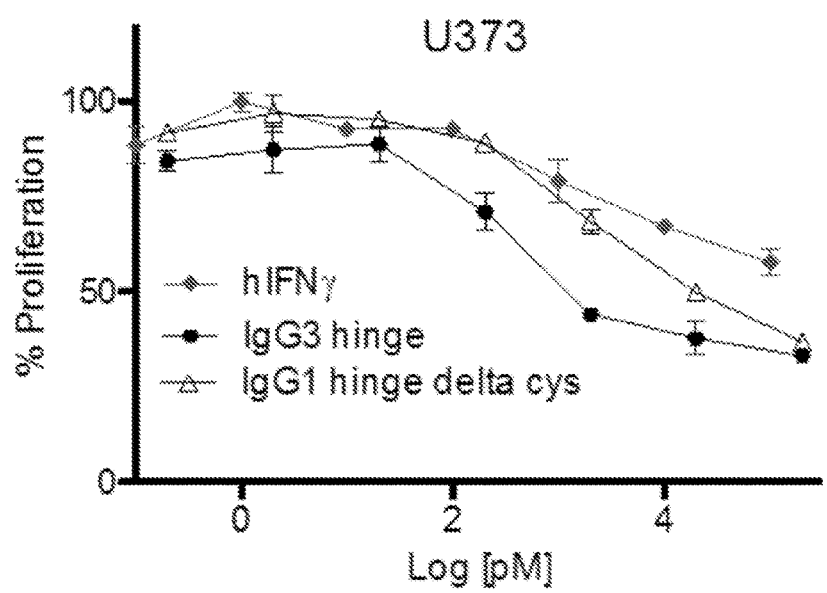
FIG. 11 shows that anti-CSPG4-fusions with IFNγ are more effective than IFNγ in inhibiting the growth the U373 glioblastoma. Data are expressed as the percent metabolic activity in the treated cells compared with untreated cells. Data are shown as the mean of triplicate samples±SD.

U373 cells were incubated with differing concentrations of the indicated fusion protein or with recombinant IFNγ for 6 days. The metabolic activity of the remaining cells was then measured using the MTS assay. As illustrated in FIG. 11, anti-CSPG4-fusions with IFNγ are more effective than IFNγ in inhibiting the growth of the U373 glioblastoma.

Figure 12:
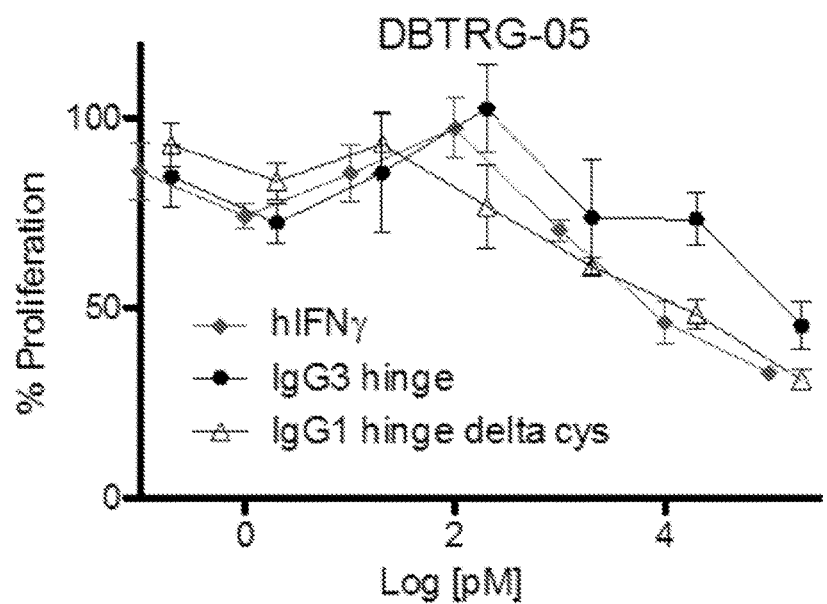
FIG. 12 shows that anti-CSPG4-fusions with IFNγ are as effective as IFNγ in inhibiting the growth the DBTRG-05 glioblastoma. Data are expressed as the percent metabolic activity in the treated cells compared with untreated cells. Data are shown as the mean of triplicate samples±SD.

DBTRG-05 glioblastoma cells were incubated with differing concentrations of the indicated fusion protein or with recombinant IFNγ for 6 days. DBTRG-05 expresses little to no CSPG4. The metabolic activity of the remaining cells was then measured using the MTS assay. As illustrated in FIG. 12 anti-CSPG4-fusions with IFNγ are as effective as IFNγ in inhibiting the growth the DBTRG-05 glioblastoma.

Figure 13:
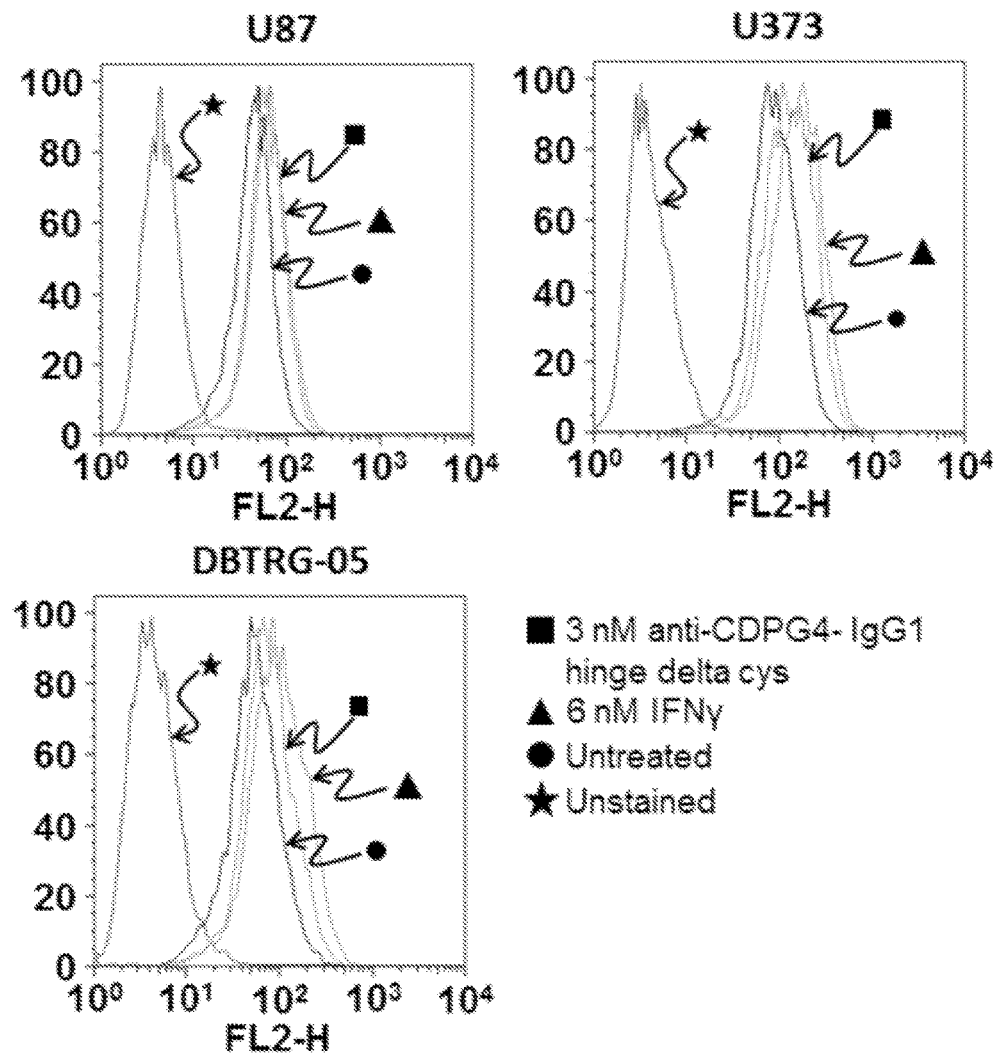
FIG. 13 shows that anti-CSPG4 IFNγ fusion proteins upregulate the expression of MHC 1 in glioblastoma cells. U87, U373 and DBTRG-05 glioblastoma cells were incubated with the indicated proteins for 24 hours. They were then detached using 2 mM EDTA, stained with anti-MHC 1, and analyzed by flow cytometry.

U87, U373 and DBTRG-05 glioblastoma cells were incubated with the indicated proteins (see FIG. 13) for 24 hours. They were then detached using 2 mM EDTA, stained with anti-MHC 1, and analyzed by flow cytometry. As illustrated in FIG. 13, anti-CSPG4 IFNγ fusion proteins upregulate the expression of MHC 1 in glioblastoma cells.

Figure 14:
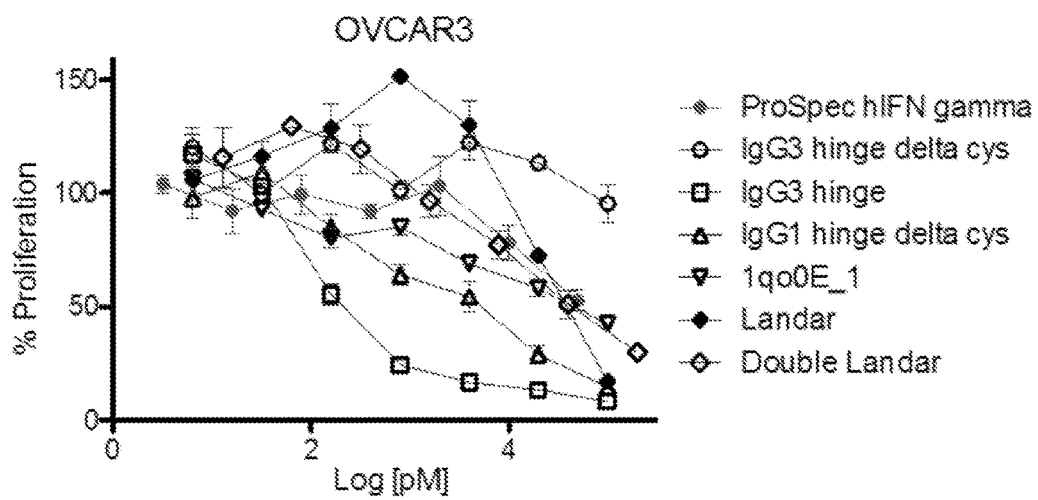
FIG. 14 shows that anti-CSPG4-fusions with IFNγ show differing activities against the OVCAR3 ovarian cancer depending on the linker used for the fusion protein. Data are expressed as the percent metabolic activity in the treated cells compared with untreated cells. Data are shown as the mean of triplicate samples±SD.

OVCAR3 cells were incubated with differing concentrations of the indicated fusion protein or with recombinant IFNγ for 6 days. The metabolic activity of the remaining cells was then measured using the MTS assay. As illustrated in FIG. 14, anti-CSPG4-fusions with IFNγ show differing activities against the OVCAR3 ovarian cancer depending on the linker used for the fusion protein.

Figure 15:
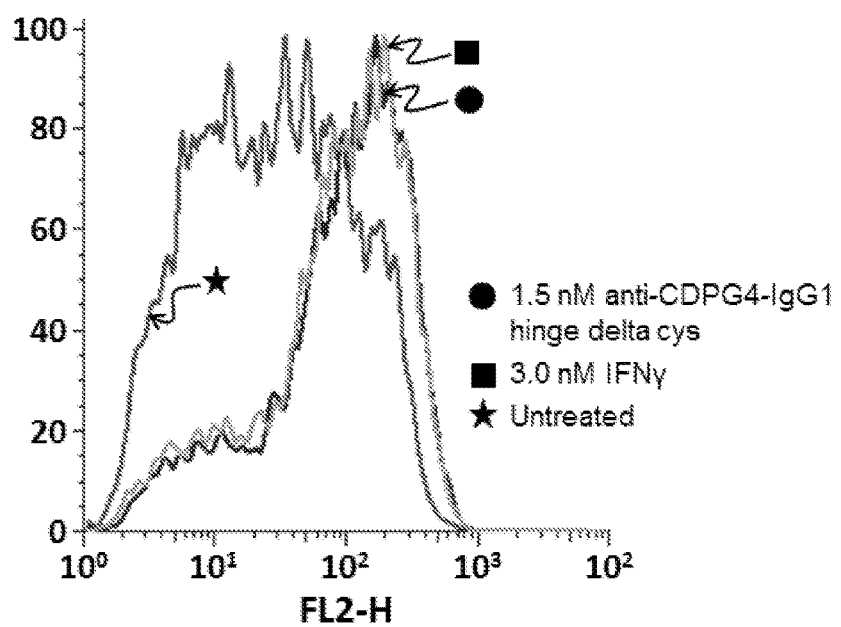
FIG. 15 shows that anti-CSPG4 IFNγ fusion proteins upregulate the expression of MHC 1 in OVCAR 3 ovarian cells. OVCAR 3 cells were incubated with the indicated proteins for 24 hours. They were then detached using 2 mM EDTA, stained with anti-MHC 1, and analyzed by flow cytometry.

OVCAR 3 cells were incubated with the indicated proteins for 24 hours. They were then detached using 2 mM EDTA, stained with anti-MHC 1, and analyzed by flow cytometry. As illustrated in FIG. 15, anti-CSPG4 IFNγ fusion proteins upregulate the expression of MHC 1 in OVCAR 3 ovarian cells.

Without being bound to a particular theory, it appears that the activity of the construct is strongly influenced by the linker sequence. In particular, constructs using the IgG1 and IgG3 hinges as linkers provided the highest activity.

In addition to cytotoxicity examined the ability of the fusions constructs to upregulate the expression of class I MHC, one of the activities of IFNγ, was determined. In this regard, the constructs appeared to be as active as IFNγ; those data are included.

It is also believed that the activity against glioblastoma is significant since this is typically such an untreatable tumor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A chimeric construct comprising an interferon attached to a full-length antibody that binds chondroitin sulfate proteoglycan 4 (CSPG4), where: said interferon is attached to said antibody by a peptide linker comprising the amino acid sequence LEPKSSDKTHTSPPSPGG (SEQ ID NO:75); said interferon is a mature interferon alpha 2 (SEQ ID NO: 12), or a mutant mature interferon alpha 2 comprising one or more mutations selected from the group consisting of E58A, E58L, E58N, H57A, H57M, H57Y, Q61A, Q61D, and Q61S relative to mature interferon alpha 2; and said construct when contacted to a cell that expresses or overexpresses CSPG4 cell results in the killing or inhibition of growth or proliferation of said cell.

2. The construct of claim 1, wherein said cell that expresses or overexpresses CSPG4 is a cancer cell.

3. The construct of claim 1, wherein said interferon comprises the mutations selected from the group consisting of
H57Y, E58N, and Q61S,
H57M, E58L, and Q61D,
H57Y, E58L, and Q61D,
E58A, and Q61S, and
E58A, and Q61A; wherein said mutations are relative to mature interferon alpha 2.

4. The construct of claim 1, wherein said antibody binds to a CSPG4 at an epitope bound by one or more antibodies selected from the group consisting of 9.2.27, 225.28, and 763.74.

5. The construct of claim 4, wherein said antibody comprises the VH and VL domain of an antibody selected from the group consisting of 9.2.27, 225.28, and 763.74.

6. The construct of claim 1, wherein said peptide linker joins said interferon to the carboxyl terminus of the CH3 domain of said antibody.

7. A pharmaceutical formulation comprising a construct of claim 1 in a pharmaceutically acceptable excipient.

8. The construct of claim 1, wherein said antibody is a full-length 9.2.27 antibody.

9. The construct of claim 8, wherein said antibody is a human IgG1.

10. The construct of claim 1, wherein said antibody is a full-length 225.28 antibody.

11. The construct of claim 1, wherein said antibody is a full-length 763.74 antibody.

\* \* \* \* \*

```
                     SEQUENCE LISTING

<160> NUMBER OF SEQ ID NOS: 95

<210> SEQ ID NO 1
    <211> LENGTH: 15
    <212> TYPE: PRT
    <213> ORGANISM: Artificial
    <220> FEATURE:
    <223> OTHER INFORMATION: Peptide linker

<400> SEQUENCE: 1

Gly Gly Gly Gly Ser Gly Gly Gly Gly Ser Gly Gly Gly Gly Ser
    1               5                   10                  15

<210> SEQ ID NO 2
    <211> LENGTH: 5
    <212> TYPE: PRT
    <213> ORGANISM: Artificial
    <220> FEATURE:
    <223> OTHER INFORMATION: Peptide linker

<400> SEQUENCE: 2

Gly Gly Gly Gly Ser
    1               5

<210> SEQ ID NO 3
    <211> LENGTH: 6
    <212> TYPE: PRT
    <213> ORGANISM: Artificial
    <220> FEATURE:
    <223> OTHER INFORMATION: Peptide linker

<400> SEQUENCE: 3

Ser Gly Gly Gly Gly Ser
    1               5

<210> SEQ ID NO 4
    <211> LENGTH: 12
    <212> TYPE: PRT
    <213> ORGANISM: Artificial
    <220> FEATURE:
    <223> OTHER INFORMATION: Peptide linker

<400> SEQUENCE: 4

Ala Glu Ala Ala Ala Lys Glu Ala Ala Ala Lys Ala
    1               5                   10

<210> SEQ ID NO 5
```

-continued

```
<211> LENGTH: 2322
<212> TYPE: PRT
<213> ORGANISM: Homo sapiens

<400> SEQUENCE: 5

Met Gln Ser Gly Pro Arg Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
            35                  40                  45

Ile Asp Leu Gln Leu Gln Phe Ser Thr Ser Gln Pro Glu Ala Leu Leu
50                  55                  60

Leu Leu Ala Ala Gly Pro Ala Asp His Leu Leu Gln Leu Tyr Ser
65                  70                  75                  80

Gly Arg Leu Gln Val Arg Leu Val Leu Gly Gln Glu Leu Arg Leu
                85                  90                  95

Gln Thr Pro Ala Glu Thr Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
```

```
385                 390                 395                 400
Leu Ala Pro Glu Ala Trp Pro Ala Met Glu Leu Pro Glu Pro Cys Val
                405                 410                 415
Pro Glu Pro Gly Leu Pro Pro Val Phe Ala Asn Phe Thr Gln Leu Leu
                420                 425                 430
Thr Ile Ser Pro Leu Val Val Ala Glu Gly Thr Ala Trp Leu Glu
            435                 440                 445
Trp Arg His Val Gln Pro Thr Leu Asp Leu Met Glu Ala Glu Leu Arg
        450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
                500                 505                 510
Asp Thr Ser Asp Gln Leu Val Leu Glu Val Ser Val Thr Ala Arg Val
            515                 520                 525
Pro Met Pro Ser Cys Leu Arg Arg Gly Gln Thr Tyr Leu Leu Pro Ile
        530                 535                 540
Gln Val Asn Pro Val Asn Asp Pro Pro His Ile Ile Phe Pro His Gly
545                 550                 555                 560
Ser Leu Met Val Ile Leu Glu His Thr Gln Lys Pro Leu Gly Pro Glu
                565                 570                 575
Val Phe Gln Ala Tyr Asp Pro Asp Ser Ala Cys Glu Gly Leu Thr Phe
            580                 585                 590
Gln Val Leu Gly Thr Ser Ser Gly Leu Pro Val Glu Arg Arg Asp Gln
        595                 600                 605
Pro Gly Glu Pro Ala Thr Glu Phe Ser Cys Arg Glu Leu Glu Ala Gly
    610                 615                 620
Ser Leu Val Tyr Val His Arg Gly Gly Pro Ala Gln Asp Leu Thr Phe
625                 630                 635                 640
Arg Val Ser Asp Gly Leu Gln Ala Ser Pro Pro Ala Thr Leu Lys Val
                645                 650                 655
Val Ala Ile Arg Pro Ala Ile Gln Ile His Arg Ser Thr Gly Leu Arg
                660                 665                 670
Leu Ala Gln Gly Ser Ala Met Pro Ile Leu Pro Ala Asn Leu Ser Val
            675                 680                 685
Glu Thr Asn Ala Val Gly Gln Asp Val Ser Val Leu Phe Arg Val Thr
        690                 695                 700
Gly Ala Leu Gln Phe Gly Glu Leu Gln Lys Gln Gly Ala Gly Gly Val
705                 710                 715                 720
Glu Gly Ala Glu Trp Trp Ala Thr Gln Ala Phe His Gln Arg Asp Val
                725                 730                 735
Glu Gln Gly Arg Val Arg Tyr Leu Ser Thr Asp Pro Gln His His Ala
                740                 745                 750
Tyr Asp Thr Val Glu Asn Leu Ala Leu Glu Val Gln Val Gly Gln Glu
            755                 760                 765
Ile Leu Ser Asn Leu Ser Phe Pro Val Thr Ile Gln Arg Ala Thr Val
        770                 775                 780
Trp Met Leu Arg Leu Glu Pro Leu His Thr Gln Asn Thr Gln Gln Glu
785                 790                 795                 800
Thr Leu Thr Thr Ala His Leu Glu Ala Thr Leu Glu Glu Ala Gly Pro
                805                 810                 815
```

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
            850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
            915                 920                 925

Ser Ala Ser Tyr Leu Tyr Glu Val Met Glu Arg Pro Arg His Gly Arg
            930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile
    1010                1015                1020

Ser Arg Ile Phe His Val Ala Arg Gly Gly Arg Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly
    1205                1210                1215

```
Pro Val His Thr Asp Ala Thr Leu Gln Val Thr Ile Ala Leu Glu
    1220                1225                1230

Gly Pro Leu Ala Pro Leu Lys Leu Val Arg His Lys Lys Ile Tyr
    1235                1240                1245

Val Phe Gln Gly Glu Ala Ala Glu Ile Arg Arg Asp Gln Leu Glu
    1250                1255                1260

Ala Ala Gln Glu Ala Val Pro Pro Ala Asp Ile Val Phe Ser Val
    1265                1270                1275

Lys Ser Pro Pro Ser Ala Gly Tyr Leu Val Met Val Ser Arg Gly
    1280                1285                1290

Ala Leu Ala Asp Glu Pro Pro Ser Leu Asp Pro Val Gln Ser Phe
    1295                1300                1305

Ser Gln Glu Ala Val Asp Thr Gly Arg Val Leu Tyr Leu His Ser
    1310                1315                1320

Arg Pro Glu Ala Trp Ser Asp Ala Phe Ser Leu Asp Val Ala Ser
    1325                1330                1335

Gly Leu Gly Ala Pro Leu Glu Gly Val Leu Val Glu Leu Glu Val
    1340                1345                1350

Leu Pro Ala Ala Ile Pro Leu Glu Ala Gln Asn Phe Ser Val Pro
    1355                1360                1365

Glu Gly Gly Ser Leu Thr Leu Ala Pro Pro Leu Leu Arg Val Ser
    1370                1375                1380

Gly Pro Tyr Phe Pro Thr Leu Leu Gly Leu Ser Leu Gln Val Leu
    1385                1390                1395

Glu Pro Pro Gln His Gly Ala Leu Gln Lys Glu Asp Gly Pro Gln
    1400                1405                1410

Ala Arg Thr Leu Ser Ala Phe Ser Trp Arg Met Val Glu Glu Gln
    1415                1420                1425

Leu Ile Arg Tyr Val His Asp Gly Ser Glu Thr Leu Thr Asp Ser
    1430                1435                1440

Phe Val Leu Met Ala Asn Ala Ser Glu Met Asp Arg Gln Ser His
    1445                1450                1455

Pro Val Ala Phe Thr Val Thr Val Leu Pro Val Asn Asp Gln Pro
    1460                1465                1470

Pro Ile Leu Thr Thr Asn Thr Gly Leu Gln Met Trp Glu Gly Ala
    1475                1480                1485

Thr Ala Pro Ile Pro Ala Glu Ala Leu Arg Ser Thr Asp Gly Asp
    1490                1495                1500

Ser Gly Ser Glu Asp Leu Val Tyr Thr Ile Glu Gln Pro Ser Asn
    1505                1510                1515

Gly Arg Val Val Leu Arg Gly Ala Pro Gly Thr Glu Val Arg Ser
    1520                1525                1530

Phe Thr Gln Ala Gln Leu Asp Gly Gly Leu Val Leu Phe Ser His
    1535                1540                1545

Arg Gly Thr Leu Asp Gly Gly Phe Arg Phe Arg Leu Ser Asp Gly
    1550                1555                1560

Glu His Thr Ser Pro Gly His Phe Phe Arg Val Thr Ala Gln Lys
    1565                1570                1575

Gln Val Leu Leu Ser Leu Lys Gly Ser Gln Thr Leu Thr Val Cys
    1580                1585                1590

Pro Gly Ser Val Gln Pro Leu Ser Ser Gln Thr Leu Arg Ala Ser
    1595                1600                1605

Ser Ser Ala Gly Thr Asp Pro Gln Leu Leu Leu Tyr Arg Val Val
```

```
                   1610                1615                1620
Arg Gly Pro Gln Leu Gly Arg Leu Phe His Ala Gln Gln Asp Ser
           1625                1630                1635
Thr Gly Glu Ala Leu Val Asn Phe Thr Gln Ala Glu Val Tyr Ala
           1640                1645                1650
Gly Asn Ile Leu Tyr Glu His Glu Met Pro Pro Glu Pro Phe Trp
           1655                1660                1665
Glu Ala His Asp Thr Leu Glu Leu Gln Leu Ser Ser Pro Pro Ala
           1670                1675                1680
Arg Asp Val Ala Ala Thr Leu Ala Val Ala Val Ser Phe Glu Ala
           1685                1690                1695
Ala Cys Pro Gln Arg Pro Ser His Leu Trp Lys Asn Lys Gly Leu
           1700                1705                1710
Trp Val Pro Glu Gly Gln Arg Ala Arg Ile Thr Val Ala Ala Leu
           1715                1720                1725
Asp Ala Ser Asn Leu Leu Ala Ser Val Pro Ser Pro Gln Arg Ser
           1730                1735                1740
Glu His Asp Val Leu Phe Gln Val Thr Gln Phe Pro Ser Arg Gly
           1745                1750                1755
Gln Leu Leu Val Ser Glu Glu Pro Leu His Ala Gly Gln Pro His
           1760                1765                1770
Phe Leu Gln Ser Gln Leu Ala Ala Gly Gln Leu Val Tyr Ala His
           1775                1780                1785
Gly Gly Gly Gly Thr Gln Gln Asp Gly Phe His Phe Arg Ala His
           1790                1795                1800
Leu Gln Gly Pro Ala Gly Ala Ser Val Ala Gly Pro Gln Thr Ser
           1805                1810                1815
Glu Ala Phe Ala Ile Thr Val Arg Asp Val Asn Glu Arg Pro Pro
           1820                1825                1830
Gln Pro Gln Ala Ser Val Pro Leu Arg Leu Thr Arg Gly Ser Arg
           1835                1840                1845
Ala Pro Ile Ser Arg Ala Gln Leu Ser Val Val Asp Pro Asp Ser
           1850                1855                1860
Ala Pro Gly Glu Ile Glu Tyr Glu Val Gln Arg Ala Pro His Asn
           1865                1870                1875
Gly Phe Leu Ser Leu Val Gly Gly Leu Gly Pro Val Thr Arg
           1880                1885                1890
Phe Thr Gln Ala Asp Val Asp Ser Gly Arg Leu Ala Phe Val Ala
           1895                1900                1905
Asn Gly Ser Ser Val Ala Gly Ile Phe Gln Leu Ser Met Ser Asp
           1910                1915                1920
Gly Ala Ser Pro Pro Leu Pro Met Ser Leu Ala Val Asp Ile Leu
           1925                1930                1935
Pro Ser Ala Ile Glu Val Gln Leu Arg Ala Pro Leu Glu Val Pro
           1940                1945                1950
Gln Ala Leu Gly Arg Ser Ser Leu Ser Gln Gln Gln Leu Arg Val
           1955                1960                1965
Val Ser Asp Arg Glu Glu Pro Glu Ala Ala Tyr Arg Leu Ile Gln
           1970                1975                1980
Gly Pro Gln Tyr Gly His Leu Leu Val Gly Gly Arg Pro Thr Ser
           1985                1990                1995
Ala Phe Ser Gln Phe Gln Ile Asp Gln Gly Glu Val Val Phe Ala
           2000                2005                2010
```

Phe Thr Asn Phe Ser Ser His Asp His Phe Arg Val Leu Ala
    2015                2020                2025

Leu Ala Arg Gly Val Asn Ala Ser Ala Val Val Asn Val Thr Val
    2030                2035                2040

Arg Ala Leu Leu His Val Trp Ala Gly Gly Pro Trp Pro Gln Gly
    2045                2050                2055

Ala Thr Leu Arg Leu Asp Pro Thr Val Leu Asp Ala Gly Glu Leu
    2060                2065                2070

Ala Asn Arg Thr Gly Ser Val Pro Arg Phe Arg Leu Leu Glu Gly
    2075                2080                2085

Pro Arg His Gly Arg Val Val Arg Val Pro Arg Ala Arg Thr Glu
    2090                2095                2100

Pro Gly Gly Ser Gln Leu Val Glu Gln Phe Thr Gln Gln Asp Leu
    2105                2110                2115

Glu Asp Gly Arg Leu Gly Leu Glu Val Gly Arg Pro Glu Gly Arg
    2120                2125                2130

Ala Pro Gly Pro Ala Gly Asp Ser Leu Thr Leu Glu Leu Trp Ala
    2135                2140                2145

Gln Gly Val Pro Pro Ala Val Ala Ser Leu Asp Phe Ala Thr Glu
    2150                2155                2160

Pro Tyr Asn Ala Ala Arg Pro Tyr Ser Val Ala Leu Leu Ser Val
    2165                2170                2175

Pro Glu Ala Ala Arg Thr Glu Ala Gly Lys Pro Glu Ser Ser Thr
    2180                2185                2190

Pro Thr Gly Glu Pro Gly Pro Met Ala Ser Ser Pro Glu Pro Ala
    2195                2200                2205

Val Ala Lys Gly Gly Phe Leu Ser Phe Leu Glu Ala Asn Met Phe
    2210                2215                2220

Ser Val Ile Ile Pro Met Cys Leu Val Leu Leu Leu Ala Leu
    2225                2230                2235

Ile Leu Pro Leu Leu Phe Tyr Leu Arg Lys Arg Asn Lys Thr Gly
    2240                2245                2250

Lys His Asp Val Gln Val Leu Thr Ala Lys Pro Arg Asn Gly Leu
    2255                2260                2265

Ala Gly Asp Thr Glu Thr Phe Arg Lys Val Glu Pro Gly Gln Ala
    2270                2275                2280

Ile Pro Leu Thr Ala Val Pro Gly Gln Gly Pro Pro Gly Gly
    2285                2290                2295

Gln Pro Asp Pro Glu Leu Leu Gln Phe Cys Arg Thr Pro Asn Pro
    2300                2305                2310

Ala Leu Lys Asn Gly Gln Tyr Trp Val
    2315                2320

<210> SEQ ID NO 6
<211> LENGTH: 8305
<212> TYPE: DNA
<213> ORGANISM: Homo sapiens

<400> SEQUENCE: 6
gcgcccagga gcagagccgc gctcgctcca ctcagctccc agctcccagg actccgctgg      60
ctcctcgcaa gtcctgccgc ccagcccgcc gggatgcagt ccgggccgcg gcccccactt     120
ccagcccccg gctggccctt ggctttgacc ctgactatgt tggccagact tgcatccgcg     180
gcttccttct tcggtgagaa ccacctggag gtgcctgtgg ccacggctct gaccgacata     240

```
gacctgcagc tgcagttctc cacgtcccag cccgaagccc tccttctcct ggcagcaggc      300
ccagctgacc acctcctgct gcagctctac tctggacgcc tgcaggtcag acttgttctg      360
ggccaggagg agctgaggct gcagactcca gcagagacgc tgctgagtga ctccatcccc      420
cacactgtgg tgctgactgt cgtagagggc tgggccacgt tgtcagtcga tgggtttctg      480
aacgcctcct cagcagtccc aggagccccc ctagaggtcc cctatgggct ctttgttggg      540
ggcactggga cccttggcct gccctacctg aggggaacca gccgacccct gaggggttgc      600
ctccatgcag ccaccctcaa tggccgcagc ctcctccggc tctgaccccc gatgtgcat      660 gagggctgtg ctgaagagtt ttctgccagt gatgatgtgg ccctgggctt ctctgggccc      720
cactctctgg ctgccttccc tgcctggggc actcaggacg aaggaaccct agagtttaca      780
ctcaccacac agagccggca ggcacccttg gccttccagg caggggggccg gcgtggggac      840 ttcatctatg tggacatatt tgagggccac ctgcgggccg tggtggagaa gggccagggt      900
accgtattgc tccacaacag tgtgcctgtg gccgatgggc agccccatga ggtcagtgtc      960
cacatcaatg ctcaccggct ggaaatctcc gtggaccagt accctacgca tacttcgaac     1020
cgaggagtcc tcagctacct ggagccacgg ggcagtctcc ttctcggggg gctggatgca     1080
gaggcctctc gtcacctcca ggaacaccgc ctgggcctga caccagaggc caccaatgcc     1140
tccctgctgg gctgcatgga agacctcagt gtcaatggcc agaggcgggg gctgcgggaa     1200
gctttgctga cgcgcaacat ggcagccggc tgcaggctgg aggaggagga gtatgaggac     1260
gatgcctatg gacattatga agctttctcc accctggccc ctgaggcttg gccagccatg     1320
gagctgcctg agccatgcgt gcctgagcca gggctgcctc ctgtctttgc caatttcacc     1380
cagctgctga ctatcagccc actggtggtg gccgaggggg gcacagcctg gcttgagtgg     1440
aggcatgtgc agcccacgct ggacctgatg gaggctgagc tgcgcaaatc ccaggtgctg     1500
ttcagcgtga cccgaggggc acgccatggc gagctcgagc tggacatccc gggagcccag     1560
gcacgaaaaa tgttcaccct cctggacgtg gtgaaccgca aggcccgctt catccacgat     1620
ggctctgagg acacctccga ccagctggtg ctggaggtgt cggtgacggc tcgggtgccc     1680
atgccctcat gccttcggag gggccaaaca tacctcctgc ccatccaggt caaccctgtc     1740
aatgacccac cccacatcat cttcccacat ggcagcctca tggtgatcct ggaacacacg     1800
cagaagccgc tggggcctga ggttttccag gcctatgacc cggactctgc ctgtgagggc     1860
ctcaccttcc aggtccttgg cacctcctct ggcctccccg tggagcgccg agaccagcct     1920
ggggagccgg cgaccgagtt ctcctgccgg gagttggagg ccggcagcct agtctatgtc     1980
caccgcggtg gtcctgcaca ggacttgacg ttccgggtca gcgatggact gcaggccagc     2040
cccccggcca cgctgaaggt ggtggccatc cggccggcca tacagatcca ccgcagcaca     2100
gggttgcgac tggcccaagg ctctgccatg cccatcttgc ccgccaacct gtcggtggag     2160
accaatgccg tggggcagga tgtgagcgtg ctgttccgcg tcactgggc cctgcagttt     2220 ggggagctgc agaagcaggg gcaggtgggg gtggagggtg ctgagtggtg ggccacacag     2280
gcgttccacc agcgggatgt ggagcagggc cgcgtgaggt acctgagcac tgacccacag     2340
caccacgctt acgacaccgt ggagaacctg gccctggagg tgcaggtggg ccaggagatc     2400
ctgagcaatc tgtccttccc agtgaccatc cagagagcca ctgtgtggat gctgcggctg     2460
gagccactgc acactcagaa cacccagcag gagaccctca ccacagccca cctggaggcc     2520
accctggagg aggcaggccc aagcccccca accttccatt atgaggtggt tcaggctccc     2580
```

```
aggaaaggca accttcaact acagggcaca aggctgtcag atggccaggg cttcacccag    2640
gatgacatac aggctggccg ggtgacctat ggggccacag cacgtgcctc agaggcagtc    2700
gaggacacct tccgtttccg tgtcacagct ccaccatatt tctccccact ctataccttc    2760
cccatccaca ttggtggtga cccagatgcg cctgtcctca ccaatgtcct cctcgtggtg    2820
cctgagggtg gtgagggtgt cctctctgct gaccacctct tgtcaagag tctcaacagt     2880 gccagctacc tctatgaggt catggagcgg ccccgccatg ggaggttggc ttggcgtggg    2940
acacaggaca agaccactat ggtgacatcc ttcaccaatg aagacctgtt gcgtggccgg    3000
ctggtctacc agcatgatga ctccgagacc acagaagatg atatcccatt tgttgctacc    3060
cgccagggcg agagcagtgg tgacatggcc tgggaggagg tacggggtgt cttccgagtg    3120
gccatccagc ccgtgaatga ccacgcccct gtgcagacca tcagccggat cttccatgtg    3180 gccccggggtg ggcggcggct gctgactaca gacgacgtgg ccttcagcga tgctgactcg    3240
ggctttgctg acgcccagct ggtgcttacc cgcaaggacc tcctctttgg cagtatcgtg    3300
gccgtagatg agcccacgcg gcccatctac cgcttcaccc aggaggacct caggaagagg    3360
cgagtactgt tcgtgcactc aggggctgac cgtggctgga tccagctgca ggtgtccgac    3420
gggcaacacc aggccactgc gctgctggag gtgcaggcct cggaacccta cctccgtgtg    3480
gccaacggct ccagccttgt ggtccctcaa ggaggccagg gcaccatcga cacggccgtg    3540
ctccacctgg acaccaacct cgacatccgc agtggggatg aggtccacta ccacgtcaca    3600
gctggccctc gctggggaca gctagtccgg gctggtcagc cagccacagc cttctcccag    3660
caggacctgc tggatggggc cgttctctat agccacaatg gcagcctcag ccccgcgac    3720 accatggcct tctccgtgga agcagggcca gtgcacacgg atgccaccct acaagtgacc    3780
attgccctag agggcccact ggccccactg aagctggtcc ggcacaagaa gatctacgtc    3840
ttccagggag aggcagctga gatcagaagg gaccagctgg aggcagccca ggaggcagtg    3900
ccacctgcag acatcgtatt ctcagtgaag agcccaccga gtgccggcta cctggtgatg    3960
gtgtcgcgtg gcgccttggc agatgagcca cccagcctgg accctgtgca gagcttctcc    4020
caggaggcag tggacacagg cagggtcctg tacctgcact cccgccctga ggcctggagc    4080
gatgccttct cgctggatgt ggcctcaggc ctgggtgctc ccctcgaggg cgtccttgtg    4140
gagctggagg tgctgccgc tgccatccca ctagaggcgc aaaacttcag cgtccctgag    4200
ggtggcagcc tcaccctggc ccctccactg ctccgtgtct ccgggcccta cttccccact    4260
ctcctgggcc tcagcctgca ggtgctggag ccacccagc atggagccct gcagaaggag    4320
gacggacctc aagccaggac cctcagcgcc ttcctcctgga gaatggtgga agagcagctg    4380
atccgctacg tgcatgacgg gagcgagaca ctgacagaca gttttgtcct gatggctaat    4440
gcctccgaga tggatcgcca gagccatcct gtggccttca ctgtcactgt cctgcctgtc    4500
aatgaccaac cccccatcct cactacaaac acaggcctgc agatgtggga gggggccact    4560
gcgcccatcc ctgcggaggc tctgaggagc acggacggcg actctgggtc tgaggatctg    4620
gtctacacca tcgagcagcc cagcaacggg cgggtagtgc tgcggggggc gccgggcact    4680
gaggtgcgca gcttcacgca ggcccagctg acggcgggc tcgtgctgtt ctcacacaga    4740
ggaaccctgg atggaggctt ccgcttccgc ctctctgacg gcgagcacac ttccccgga    4800 cacttcttcc gagtgacggc ccagaagcaa gtgctcctct cgctgaaggg cagccagaca    4860
ctgactgtct gccagggtc cgtccagcca ctcagcagtc agaccctcag ggccagctcc    4920
agcgcaggca ctgacccca gctcctgctc taccgtgtgg tgcggggccc ccagctaggc    4980
```

```
cggctgttcc acgcccagca ggacagcaca ggggaggccc tggtgaactt cactcaggca    5040
gaggtctacg ctgggaatat tctgtatgag catgagatgc cccccgagcc cttttgggag    5100
gcccatgata ccctagagct ccagctgtcc tcgccgcctg cccgggacgt ggccgccacc    5160
cttgctgtgg ctgtgtcttt tgaggctgcc tgtcccagc gccccagcca cctctggaag    5220
aacaaaggtc tctgggtccc cgagggccag cgggccagga tcaccgtggc tgctctggat    5280
gcctccaatc tcttggccag cgttccatca ccccagcgct cagagcatga tgtgctcttc    5340
caggtcacac agttccccag ccggggccag ctgttggtgt ccgaggagcc cctccatgct    5400
gggcagcccc acttcctgca gtcccagctg gctgcagggc agctagtgta tgcccacggc    5460
ggtgggggca cccagcagga tggcttccac tttcgtgccc acctccaggg gccagcaggg    5520
gcctccgtgg ctggacccca aacctcagag gcctttgcca tcacggtgag ggatgtaaat    5580
gagcggcccc ctcagccaca ggcctctgtc ccactccggc tcacccgagg ctctcgtgcc    5640
cccatctccc gggcccagct gagtgtggtg gacccagact cagctcctgg ggagattgag    5700
tacgaggtcc agcgggcacc ccacaacggc ttcctcagcc tggtgggtgg tggcctgggg    5760
cccgtgaccc gcttcacgca agccgatgtg gattcagggc ggctggcctt cgtggccaac    5820
gggagcagcg tggcaggcat cttccagctg agcatgtctg atggggccag cccaccccctg   5880
cccatgtccc tggctgtgga catcctacca tccgccatcg aggtgcagct gcgggcaccc    5940
ctggaggtgc cccaagcttt ggggcgctcc tcactgagcc agcagcagct ccgggtggtt    6000
tcagatcggg aggagccaga ggcagcatac cgcctcatcc agggacccca gtatgggcat    6060
ctcctggtgg gcgggcggcc cacctcggcc ttcagccaat tccagataga ccagggcgag    6120
gtggtctttg ccttcaccaa cttctcctcc tctcatgacc acttcagagt cctggcactg    6180
gctagggtg tcaatgcatc agccgtagtg aacgtcactg tgagggctct gctgcatgtg    6240
tgggcaggtg ggccatggcc ccagggtgcc accctgcgcc tggaccccac cgtcctagat    6300
gctggcgagc tggccaaccg cacaggcagt gtgccgcgct tccgcctcct ggagggaccc    6360
cggcatggcc gcgtggtccg cgtgccccga gccaggacgg agcccggggg cagccagctg    6420
gtggagcagt tcactcagca ggaccttgag gacgggaggc tgggctgga ggtgggcagg    6480
ccagagggga gggcccccgg ccccgcaggt gacagtctca ctctggagct gtgggcacag    6540
ggcgtcccgc ctgctgtggc ctccctggac tttgccactg agccttacaa tgctgcccgg    6600
ccctacagcg tggccctgct cagtgtcccc gaggccgccc ggacggaagc agggaagcca    6660
gagagcagca cccccacagg cgagccaggc cccatggcat ccagccctga gcccgctgtg    6720
gccaagggag gcttcctgag cttccttgag gccaacatgt tcagcgtcat catccccatg    6780
tgcctggtac ttctgctcct ggcgctcatc ctgcccctgc tcttctacct ccgaaaacgc    6840
aacaagacgg gcaagcatga cgtccaggtc ctgactgcca agccccgcaa cggcctggct    6900
ggtgacaccg agacctttcg caaggtggag ccaggcagg ccatcccgct cacagctgtg    6960
cctggccagg ggccccctcc aggaggccag cctgacccag agctgctgca gttctgccgg    7020
acacccaacc ctgcccttaa gaatggccag tactgggtgt gaggcctggc ctgggcccag    7080
atgctgatcg ggcagggac aggcttgccc atgtcccggg ccccattgct tccatgcctg    7140
gtgctgtctg agtatccca gagcaagaga gacctggaga caccaggggt ggagggtcct    7200
gggagatagt cccaggggtc cggacagag tggagtcaag agctggaacc tccctcagct    7260
cactccgagc ctggagaact gcaggggcca aggtggaggc aggcttaagt tcagtcctcc    7320
```

```
tgccctggag ctggtttggg ctgtcaaaac cagggtaacc tcctacatgg gtcatgactc   7380
tgggtcctgg gtctgtgacc ttgggtaagt cgcgcctgac ccaggctgct aagagggcaa   7440
ggagaaggaa gtaccctggg gagggaaggg acagaggaag ctattcctgg cttttccact   7500
ccaacccagg ccacccttgg tctctgcccc agagttgaga aaaaaacttc ctcccctggt   7560
tttttaggga gatggtatcc cctggagtag agggcaagag gagagagcgc ctccagtcta   7620
gaaggcataa gccaatagga taatatattc agggtgcagg gtgggtaggt tgctctgggg   7680
atgggtttat ttaagggaga ttgcaaggaa gctatttaac atggtgctga gctagccagg   7740
actgatggag cccctggggg tgtgggatgg aggagggtct gcagccagtt cattcccagg   7800
gccccatctt gatgggccaa gggctaaaca tgcatgtgtc agtggctttg gagcaggtta   7860
ggctggggct catcgagggt ctcaggccga ggccactgcg gtgccagtgc cccctgaggg   7920
actagggcag gcagctgggg gcacttggtt ccatggagcc tggataaaca gtgctttgga   7980
ggctctggac agctgtgtgg tgtttgtgtc ttaactatgc actgggccct tgtctgcgtc   8040
ggcttgcata cagagggccc ctgggtcgg ccctccggcc tggcctcagc cagtgggatg   8100
gacagggcca ggcaggcctc tgaacttcca cctcctgggg cctcccagac ctcctgtgcc   8160
cccacctgtg tgggcaggtg ggccagtctt cgggtgatgg gaccaaaccc cttcagttca   8220
gtagagaaag gctaggtcct ctacaaagag ctgcaagaca aaattaaaa taaatgctcc   8280 ccaccctaga aaaaaaaaaa aaaaa                                          8305
```

```
<210> SEQ ID NO 7
<211> LENGTH: 112
<212> TYPE: PRT
<213> ORGANISM: Artificial
<220> FEATURE:
<223> OTHER INFORMATION: Antibody VL domain

<400> SEQUENCE: 7

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ser Gly Thr Lys Leu Glu Ile Lys Arg
            100                 105                 110

<210> SEQ ID NO 8
<211> LENGTH: 121
<212> TYPE: PRT
<213> ORGANISM: Artificial
<220> FEATURE:
<223> OTHER INFORMATION: Antibody VH domain

<400> SEQUENCE: 8

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
```

```
                    20                  25                  30
Trp Met Asn Trp Val Lys Gln Arg Pro Gly Gln Gly Leu Glu Trp Ile
                35                  40                  45
Gly Arg Ile Tyr Pro Gly Asp Gly Asp Thr Asn Tyr Asn Gly Lys Phe
            50                  55                  60
Lys Gly Lys Ala Thr Leu Thr Ala Asp Lys Ser Ser Thr Ala Tyr
 65                  70                  75                  80
Met Gln Val Ser Ser Leu Thr Ser Val Asp Ser Ala Val Tyr Phe Cys
                85                  90                  95
Ala Arg Gly Asn Thr Val Val Val Pro Tyr Thr Met Asp Tyr Trp Gly
                100                 105                 110
Gln Gly Thr Ser Val Thr Val Ser Ser
                115                 120

<210> SEQ ID NO 9
<211> LENGTH: 184
<212> TYPE: PRT
<213> ORGANISM: Artificial
<220> FEATURE:
<223> OTHER INFORMATION: Truncated interferon beta

<400> SEQUENCE: 9

Met Gly Lys Met Ala Ser Leu Phe Ala Thr Phe Leu Val Val Leu Val
 1               5                  10                  15
Ser Leu Ser Leu Ala Ser Glu Ser Ser Ala Cys Asp Leu Pro Gln Thr
                20                  25                  30
His Ser Leu Gly Ser Arg Arg Thr Leu Met Leu Leu Ala Gln Met Arg
                35                  40                  45
Arg Ile Ser Leu Phe Ser Cys Leu Lys Asp Arg His Asp Phe Gly Phe
            50                  55                  60
Pro Gln Glu Glu Phe Gly Asn Gln Phe Gln Lys Ala Glu Thr Ile Pro
 65                  70                  75                  80
Val Leu His Glu Met Ile Gln Gln Ile Phe Asn Leu Phe Ser Thr Lys
                85                  90                  95
Asp Ser Ser Ala Ala Trp Asp Glu Thr Leu Leu Asp Lys Phe Tyr Thr
                100                 105                 110
Glu Leu Tyr Gln Gln Leu Asn Asp Leu Glu Ala Cys Val Ile Gln Gly
                115                 120                 125
Val Gly Val Thr Glu Thr Pro Leu Met Lys Glu Asp Ser Ile Leu Ala
                130                 135                 140
Val Arg Lys Tyr Phe Gln Arg Ile Thr Leu Tyr Leu Lys Glu Lys Lys
145                 150                 155                 160
Tyr Ser Pro Cys Ala Trp Glu Val Val Arg Ala Glu Ile Met Arg Ser
                165                 170                 175
Phe Ser Leu Ser Thr Asn Leu Gln
                180

<210> SEQ ID NO 10
<211> LENGTH: 183
<212> TYPE: PRT
<213> ORGANISM: Artificial
<220> FEATURE:
<223> OTHER INFORMATION: Truncated interferon beta

<400> SEQUENCE: 10

Met Gly Lys Met Ala Ser Leu Phe Ala Thr Phe Leu Val Val Leu Val
 1               5                  10                  15
```

```
Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
                100                 105                 110

Glu Leu Tyr Gln Gln Leu Asn Asp Leu Glu Ala Cys Val Ile Gln Gly
            115                 120                 125

Val Gly Val Thr Glu Thr Pro Leu Met Lys Glu Asp Ser Ile Leu Ala
        130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu
            180

<210> SEQ ID NO 11
<211> LENGTH: 182
<212> TYPE: PRT
<213> ORGANISM: Artificial
<220> FEATURE:
<223> OTHER INFORMATION: Truncated interferon beta

<400> SEQUENCE: 11

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
                100                 105                 110

Glu Leu Tyr Gln Gln Leu Asn Asp Leu Glu Ala Cys Val Ile Gln Gly
            115                 120                 125

Val Gly Val Thr Glu Thr Pro Leu Met Lys Glu Asp Ser Ile Leu Ala
        130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn
            180
```

<210> SEQ ID NO 12
<211> LENGTH: 165
<212> TYPE: PRT
<213> ORGANISM: Homo sapiens

<400> SEQUENCE: 12

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 13
<211> LENGTH: 165
<212> TYPE: PRT
<213> ORGANISM: Homo sapiens

<400> SEQUENCE: 13

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 14
<211> LENGTH: 166
<212> TYPE: PRT
<213> ORGANISM: Artificial
<220> FEATURE:
<223> OTHER INFORMATION: Modified interferon alpha-c

<400> SEQUENCE: 14

Cys Asp Leu Pro Gln Thr His Ser Leu Gly Asn Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
            165

<210> SEQ ID NO 15
<211> LENGTH: 165
<212> TYPE: PRT
<213> ORGANISM: Artificial
<220> FEATURE:
<223> OTHER INFORMATION: Modified interferon alpha-c

<400> SEQUENCE: 15

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 16
<211> LENGTH: 166
<212> TYPE: PRT
<213> ORGANISM: Artificial
<220> FEATURE:
<223> OTHER INFORMATION: Modified interferon alpha-d

<400> SEQUENCE: 16

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 17
<211> LENGTH: 166
<212> TYPE: PRT
<213> ORGANISM: Artificial
<220> FEATURE:
<223> OTHER INFORMATION: Modified interferon alpha-5

<400> SEQUENCE: 17

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu

```
                85                  90                  95

Glu Ala Cys Met Met Gln Glu Val Gly Val Glu Asp Thr Pro Leu Met
                100                 105                 110

Asn Val Asp Ser Ile Leu Thr Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 18
<211> LENGTH: 166
<212> TYPE: PRT
<213> ORGANISM: Artificial
<220> FEATURE:
<223> OTHER INFORMATION: Modified interferon alpha-6

<400> SEQUENCE: 18

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn Gln Phe
            35                  40                  45

Gln Lys Ala Glu Ala Ile Ser Val Leu His Glu Val Ile Gln Gln Thr
        50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 19
<211> LENGTH: 166
<212> TYPE: PRT
<213> ORGANISM: Artificial
<220> FEATURE:
<223> OTHER INFORMATION: Modified interferon alpha-4

<400> SEQUENCE: 19

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
                20                  25                  30

Arg His Asp Phe Gly Phe Pro Glu Glu Glu Phe Asp Gly His Gln Phe
            35                  40                  45
```

```
Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 20
<211> LENGTH: 166
<212> TYPE: PRT
<213> ORGANISM: Artificial
<220> FEATURE:
<223> OTHER INFORMATION: Modified interferon alpha-4b

<400> SEQUENCE: 20

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
                20                  25                  30

Arg His Asp Phe Gly Phe Pro Glu Glu Glu Phe Asp Gly His Gln Phe
            35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 21
<211> LENGTH: 166
<212> TYPE: PRT
<213> ORGANISM: Artificial
<220> FEATURE:
<223> OTHER INFORMATION: Modified interferon alpha-I

<400> SEQUENCE: 21

Cys Asp Leu Pro Gln Thr His Ser Leu Gly Asn Arg Arg Ala Leu Ile
1               5                   10                  15
```

```
Leu Leu Ala Gln Met Gly Arg Ile Ser Pro Phe Ser Cys Leu Lys Asp
                20                  25                  30

Arg His Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
     50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Met Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 22
<211> LENGTH: 166
<212> TYPE: PRT
<213> ORGANISM: Artificial
<220> FEATURE:
<223> OTHER INFORMATION: Modified interferon alpha-j

<400> SEQUENCE: 22

Cys Asp Leu Pro Gln Thr His Ser Leu Arg Asn Arg Arg Ala Leu Ile
 1               5                  10                  15

Leu Leu Ala Gln Met Gly Arg Ile Ser Pro Phe Ser Cys Leu Lys Asp
                20                  25                  30

Arg His Glu Phe Arg Phe Pro Glu Glu Glu Phe Asp Gly His Gln Phe
            35                  40                  45

Gln Lys Thr Gln Ala Ile Ser Val Leu His Glu Met Ile Gln Gln Thr
     50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 23
<211> LENGTH: 166
<212> TYPE: PRT
<213> ORGANISM: Artificial
```

<220> FEATURE:
<223> OTHER INFORMATION: Modified interferon alpha-H

<400> SEQUENCE: 23

```
Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 24
<211> LENGTH: 166
<212> TYPE: PRT
<213> ORGANISM: Artificial
<220> FEATURE:
<223> OTHER INFORMATION: Modified interferon alpha-F

<400> SEQUENCE: 24

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
```

<210> SEQ ID NO 25
<211> LENGTH: 166
<212> TYPE: PRT
<213> ORGANISM: Artificial
<220> FEATURE:
<223> OTHER INFORMATION: Modified interferon alpha-8

<400> SEQUENCE: 25

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 26
<211> LENGTH: 165
<212> TYPE: PRT
<213> ORGANISM: Artificial
<220> FEATURE:
<223> OTHER INFORMATION: Modified interferon alpha-consensus

<400> SEQUENCE: 26

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Pro Gln Glu Glu Phe Asp Gly Asn Gln Phe Gln
        35                  40                  45

Lys Ala Gln Ala Ile Ser Val Leu His Glu Met Ile Gln Gln Thr Phe
    50                  55                  60

Asn Leu Phe Ser Thr Lys Asp Ser Ser Ala Ala Trp Asp Glu Ser Leu
65                  70                  75                  80

Leu Glu Lys Phe Tyr Thr Glu Leu Tyr Gln Gln Leu Asn Asp Leu Glu
                85                  90                  95

Ala Cys Val Ile Gln Glu Val Gly Val Glu Glu Thr Pro Leu Met Asn
            100                 105                 110

Val Asp Ser Ile Leu Ala Val Lys Lys Tyr Phe Gln Arg Ile Thr Leu
        115                 120                 125

Tyr Leu Thr Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Arg
145                 150                 155                 160

Leu Arg Arg Lys Glu
                165

<210> SEQ ID NO 27
<211> LENGTH: 166
<212> TYPE: PRT
<213> ORGANISM: Homo sapiens

<400> SEQUENCE: 27

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 28
<211> LENGTH: 142
<212> TYPE: PRT
<213> ORGANISM: Homo sapiens

<400> SEQUENCE: 28

Asp Pro Tyr Val Lys Glu Ala Glu Asn Leu Lys Lys Tyr Phe Asn Ala
1               5                   10                  15

Gly His Ser Asp Val Ala Asp Asn Gly Thr Leu Phe Leu Gly Ile Leu
            20                  25                  30

Lys Asn Trp Lys Glu Glu Ser Asp Arg Lys Ile Met Gln Ser Gln Ile
        35                  40                  45

Val Ser Phe Tyr Phe Lys Leu Phe Lys Asn Phe Lys Asp Asp Gln Ser
    50                  55                  60

Ile Gln Lys Ser Val Glu Thr Ile Lys Glu Asp Met Asn Val Lys Phe
65                  70                  75                  80

Phe Asn Ser Asn Lys Lys Lys Arg Asp Asp Phe Glu Lys Leu Thr Asn
                85                  90                  95

Tyr Ser Val Thr Asp Leu Asn Val Gln Arg Lys Ala Ile His Glu Leu
            100                 105                 110

Ile Gln Val Met Ala Glu Leu Ser Pro Ala Ala Lys Thr Gly Lys Arg
            115                 120                 125

Lys Arg Ser Gln Met Leu Phe Gln Gly Arg Arg Ala Ser Gln
    130                 135                 140

<210> SEQ ID NO 29
<211> LENGTH: 133
<212> TYPE: PRT
<213> ORGANISM: Artificial
<220> FEATURE:
<223> OTHER INFORMATION: Truncated interferon

<400> SEQUENCE: 29

Asp Pro Tyr Val Lys Glu Ala Glu Asn Leu Lys Lys Tyr Phe Asn Ala
1               5                   10                  15

Gly His Ser Asp Val Ala Asp Asn Gly Thr Leu Phe Leu Gly Ile Leu
            20                  25                  30

Lys Asn Trp Lys Glu Glu Ser Asp Arg Lys Ile Met Gln Ser Gln Ile
        35                  40                  45

Val Ser Phe Tyr Phe Lys Leu Phe Lys Asn Phe Lys Asp Asp Gln Ser
    50                  55                  60

Ile Gln Lys Ser Val Glu Thr Ile Lys Glu Asp Met Asn Val Lys Phe
65                  70                  75                  80

Phe Asn Ser Asn Lys Lys Lys Arg Asp Asp Phe Glu Lys Leu Thr Asn
                85                  90                  95

Tyr Ser Val Thr Asp Leu Asn Val Gln Arg Lys Ala Ile His Glu Leu
            100                 105                 110

Ile Gln Val Met Ala Glu Leu Ser Pro Ala Ala Lys Thr Gly Lys Arg
        115                 120                 125

Lys Arg Ser Gln Met
    130

<210> SEQ ID NO 30
<211> LENGTH: 12
<212> TYPE: PRT
<213> ORGANISM: Artificial
<220> FEATURE:
<223> OTHER INFORMATION: Peptide linker

<400> SEQUENCE: 30

Gly Gly Gly Ser Gly Gly Gly Ser Gly Gly Gly Ser
1               5                   10

<210> SEQ ID NO 31
<211> LENGTH: 5
<212> TYPE: PRT
<213> ORGANISM: Artificial
<220> FEATURE:
<223> OTHER INFORMATION: Peptide linker

<400> SEQUENCE: 31

Gly Gly Gly Gly Ser
1               5

<210> SEQ ID NO 32
<211> LENGTH: 6
<212> TYPE: PRT
<213> ORGANISM: Artificial
<220> FEATURE:
<223> OTHER INFORMATION: Peptide linker

<400> SEQUENCE: 32

```
Ser Gly Gly Gly Gly Ser
1               5

<210> SEQ ID NO 33
<211> LENGTH: 10
<212> TYPE: PRT
<213> ORGANISM: Artificial
<220> FEATURE:
<223> OTHER INFORMATION: Peptide linker

<400> SEQUENCE: 33

Gly Gly Gly Gly Ser Gly Gly Gly Gly Ser
1               5                   10

<210> SEQ ID NO 34
<211> LENGTH: 7
<212> TYPE: PRT
<213> ORGANISM: Artificial
<220> FEATURE:
<223> OTHER INFORMATION: Peptide linker

<400> SEQUENCE: 34

Ala Glu Ala Ala Ala Lys Ala
1               5

<210> SEQ ID NO 35
<211> LENGTH: 12
<212> TYPE: PRT
<213> ORGANISM: Artificial
<220> FEATURE:
<223> OTHER INFORMATION: Peptide linker

<400> SEQUENCE: 35

Ala Glu Ala Ala Ala Lys Glu Ala Ala Ala Lys Ala
1               5                   10

<210> SEQ ID NO 36
<211> LENGTH: 17
<212> TYPE: PRT
<213> ORGANISM: Artificial
<220> FEATURE:
<223> OTHER INFORMATION: Peptide linker

<400> SEQUENCE: 36

Ala Glu Ala Ala Ala Lys Glu Ala Ala Ala Lys Glu Ala Ala Ala Lys
1               5                   10                  15

Ala

<210> SEQ ID NO 37
<211> LENGTH: 22
<212> TYPE: PRT
<213> ORGANISM: Artificial
<220> FEATURE:
<223> OTHER INFORMATION: Peptide linker

<400> SEQUENCE: 37

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 38
<211> LENGTH: 27
<212> TYPE: PRT
<213> ORGANISM: Artificial
<220> FEATURE:
```

<223> OTHER INFORMATION: Peptide linker

<400> SEQUENCE: 38

Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Ala
            20                  25

<210> SEQ ID NO 39
<211> LENGTH: 13
<212> TYPE: PRT
<213> ORGANISM: Artificial
<220> FEATURE:
<223> OTHER INFORMATION: Peptide linker

<400> SEQUENCE: 39

Ala Glu Ala Ala Ala Lys Glu Ala Ala Ala Lys Ala Gly
1               5                   10

<210> SEQ ID NO 40
<211> LENGTH: 14
<212> TYPE: PRT
<213> ORGANISM: Artificial
<220> FEATURE:
<223> OTHER INFORMATION: Peptide linker

<400> SEQUENCE: 40

Ala Glu Ala Ala Ala Lys Glu Ala Ala Ala Lys Ala Gly Ser
1               5                   10

<210> SEQ ID NO 41
<211> LENGTH: 5
<212> TYPE: PRT
<213> ORGANISM: Artificial
<220> FEATURE:
<223> OTHER INFORMATION: Peptide linker

<400> SEQUENCE: 41

Gly Gly Gly Gly Gly
1               5

<210> SEQ ID NO 42
<211> LENGTH: 5
<212> TYPE: PRT
<213> ORGANISM: Artificial
<220> FEATURE:
<223> OTHER INFORMATION: Peptide linker

<400> SEQUENCE: 42

Gly Gly Ala Gly Gly
1               5

<210> SEQ ID NO 43
<211> LENGTH: 8
<212> TYPE: PRT
<213> ORGANISM: Artificial
<220> FEATURE:
<223> OTHER INFORMATION: Peptide linker

<400> SEQUENCE: 43

Gly Gly Gly Gly Gly Gly Gly Gly
1               5

<210> SEQ ID NO 44
<211> LENGTH: 10
<212> TYPE: PRT

```
<213> ORGANISM: Artificial
<220> FEATURE:
<223> OTHER INFORMATION: Peptide linker

<400> SEQUENCE: 44

Gly Ala Gly Ala Gly Ala Gly Ala Gly Ala
1               5                   10

<210> SEQ ID NO 45
<211> LENGTH: 18
<212> TYPE: PRT
<213> ORGANISM: Artificial
<220> FEATURE:
<223> OTHER INFORMATION: Peptide linker

<400> SEQUENCE: 45

Arg Pro Leu Ser Tyr Arg Pro Pro Phe Pro Phe Gly Phe Pro Ser Val
1               5                   10                  15

Arg Pro

<210> SEQ ID NO 46
<211> LENGTH: 18
<212> TYPE: PRT
<213> ORGANISM: Artificial
<220> FEATURE:
<223> OTHER INFORMATION: Peptide linker

<400> SEQUENCE: 46

Tyr Pro Arg Ser Ile Tyr Ile Arg Arg His Pro Ser Pro Ser Leu
1               5                   10                  15

Thr Thr

<210> SEQ ID NO 47
<211> LENGTH: 18
<212> TYPE: PRT
<213> ORGANISM: Artificial
<220> FEATURE:
<223> OTHER INFORMATION: Peptide linker

<400> SEQUENCE: 47

Thr Pro Ser His Leu Ser His Ile Leu Pro Ser Phe Gly Leu Pro Thr
1               5                   10                  15

Phe Asn

<210> SEQ ID NO 48
<211> LENGTH: 18
<212> TYPE: PRT
<213> ORGANISM: Artificial
<220> FEATURE:
<223> OTHER INFORMATION: Peptide linker

<400> SEQUENCE: 48

Arg Pro Val Ser Pro Phe Thr Phe Pro Arg Leu Ser Asn Ser Trp Leu
1               5                   10                  15

Pro Ala

<210> SEQ ID NO 49
<211> LENGTH: 18
<212> TYPE: PRT
<213> ORGANISM: Artificial
<220> FEATURE:
<223> OTHER INFORMATION: Peptide linker

<400> SEQUENCE: 49
```

```
Ser Pro Ala Ala His Phe Pro Arg Ser Ile Pro Arg Pro Gly Pro Ile
1               5                   10                  15

Arg Thr

<210> SEQ ID NO 50
<211> LENGTH: 18
<212> TYPE: PRT
<213> ORGANISM: Artificial
<220> FEATURE:
<223> OTHER INFORMATION: Peptide linker

<400> SEQUENCE: 50

Ala Pro Gly Pro Ser Ala Pro Ser His Arg Ser Leu Pro Ser Arg Ala
1               5                   10                  15

Phe Gly

<210> SEQ ID NO 51
<211> LENGTH: 18
<212> TYPE: PRT
<213> ORGANISM: Artificial
<220> FEATURE:
<223> OTHER INFORMATION: Peptide linker

<400> SEQUENCE: 51

Pro Arg Asn Ser Ile His Phe Leu His Pro Leu Leu Val Ala Pro Leu
1               5                   10                  15

Gly Ala

<210> SEQ ID NO 52
<211> LENGTH: 18
<212> TYPE: PRT
<213> ORGANISM: Artificial
<220> FEATURE:
<223> OTHER INFORMATION: Peptide linker

<400> SEQUENCE: 52

Met Pro Ser Leu Ser Gly Val Leu Gln Val Arg Tyr Leu Ser Pro Pro
1               5                   10                  15

Asp Leu

<210> SEQ ID NO 53
<211> LENGTH: 18
<212> TYPE: PRT
<213> ORGANISM: Artificial
<220> FEATURE:
<223> OTHER INFORMATION: Peptide linker

<400> SEQUENCE: 53

Ser Pro Gln Tyr Pro Ser Pro Leu Thr Leu Thr Leu Pro Pro His Pro
1               5                   10                  15

Ser Leu

<210> SEQ ID NO 54
<211> LENGTH: 18
<212> TYPE: PRT
<213> ORGANISM: Artificial
<220> FEATURE:
<223> OTHER INFORMATION: Peptide linker

<400> SEQUENCE: 54

Asn Pro Ser Leu Asn Pro Pro Ser Tyr Leu His Arg Ala Pro Ser Arg
1               5                   10                  15

Ile Ser
```

<210> SEQ ID NO 55
<211> LENGTH: 17
<212> TYPE: PRT
<213> ORGANISM: Artificial
<220> FEATURE:
<223> OTHER INFORMATION: Peptide linker

<400> SEQUENCE: 55

Leu Pro Trp Arg Thr Ser Leu Leu Pro Ser Leu Pro Leu Arg Arg Arg
1               5                   10                  15

Pro

<210> SEQ ID NO 56
<211> LENGTH: 18
<212> TYPE: PRT
<213> ORGANISM: Artificial
<220> FEATURE:
<223> OTHER INFORMATION: Peptide linker

<400> SEQUENCE: 56

Pro Pro Leu Phe Ala Lys Gly Pro Val Gly Leu Leu Ser Arg Ser Phe
1               5                   10                  15

Pro Pro

<210> SEQ ID NO 57
<211> LENGTH: 18
<212> TYPE: PRT
<213> ORGANISM: Artificial
<220> FEATURE:
<223> OTHER INFORMATION: Peptide linker

<400> SEQUENCE: 57

Val Pro Pro Ala Pro Val Val Ser Leu Arg Ser Ala His Ala Arg Pro
1               5                   10                  15

Pro Tyr

<210> SEQ ID NO 58
<211> LENGTH: 17
<212> TYPE: PRT
<213> ORGANISM: Artificial
<220> FEATURE:
<223> OTHER INFORMATION: Peptide linker

<400> SEQUENCE: 58

Leu Arg Pro Thr Pro Arg Val Arg Ser Tyr Thr Cys Cys Pro Thr
1               5                   10                  15

Pro

<210> SEQ ID NO 59
<211> LENGTH: 18
<212> TYPE: PRT
<213> ORGANISM: Artificial
<220> FEATURE:
<223> OTHER INFORMATION: Peptide linker

<400> SEQUENCE: 59

Pro Asn Val Ala His Val Leu Pro Leu Leu Thr Val Pro Trp Asp Asn
1               5                   10                  15

Leu Arg

<210> SEQ ID NO 60
<211> LENGTH: 18

```
<212> TYPE: PRT
<213> ORGANISM: Artificial
<220> FEATURE:
<223> OTHER INFORMATION: Peptide linker

<400> SEQUENCE: 60

Cys Asn Pro Leu Leu Pro Leu Cys Ala Arg Ser Pro Ala Val Arg Thr
1               5                   10                  15

Phe Pro

<210> SEQ ID NO 61
<211> LENGTH: 14
<212> TYPE: PRT
<213> ORGANISM: Artificial
<220> FEATURE:
<223> OTHER INFORMATION: Peptide linker

<400> SEQUENCE: 61

Leu Gly Thr Pro Thr Pro Thr Pro Thr Pro Thr Gly Glu Phe
1               5                   10

<210> SEQ ID NO 62
<211> LENGTH: 8
<212> TYPE: PRT
<213> ORGANISM: Artificial
<220> FEATURE:
<223> OTHER INFORMATION: Peptide linker

<400> SEQUENCE: 62

Glu Asp Phe Thr Arg Gly Lys Leu
1               5

<210> SEQ ID NO 63
<211> LENGTH: 21
<212> TYPE: PRT
<213> ORGANISM: Artificial
<220> FEATURE:
<223> OTHER INFORMATION: Peptide linker

<400> SEQUENCE: 63

Leu Glu Ala Ala Ala Arg Glu Ala Ala Ala Arg Glu Ala Ala Ala Arg
1               5                   10                  15

Glu Ala Ala Ala Arg
            20

<210> SEQ ID NO 64
<211> LENGTH: 16
<212> TYPE: PRT
<213> ORGANISM: Artificial
<220> FEATURE:
<223> OTHER INFORMATION: Peptide linker

<400> SEQUENCE: 64

Leu Glu Ala Ala Ala Arg Glu Ala Ala Ala Arg Glu Ala Ala Ala Arg
1               5                   10                  15

<210> SEQ ID NO 65
<211> LENGTH: 11
<212> TYPE: PRT
<213> ORGANISM: Artificial
<220> FEATURE:
<223> OTHER INFORMATION: Peptide linker

<400> SEQUENCE: 65

Leu Glu Ala Ala Ala Arg Glu Ala Ala Ala Arg
1               5                   10
```

<210> SEQ ID NO 66
<211> LENGTH: 6
<212> TYPE: PRT
<213> ORGANISM: Artificial
<220> FEATURE:
<223> OTHER INFORMATION: Peptide linker

<400> SEQUENCE: 66

Leu Glu Ala Ala Ala Arg
1               5

<210> SEQ ID NO 67
<211> LENGTH: 20
<212> TYPE: PRT
<213> ORGANISM: Artificial
<220> FEATURE:
<223> OTHER INFORMATION: Peptide linker

<400> SEQUENCE: 67

Glu Ala Ala Ala Arg Glu Ala Ala Ala Arg Glu Ala Ala Ala Arg Glu
1               5                   10                  15

Ala Ala Ala Arg
            20

<210> SEQ ID NO 68
<211> LENGTH: 15
<212> TYPE: PRT
<213> ORGANISM: Artificial
<220> FEATURE:
<223> OTHER INFORMATION: Peptide linker

<400> SEQUENCE: 68

Glu Ala Ala Ala Arg Glu Ala Ala Ala Arg Glu Ala Ala Ala Arg
1               5                   10                  15

<210> SEQ ID NO 69
<211> LENGTH: 10
<212> TYPE: PRT
<213> ORGANISM: Artificial
<220> FEATURE:
<223> OTHER INFORMATION: Peptide linker

<400> SEQUENCE: 69

Glu Ala Ala Ala Arg Glu Ala Ala Ala Arg
1               5                   10

<210> SEQ ID NO 70
<211> LENGTH: 5
<212> TYPE: PRT
<213> ORGANISM: Artificial
<220> FEATURE:
<223> OTHER INFORMATION: Peptide linker

<400> SEQUENCE: 70

Glu Ala Ala Ala Arg
1               5

<210> SEQ ID NO 71
<211> LENGTH: 10
<212> TYPE: PRT
<213> ORGANISM: Artificial
<220> FEATURE:
<223> OTHER INFORMATION: Peptide linker

<400> SEQUENCE: 71

Leu Thr Glu Glu Gln Gln Glu Gly Gly Gly
1               5                   10

<210> SEQ ID NO 72
<211> LENGTH: 9
<212> TYPE: PRT
<213> ORGANISM: Artificial
<220> FEATURE:
<223> OTHER INFORMATION: Peptide linker

<400> SEQUENCE: 72

Thr Glu Glu Gln Gln Glu Gly Gly Gly
1               5

<210> SEQ ID NO 73
<211> LENGTH: 19
<212> TYPE: PRT
<213> ORGANISM: Artificial
<220> FEATURE:
<223> OTHER INFORMATION: Peptide linker

<400> SEQUENCE: 73

Leu Ala Lys Leu Lys Gln Lys Thr Glu Gln Leu Gln Asp Arg Ile Ala
1               5                   10                  15

Gly Gly Gly

<210> SEQ ID NO 74
<211> LENGTH: 65
<212> TYPE: PRT
<213> ORGANISM: Artificial
<220> FEATURE:
<223> OTHER INFORMATION: Peptide linker

<400> SEQUENCE: 74

Leu Glu Leu Lys Thr Pro Leu Gly Asp Thr Thr His Thr Cys Pro Arg
1               5                   10                  15

Cys Pro Glu Pro Lys Ser Cys Asp Thr Pro Pro Cys Pro Arg Cys
                20                  25                  30

Pro Glu Pro Lys Ser Cys Asp Thr Pro Pro Cys Pro Arg Cys Pro
            35                  40                  45

Glu Pro Lys Ser Cys Asp Thr Pro Pro Cys Pro Arg Cys Pro Gly
        50                  55                  60

Gly
65

<210> SEQ ID NO 75
<211> LENGTH: 18
<212> TYPE: PRT
<213> ORGANISM: Artificial
<220> FEATURE:
<223> OTHER INFORMATION: Peptide linker

<400> SEQUENCE: 75

Leu Glu Pro Lys Ser Ser Asp Lys Thr His Thr Ser Pro Pro Ser Pro
1               5                   10                  15

Gly Gly

<210> SEQ ID NO 76
<211> LENGTH: 30
<212> TYPE: DNA
<213> ORGANISM: Artificial
<220> FEATURE:
<223> OTHER INFORMATION: Nucleic acid encoding peptide linker

<400> SEQUENCE: 76
cttaccgagg agcagcagga gggcggcggc                                30

<210> SEQ ID NO 77
<211> LENGTH: 185
<212> TYPE: PRT
<213> ORGANISM: Artificial
<220> FEATURE:
<223> OTHER INFORMATION: Peptide linker

<400> SEQUENCE: 77

Leu Thr Glu Glu Gln Gln Glu Gly Gly Gly Met Lys Tyr Thr Ser Tyr
1               5                   10                  15

Ile Leu Ala Phe Gln Leu Cys Ile Val Leu Gly Ser Leu Gly Cys Tyr
            20                  25                  30

Cys Gln Asp Pro Tyr Val Lys Glu Ala Glu Asn Leu Lys Lys Tyr Phe
        35                  40                  45

Asn Ala Gly His Ser Asp Val Ala Asp Asn Gly Thr Leu Phe Leu Gly
    50                  55                  60

Ile Leu Lys Asn Trp Lys Glu Glu Ser Asp Arg Lys Ile Met Gln Ser
65                  70                  75                  80

Gln Ile Val Ser Phe Tyr Phe Lys Leu Phe Lys Asn Phe Lys Asp Asp
                85                  90                  95

Gln Ser Ile Gln Lys Ser Val Glu Thr Ile Lys Glu Asp Met Asn Val
            100                 105                 110

Lys Phe Phe Asp Ser Asn Lys Lys Lys Arg Asp Asp Phe Glu Lys Leu
        115                 120                 125

Thr Asn Tyr Ser Val Thr Asp Leu Asn Val Gln Arg Lys Ala Ile His
    130                 135                 140

Glu Leu Ile Gln Val Met Ala Glu Leu Ser Pro Ala Ala Lys Thr Gly
145                 150                 155                 160

Lys Arg Lys Arg Ser Gln Met Leu Phe Gln Gly Arg Arg Ala Ser Gln
                165                 170                 175

Thr Glu Glu Gln Gln Glu Gly Gly Gly
            180                 185

<210> SEQ ID NO 78
<211> LENGTH: 558
<212> TYPE: DNA
<213> ORGANISM: Artificial
<220> FEATURE:
<223> OTHER INFORMATION: Nucleic acid encoding peptide linker

<400> SEQUENCE: 78
cttaccgagg agcagcagga gggcggcggc atgaaatata caagttatat cttggctttt    60
cagctctgca tcgttttggg ttctcttggc tgttactgcc aggacccata tgtaaaagaa   120
gcagaaaacc ttaagaaata ttttaatgca ggtcattcag atgtagcgga taatggaact   180
cttttcttag catttgtgaa gaattggaaa gaggagagtg acagaaaaat aatgcagagc   240
caaattgtct cctttttactt caaacttttt aaaaacttta agatgaccaa gagcatccaa   300
aagagtgtgg agaccatcaa ggaagacatg aatgtcaagt ttttcaatag caacaaaaag   360
aaacgagatg acttcgaaaa gctgactaat tattcggtaa ctgacttgaa tgtccaacgc   420
aaagcaatac atgaactcat ccaagtgatg gctgaactgt cgccagcagc taaaacaggg   480
aagcgaaaaa ggagtcagat gctgtttcga ggtcgaagag catcccagta aaccgaggag   540
cagcaggagg cggcggc                                                  558

<210> SEQ ID NO 79
<211> LENGTH: 57
<212> TYPE: DNA
<213> ORGANISM: Artificial
<220> FEATURE:
<223> OTHER INFORMATION: Nucleic acid encoding peptide linker

<400> SEQUENCE: 79
cttgctaaat taaaacaaaa aactgaacaa ttacaagatc gtattgctgg tggcggc    57

<210> SEQ ID NO 80
<211> LENGTH: 195
<212> TYPE: DNA
<213> ORGANISM: Artificial
<220> FEATURE:
<223> OTHER INFORMATION: Nucleic acid encoding peptide linker

<400> SEQUENCE: 80
cttgagctca aaccccact tggtgacaca actcacacat gcccacggtg cccagagccc     60
aaatcttgtg acacacctcc ccgtgccca aggtgcccag agcccaaatc ttgtgacaca    120
cctcccccgt gcccaaggtg cccagagccc aaatcttgtg acacacctcc ccgtgccca    180 aggtgcccag gcggc                                                    195

<210> SEQ ID NO 81
<211> LENGTH: 54
<212> TYPE: DNA
<213> ORGANISM: Artificial
<220> FEATURE:
<223> OTHER INFORMATION: Nucleic acid encoding peptide linker

<400> SEQUENCE: 81
cttgagccca atcttccga caaaactcac acatctccac cgtccccagg cggc    54

<210> SEQ ID NO 82
<211> LENGTH: 144
<212> TYPE: PRT
<213> ORGANISM: Artificial
<220> FEATURE:
<223> OTHER INFORMATION: Landar hIFN gamma

<400> SEQUENCE: 82

Leu Thr Glu Glu Gln Gln Glu Gly Gly Gly Gln Asp Pro Tyr Val Lys
1               5                   10                  15

Glu Ala Glu Asn Leu Lys Lys Tyr Phe Asn Ala Gly His Ser Asp Val
            20                  25                  30

Ala Asp Asn Gly Thr Leu Phe Leu Gly Ile Leu Lys Asn Trp Lys Glu
        35                  40                  45

Glu Ser Asp Arg Lys Ile Met Gln Ser Gln Ile Val Ser Phe Tyr Phe
    50                  55                  60

Lys Leu Phe Lys Asn Phe Lys Asp Asp Gln Ser Ile Gln Lys Ser Val
65                  70                  75                  80

Glu Thr Ile Lys Glu Asp Met Asn Val Lys Phe Phe Asn Ser Asn Lys
                85                  90                  95

Lys Lys Arg Asp Asp Phe Glu Lys Leu Thr Asn Tyr Ser Val Thr Asp
            100                 105                 110

Leu Asn Val Gln Arg Lys Ala Ile His Glu Leu Ile Gln Val Met Ala
        115                 120                 125

Glu Leu Ser Pro Ala Ala Lys Thr Gly Lys Arg Lys Arg Ser Gln Met
    130                 135                 140

<210> SEQ ID NO 83
<211> LENGTH: 432
<212> TYPE: DNA
<213> ORGANISM: Artificial
<220> FEATURE:
<223> OTHER INFORMATION: Nucleic acid encoding Landar hIFN gamma

<400> SEQUENCE: 83

```
cttaccgagg agcagcagga gggcggcggc caggatccct acgtgaagga ggccgagaac    60
ctgaagaagt acttcaacgc cggccactcc gacgtggccg acaacggcac cctgttcctg   120
ggcatcctga gaactggaa ggaggagtcc gacaggaaga tcatgcagtc ccagatcgtg    180
tccttctact tcaagctgtt caagaacttc aaggacgacc agtccatcca gaagtccgtg   240
gagaccatca aggaggacat gaacgtgaag ttcttcaact ccaacaagaa gaagagggac   300
gacttcgaga agctgaccaa ctactccgtg accgacctga acgtgcagag gaaggccatc   360
cacgagctga tccaggtgat ggccgagctg tcccccgccg ccaagaccgg caagaggaag   420
aggtcccaga tg                                                       432
```

<210> SEQ ID NO 84
<211> LENGTH: 287
<212> TYPE: PRT
<213> ORGANISM: Artificial
<220> FEATURE:
<223> OTHER INFORMATION: Double Landar hIFN gamma

<400> SEQUENCE: 84

```
Leu Thr Glu Glu Gln Gln Glu Gly Gly Gly Gln Asp Pro Tyr Val Lys
  1               5                  10                  15

Glu Ala Glu Asn Leu Lys Lys Tyr Phe Asn Ala Gly His Ser Asp Val
             20                  25                  30

Ala Asp Asn Gly Thr Leu Phe Leu Gly Ile Leu Lys Asn Trp Lys Glu
         35                  40                  45

Glu Ser Asp Arg Lys Ile Met Gln Ser Gln Ile Val Ser Phe Tyr Phe
     50                  55                  60

Lys Leu Phe Lys Asn Phe Lys Asp Asp Gln Ser Ile Gln Lys Ser Val
 65                  70                  75                  80

Glu Thr Ile Lys Glu Asp Met Asn Val Lys Phe Phe Asn Ser Asn Lys
                 85                  90                  95

Lys Lys Arg Asp Asp Phe Glu Lys Leu Thr Asn Tyr Ser Val Thr Asp
            100                 105                 110

Leu Asn Val Gln Arg Lys Ala Ile His Glu Leu Ile Gln Val Met Ala
        115                 120                 125

Glu Leu Ser Pro Ala Ala Lys Thr Gly Lys Arg Lys Arg Ser Gln Met
    130                 135                 140

Thr Glu Glu Gln Gln Glu Gly Gly Gly Gln Asp Pro Tyr Val Lys Glu
145                 150                 155                 160

Ala Glu Asn Leu Lys Lys Tyr Phe Asn Ala Gly His Ser Asp Val Ala
                165                 170                 175

Asp Asn Gly Thr Leu Phe Leu Gly Ile Leu Lys Asn Trp Lys Glu Glu
            180                 185                 190

Ser Asp Arg Lys Ile Met Gln Ser Gln Ile Val Ser Phe Tyr Phe Lys
        195                 200                 205

Leu Phe Lys Asn Phe Lys Asp Asp Gln Ser Ile Gln Lys Ser Val Glu
    210                 215                 220
```

-continued

```
Thr Ile Lys Glu Asp Met Asn Val Lys Phe Phe Asn Ser Asn Lys Lys
225                 230                 235                 240

Lys Arg Asp Asp Phe Glu Lys Leu Thr Asn Tyr Ser Val Thr Asp Leu
            245                 250                 255

Asn Val Gln Arg Lys Ala Ile His Glu Leu Ile Gln Val Met Ala Glu
        260                 265                 270

Leu Ser Pro Ala Ala Lys Thr Gly Lys Arg Lys Arg Ser Gln Met
        275                 280                 285
```

<210> SEQ ID NO 85
<211> LENGTH: 861
<212> TYPE: DNA
<213> ORGANISM: Artificial
<220> FEATURE:
<223> OTHER INFORMATION: Nucleic acid encoding double Landar hIFN gamma

<400> SEQUENCE: 85

```
cttaccgagg agcagcagga gggcggcggc caggaccct acgtgaagga ggccgagaac    60
ctgaagaagt acttcaacgc cggccactcc gacgtggccg acaacggcac cctgttcctg   120
ggcatcctga gaactggaa ggaggagtcc gacaggaaga tcatgcagtc ccagatcgtg   180
tccttctact tcaagctgtt caagaacttc aaggacgacc agtccatcca gaagtccgtg   240
gagaccatca aggaggacat gaacgtgaag ttcttcaact ccaacaagaa gagagggac    300
gacttcgaga agctgaccaa ctactccgtg accgacctga cgtgcagag aaggccatc    360
cacgagctga tccaggtgat ggccgagctg tcccccgccg ccaagaccgg caagaggaag   420
aggtcccaga tgaccgagga gcagcaggag ggcggcggcc aggatcccta cgtgaaggag   480
gccgagaacc tgaagaagta cttcaacgcc ggccactccg acgtggccga caacggcacc   540
ctgttcctgg gcatcctgaa gaactggaag gaggagtccg acaggaagat catgcagtcc   600
cagatcgtgt ccttctactt caagctgttc aagaacttca aggacgacca gtccatccag   660
aagtccgtgg agaccatcaa ggaggacatg aacgtgaagt tcttcaactc caacaagaag   720
agagggacg acttcgagaa gctgaccaac tactccgtga ccgacctgaa cgtgcagagg   780
aaggccatcc acgagctgat ccaggtgatg gccgagctgt cccccgccgc caagaccggc   840
aagaggaaga ggtcccagat g                                             861
```

<210> SEQ ID NO 86
<211> LENGTH: 153
<212> TYPE: PRT
<213> ORGANISM: Artificial
<220> FEATURE:
<223> OTHER INFORMATION: 1qoOE1 human IFN gamma

<400> SEQUENCE: 86

```
Leu Ala Lys Leu Lys Gln Lys Thr Glu Gln Leu Gln Asp Arg Ile Ala
1               5                   10                  15

Gly Gly Gly Gln Asp Pro Tyr Val Lys Glu Ala Glu Asn Leu Lys Lys
            20                  25                  30

Tyr Phe Asn Ala Gly His Ser Asp Val Ala Asp Asn Gly Thr Leu Phe
        35                  40                  45

Leu Gly Ile Leu Lys Asn Trp Lys Glu Glu Ser Asp Arg Lys Ile Met
    50                  55                  60

Gln Ser Gln Ile Val Ser Phe Tyr Phe Lys Leu Phe Lys Asn Phe Lys
65                  70                  75                  80

Asp Asp Gln Ser Ile Gln Lys Ser Val Glu Thr Ile Lys Glu Asp Met
                85                  90                  95
```

```
Asn Val Lys Phe Phe Asn Ser Asn Lys Lys Arg Asp Asp Phe Glu
            100                 105                 110

Lys Leu Thr Asn Tyr Ser Val Thr Asp Leu Asn Val Gln Arg Lys Ala
            115                 120                 125

Ile His Glu Leu Ile Gln Val Met Ala Glu Leu Ser Pro Ala Ala Lys
    130                 135                 140

Thr Gly Lys Arg Lys Arg Ser Gln Met
145                 150
```

<210> SEQ ID NO 87
<211> LENGTH: 459
<212> TYPE: DNA
<213> ORGANISM: Artificial
<220> FEATURE:
<223> OTHER INFORMATION: Nucleic acid encoding 1qo0E1 human IFN gamma

<400> SEQUENCE: 87

```
cttgctaaat taaaacaaaa aactgaacaa ttacaagatc gtattgctgg tggcggccag      60
gatccctacg tgaaggaggc cgagaacctg aagaagtact caacgccgg ccactccgac     120
gtggccgaca acggcaccct gttcctgggc atcctgaaga ctggaagga ggagtccgac     180
aggaagatca tgcagtccca gatcgtgtcc ttctacttca agctgttcaa gaacttcaag     240
gacgaccagt ccatccagaa gtccgtggag accatcaagg aggacatgaa cgtgaagttc     300
ttcaactcca acaagaagaa gagggacgac ttcgagaagc tgaccaacta ctccgtgacc     360
gacctgaacg tgcagaggaa ggccatccac gagctgatcc aggtgatggc cgagctgtcc     420
cccgccgcca agaccggcaa gaggaagagg tcccagatg                            459
```

<210> SEQ ID NO 88
<211> LENGTH: 199
<212> TYPE: PRT
<213> ORGANISM: Artificial
<220> FEATURE:
<223> OTHER INFORMATION: IgG3 hinge-hIFN gamma

<400> SEQUENCE: 88

```
Leu Glu Leu Lys Thr Pro Leu Gly Asp Thr Thr His Thr Cys Pro Arg
1               5                   10                  15

Cys Pro Glu Pro Lys Ser Cys Asp Thr Pro Pro Cys Pro Arg Cys
            20                  25                  30

Pro Glu Pro Lys Ser Cys Asp Thr Pro Pro Cys Pro Arg Cys Pro
        35                  40                  45

Glu Pro Lys Ser Cys Asp Thr Pro Pro Cys Pro Arg Cys Pro Gly
    50                  55                  60

Gly Gln Asp Pro Tyr Val Lys Glu Ala Glu Asn Leu Lys Lys Tyr Phe
65                  70                  75                  80

Asn Ala Gly His Ser Asp Val Ala Asp Asn Gly Thr Leu Phe Leu Gly
                85                  90                  95

Ile Leu Lys Asn Trp Lys Glu Glu Ser Asp Arg Lys Ile Met Gln Ser
            100                 105                 110

Gln Ile Val Ser Phe Tyr Phe Lys Leu Phe Lys Asn Phe Lys Asp Asp
        115                 120                 125

Gln Ser Ile Gln Lys Ser Val Glu Thr Ile Lys Glu Asp Met Asn Val
    130                 135                 140

Lys Phe Phe Asn Ser Asn Lys Lys Arg Asp Asp Phe Glu Lys Leu
145                 150                 155                 160
```

Thr Asn Tyr Ser Val Thr Asp Leu Asn Val Gln Arg Lys Ala Ile His
                    165                 170                 175

Glu Leu Ile Gln Val Met Ala Glu Leu Ser Pro Ala Ala Lys Thr Gly
            180                 185                 190

Lys Arg Lys Arg Ser Gln Met
        195

<210> SEQ ID NO 89
<211> LENGTH: 597
<212> TYPE: DNA
<213> ORGANISM: Artificial
<220> FEATURE:
<223> OTHER INFORMATION: Nucleic acid encoding IgG3 hinge-hIFN gamma

<400> SEQUENCE: 89
cttgagctca aaaccccact tggtgacaca actcacacat gcccacggtg cccagagccc    60
aaatcttgtg acacacctcc cccgtgccca aggtgcccag agcccaaatc ttgtgacaca   120
cctcccccgt gcccaaggtg cccagagccc aaatcttgtg acacacctcc cccgtgccca   180
aggtgcccag gcggccagga tccctacgtg aaggaggccg agaacctgaa gaagtacttc   240
aacgccggcc actccgacgt ggccgacaac ggcaccctgt tcctgggcat cctgaagaac   300
tggaaggagg agtccgacag gaagatcatg cagtcccaga tcgtgtcctt ctacttcaag   360
ctgttcaaga acttcaagga cgaccagtcc atccagaagt ccgtggagac catcaaggag   420
gacatgaacg tgaagttctt caactccaac aagaagaagg gggacgactt cgagaagctg   480
accaactact ccgtgaccga cctgaacgtg cagaggaagg ccatccacga gctgatccag   540
gtgatggccg agctgtcccc cgccgccaag accggcaaga ggaagaggtc ccagatg     597

<210> SEQ ID NO 90
<211> LENGTH: 152
<212> TYPE: PRT
<213> ORGANISM: Artificial
<220> FEATURE:
<223> OTHER INFORMATION: IgG1 hinge delta cys-HIFN gamma

<400> SEQUENCE: 90

Leu Glu Pro Lys Ser Ser Asp Lys Thr His Thr Ser Pro Pro Ser Pro
1               5                   10                  15

Gly Gly Gln Asp Pro Tyr Val Lys Glu Ala Glu Asn Leu Lys Lys Tyr
            20                  25                  30

Phe Asn Ala Gly His Ser Asp Val Ala Asp Asn Gly Thr Leu Phe Leu
        35                  40                  45

Gly Ile Leu Lys Asn Trp Lys Glu Glu Ser Asp Arg Lys Ile Met Gln
    50                  55                  60

Ser Gln Ile Val Ser Phe Tyr Phe Lys Leu Phe Lys Asn Phe Lys Asp
65                  70                  75                  80

Asp Gln Ser Ile Gln Lys Ser Val Glu Thr Ile Lys Glu Asp Met Asn
                85                  90                  95

Val Lys Phe Phe Asn Ser Asn Lys Lys Lys Arg Asp Asp Phe Glu Lys
            100                 105                 110

Leu Thr Asn Tyr Ser Val Thr Asp Leu Asn Val Gln Arg Lys Ala Ile
        115                 120                 125

His Glu Leu Ile Gln Val Met Ala Glu Leu Ser Pro Ala Ala Lys Thr
    130                 135                 140

Gly Lys Arg Lys Arg Ser Gln Met
145                 150

<210> SEQ ID NO 91
<211> LENGTH: 456
<212> TYPE: DNA
<213> ORGANISM: Artificial
<220> FEATURE:
<223> OTHER INFORMATION: Nucleic acid encoding IgG1 hinge delta cys-HIFN gamma

<400> SEQUENCE: 91

```
cttgagccca atcttccga caaaactcac acatctccac cgtccccagg cggccaggat       60
ccctacgtga aggaggccga gaacctgaag aagtacttca cgccggcca ctccgacgtg      120
gccgacaacg gcaccctgtt cctgggcatc ctgaagaact ggaaggagga gtccgacagg    180
aagatcatgc agtcccagat cgtgtccttc tacttcaagc tgttcaagaa cttcaaggac    240
gaccagtcca tccagaagtc cgtggagacc atcaaggagg acatgaacgt gaagttcttc    300
aactccaaca gaagaagag ggacgacttc gagaagctga ccaactactc cgtgaccgac     360
ctgaacgtgc agaggaaggc catccacgag ctgatccagg tgatggccga gctgtccccc   420
gccgccaaga ccggcaagag gaagaggtcc cagatg                              456
```

<210> SEQ ID NO 92
<211> LENGTH: 122
<212> TYPE: PRT
<213> ORGANISM: Artificial
<220> FEATURE:
<223> OTHER INFORMATION: Antibody MAA VH

<400> SEQUENCE: 92

```
Gln Val Lys Leu Gln Gln Ser Gly Gly Gly Leu Val Gln Pro Gly Gly
1               5                   10                  15
Ser Met Lys Leu Ser Cys Val Val Ser Gly Phe Thr Phe Ser Asn Tyr
            20                  25                  30
Trp Met Asn Trp Val Arg Gln Ser Pro Glu Lys Gly Leu Glu Trp Ile
        35                  40                  45
Ala Glu Ile Arg Leu Lys Ser Asn Asn Phe Gly Arg Tyr Tyr Ala Glu
    50                  55                  60
Ser Val Lys Gly Arg Phe Thr Ile Ser Arg Asp Asp Ser Lys Ser Ser
65                  70                  75                  80
Ala Tyr Leu Gln Met Ile Asn Leu Arg Ala Glu Asp Thr Gly Ile Tyr
                85                  90                  95
Tyr Cys Thr Ser Tyr Gly Asn Tyr Val Gly His Tyr Phe Asp His Trp
                100                 105                 110
Gly Gln Gly Thr Thr Val Thr Val Ser Ser
            115                 120
```

<210> SEQ ID NO 93
<211> LENGTH: 367
<212> TYPE: DNA
<213> ORGANISM: Artificial
<220> FEATURE:
<223> OTHER INFORMATION: Nucleic acid encoding antibody MAA VH

<400> SEQUENCE: 93

```
caagtcaaac tgcagcagag cggtggaggc ctggtgcagc ctggtggcag catgaagctg      60
agctgcgtcg tgagcggctt caccttcagc aactactgga tgaactgggt ccggcagagc    120
cccgagaagg gcctggaatg gatcgccgag atccggctga aaagcaacaa cttcggccgg    180
tactacgccg agagcgtgaa gggccggttc accatcagcc gggacgacag caagagcagc    240
```

```
gcctacctgc agatgatcaa cctgcgggcc gaggacaccg gcatctacta ctgcaccagc    300
tacggcaact acgtgggcca ctacttcgac cactggggcc agggcaccac cgtgactgtc    360
agcagcg                                                              367

<210> SEQ ID NO 94
<211> LENGTH: 107
<212> TYPE: PRT
<213> ORGANISM: Artificial
<220> FEATURE:
<223> OTHER INFORMATION: Antibody MAA Vk

<400> SEQUENCE: 94

Asp Ile Glu Leu Thr Gln Ser Pro Lys Phe Met Ser Thr Ser Val Gly
 1               5                  10                  15

Asp Arg Val Ser Val Thr Cys Lys Ala Ser Gln Asn Val Asp Thr Asn
             20                  25                  30

Val Ala Trp Tyr Gln Gln Lys Pro Gly Gln Ser Pro Glu Pro Leu Leu
         35                  40                  45

Phe Ser Ala Ser Tyr Arg Tyr Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Gly Gly Thr Lys Leu Glu Ile Lys
            100                 105

<210> SEQ ID NO 95
<211> LENGTH: 322
<212> TYPE: DNA
<213> ORGANISM: Artificial
<220> FEATURE:
<223> OTHER INFORMATION: Nucleic acid encoding antibody MAA Vk

<400> SEQUENCE: 95
gacatcgagc tgacccagag cccaagttc atgagcacca gcgtgggcga cagagtgtcc     60
gtgacctgca aggccagcca gaacgtggac accaacgtgg cctggtatca gcagaagccc    120
ggccagagcc ctgagcctct gctgttcagc gccagctaca gatacaccgg cgtgcccgac    180
agattcacag gcagcggctc cggcaccgac ttcaccctga ccatcagcaa cgtgcagagc    240
gaggacctgg ccgagtactt ctgccagcag tacaacagct accccctgac cttcggcgga    300
ggcaccaagc tggaaatcaa gc                                             322
```